United States Patent
Aragones et al.

(10) Patent No.: US 12,400,756 B2
(45) Date of Patent: Aug. 26, 2025

(54) METHOD AND SYSTEM FOR AUTOMATED PERSONAL TRAINING THAT INCLUDES TRAINING PROGRAMS

(71) Applicant: NIKE, Inc., Beaverton, OR (US)

(72) Inventors: Tesa Aragones, Portland, OR (US); Adriana Guerrero, Beaverton, OR (US); Christina S. Self, Portland, OR (US); Jay C. Blahnik, Laguna Beach, CA (US); Paul T. Winsper, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/609,084

(22) Filed: May 31, 2017

(65) Prior Publication Data

US 2017/0266502 A1 Sep. 21, 2017

Related U.S. Application Data

(63) Continuation of application No. 15/255,566, filed on Sep. 2, 2016, now abandoned, which is a continuation
(Continued)

(51) Int. Cl.
*G16H 40/67* (2018.01)
*A61B 5/00* (2006.01)
(Continued)

(52) U.S. Cl.
CPC ........... *G16H 40/67* (2018.01); *A61B 5/0205* (2013.01); *A61B 5/02405* (2013.01);
(Continued)

(58) Field of Classification Search
CPC ................ A63F 5/16; A63F 2300/1012; A63F 2300/1093; A63F 2300/303;
(Continued)

(56) References Cited

U.S. PATENT DOCUMENTS 3,145,484 A 8/1964 Bayley
4,860,763 A 8/1989 Schminke
(Continued)

FOREIGN PATENT DOCUMENTS

CA 2512601 A1 3/2002
CN 1415271 A 5/2003
(Continued)

OTHER PUBLICATIONS

Jun. 27, 2013 (WO)—International Preliminary Report on Patentability—App. No. PCT/US2011/064711.
(Continued)

*Primary Examiner* — Jack Yip
(74) *Attorney, Agent, or Firm* — Banner & Witcoff, Ltd.

(57) ABSTRACT

Systems and methods for creating personalized exercise programs are disclosed. An image capture device and a computer device are used to capture images of a user while the user performs athletic movements. The images may then be evaluated to create a human movement screen score. The human movement screen score, goal and time commitment information may then be used to create a personalized exercise program tailored to the specific user.

23 Claims, 61 Drawing Sheets

Related U.S. Application Data of application No. 13/304,064, filed on Nov. 23, 2011, now Pat. No. 9,457,256, which is a continuation-in-part of application No. 13/290,359, filed on Nov. 7, 2011, now Pat. No. 9,283,429.

(60) Provisional application No. 61/433,792, filed on Jan. 18, 2011, provisional application No. 61/432,472, filed on Jan. 13, 2011, provisional application No. 61/422,511, filed on Dec. 13, 2010, provisional application No. 61/417,102, filed on Nov. 24, 2010, provisional application No. 61/410,777, filed on Nov. 5, 2010.

(51) Int. Cl.

| | | |
|---|---|---|
| *A61B 5/0205* | (2006.01) | |
| *A61B 5/024* | (2006.01) | |
| *A61B 5/0255* | (2006.01) | |
| *A61B 5/11* | (2006.01) | |
| *A63B 21/00* | (2006.01) | |
| *A63B 24/00* | (2006.01) | |
| *A63B 71/06* | (2006.01) | |
| *G09B 19/00* | (2006.01) | |
| *G16H 20/30* | (2018.01) | |

(52) U.S. Cl.
CPC ...... *A61B 5/02427* (2013.01); *A61B 5/02438* (2013.01); *A61B 5/0255* (2013.01); *A61B 5/11* (2013.01); *A61B 5/1118* (2013.01); *A61B 5/4866* (2013.01); *A61B 5/681* (2013.01); *A61B 5/6824* (2013.01); *A61B 5/6829* (2013.01); *A61B 5/6831* (2013.01); *A61B 5/684* (2013.01); *A63B 21/00069* (2013.01); *A63B 21/00076* (2013.01); *A63B 24/00* (2013.01); *A63B 24/0006* (2013.01); *A63B 24/0062* (2013.01); *A63B 24/0075* (2013.01); *A63B 71/0622* (2013.01); *G09B 19/003* (2013.01); *G09B 19/0038* (2013.01); *G16H 20/30* (2018.01); *A63B 2024/0012* (2013.01); *A63B 2024/0015* (2013.01); *A63B 2024/0071* (2013.01); *A63B 2024/0078* (2013.01); *A63B 2024/0096* (2013.01); *A63B 2071/0636* (2013.01); *A63B 2071/0647* (2013.01); *A63B 2071/0663* (2013.01); *A63B 2071/0677* (2013.01); *A63B 2220/13* (2013.01); *A63B 2220/40* (2013.01); *A63B 2220/51* (2013.01); *A63B 2220/803* (2013.01); *A63B 2220/806* (2013.01); *A63B 2220/836* (2013.01); *A63B 2225/50* (2013.01); *A63F 2300/1012* (2013.01); *A63F 2300/1093* (2013.01); *A63F 2300/303* (2013.01); *A63F 2300/6045* (2013.01); *A63F 2300/8005* (2013.01)

(58) Field of Classification Search
CPC ..... A63F 2300/6045; A63F 2300/8005; G06F 19/3481; G09B 5/00; G09B 19/003; G09B 19/0038; G16H 40/67; G16H 20/30; A61B 5/0205; A61B 5/02405; A61B 5/02427; A61B 5/02438; A61B 5/0255; A61B 5/11; A61B 5/1118; A61B 5/4866; A61B 5/681; A61B 5/6824; A61B 5/6829; A61B 5/6831; A61B 5/684; A63B 21/00069; A63B 21/00076; A63B 24/00; A63B 24/0006; A63B 24/0062; A63B 24/0075; A63B 71/0622; A63B 2024/0012; A63B 2024/0015; A63B 2024/0071; A63B 2024/0078; A63B 2024/0096; A63B 2071/0636; A63B 2071/0647; A63B 2071/0663; A63B 2071/0677; A63B 2220/13; A63B 2220/40; A63B 2220/51; A63B 2220/803; A63B 2220/806; A63B 2220/836; A63B 2225/50

See application file for complete search history.

(56) References Cited

U.S. PATENT DOCUMENTS

| | | | |
|---|---|---|---|
| 4,911,427 A | 3/1990 | Matsumoto et al. | |
| 4,938,476 A | 7/1990 | Brunelle et al. | |
| 5,184,295 A | 2/1993 | Mann | |
| 5,277,197 A | 1/1994 | Church et al. | |
| 5,288,078 A | 2/1994 | Capper et al. | |
| 5,335,188 A | 8/1994 | Brisson | |
| 5,354,317 A | 10/1994 | Alt | |
| 5,375,610 A | 12/1994 | LaCourse et al. | |
| 5,511,789 A | 4/1996 | Nakamura | |
| 5,524,637 A | 6/1996 | Erickson | |
| 5,527,239 A | 6/1996 | Abbondanza | |
| 5,598,849 A | 2/1997 | Browne | |
| 5,626,538 A | 5/1997 | Dalebout et al. | |
| 5,655,316 A | 8/1997 | Huang | |
| 5,667,459 A | 9/1997 | Su | |
| 5,688,137 A | 11/1997 | Bustance | |
| 5,791,351 A | 8/1998 | Curchod | |
| 5,826,578 A | 10/1998 | Curchod | |
| 5,836,770 A | 11/1998 | Powers | |
| 5,846,086 A | 12/1998 | Bizzi et al. | |
| 5,851,193 A | 12/1998 | Arikka et al. | |
| 5,879,270 A | 3/1999 | Huish et al. | |
| 5,888,172 A | 3/1999 | Andrus et al. | |
| 5,904,484 A | 5/1999 | Burns | |
| 5,913,727 A | 6/1999 | Ahdoot | |
| 5,919,149 A | 7/1999 | Allum | |
| 5,938,690 A | 8/1999 | Aw et al. | |
| 5,955,957 A | 9/1999 | Calabrese et al. | |
| 5,976,083 A | 11/1999 | Richardson et al. | |
| 6,013,007 A * | 1/2000 | Root | G01C 22/00 |
| | | | 482/902 |
| 6,026,335 A | 2/2000 | Atlas | |
| 6,032,108 A | 2/2000 | Seiple et al. | |
| 6,077,193 A | 6/2000 | Buhler et al. | |
| 6,126,449 A | 10/2000 | Burns | |
| 6,308,565 B1 | 10/2001 | French et al. | |
| 6,316,934 B1 | 11/2001 | Amorai-Moriya et al. | |
| 6,416,327 B1 | 7/2002 | Wittenbecher | |
| 6,428,449 B1 | 8/2002 | Apseloff | |
| 6,443,904 B2 | 9/2002 | Nissila | |
| 6,458,060 B1 | 10/2002 | Watterson et al. | |
| 6,493,652 B1 | 12/2002 | Ohlenbusch et al. | |
| 6,516,222 B2 | 2/2003 | Fukuda | |
| 6,527,674 B1 | 3/2003 | Clem | |
| 6,585,622 B1 | 7/2003 | Shum et al. | |
| 6,601,016 B1 | 7/2003 | Brown et al. | |
| 6,607,493 B2 | 8/2003 | Song | |
| 6,648,798 B2 | 11/2003 | Yoo | |
| 6,656,091 B1 | 12/2003 | Abelbeck et al. | |
| 6,663,491 B2 | 12/2003 | Watabe et al. | |
| 6,672,991 B2 | 1/2004 | O'Malley | |
| 6,687,535 B2 | 2/2004 | Hautala et al. | |
| 6,736,759 B1 | 5/2004 | Stubbs et al. | |
| 6,743,167 B2 | 6/2004 | Balkin et al. | |
| 6,746,371 B1 * | 6/2004 | Brown | A63B 24/0084 |
| | | | 482/8 |
| 6,749,432 B2 | 6/2004 | French et al. | |
| 6,765,726 B2 | 7/2004 | French et al. | |
| 6,786,848 B2 | 9/2004 | Yamashita et al. | |
| 6,788,200 B1 | 9/2004 | Jamel et al. | |
| 6,796,927 B2 | 9/2004 | Toyama | |
| 6,817,979 B2 | 11/2004 | Nihtila | |
| 6,820,025 B2 | 11/2004 | Bachmann et al. | |
| 6,834,436 B2 | 12/2004 | Townsend et al. | |
| 6,836,744 B1 | 12/2004 | Asphahani et al. | |
| 6,856,852 B1 | 2/2005 | Bruinsma et al. | |

(56) References Cited

U.S. PATENT DOCUMENTS

| | | |
|---|---|---|
| 6,858,006 B2 | 2/2005 | MacCarter et al. |
| 6,876,496 B2 | 4/2005 | French et al. |
| 6,902,513 B1 | 6/2005 | McClure |
| 6,997,852 B2 | 2/2006 | Watterson et al. |
| 7,018,211 B1 | 3/2006 | Birkholzer et al. |
| 7,054,678 B2 | 5/2006 | Pardik et al. |
| 7,074,168 B1 | 7/2006 | Farnes et al. |
| 7,076,291 B2 | 7/2006 | Pulkkinen et al. |
| 7,079,889 B2 | 7/2006 | Nakada |
| 7,089,216 B2 | 8/2006 | Van Overveld |
| 7,095,424 B2 | 8/2006 | Satoh et al. |
| 7,097,588 B2 | 8/2006 | Watterson et al. |
| 7,163,490 B2 | 1/2007 | Chen |
| 7,166,062 B1 | 1/2007 | Watterson et al. |
| 7,172,530 B1* | 2/2007 | Hercules ............... G16H 40/67 482/4 |
| 7,192,401 B2 | 3/2007 | Saalasti et al. |
| 7,254,516 B2 | 8/2007 | Case, Jr. et al. |
| 7,265,666 B2 | 9/2007 | Daniel |
| 7,315,249 B2 | 1/2008 | Littell |
| 7,359,121 B2 | 4/2008 | French et al. |
| 7,433,805 B2 | 10/2008 | Vock et al. |
| 7,442,131 B2 | 10/2008 | Milana |
| 7,480,512 B2 | 1/2009 | Graham et al. |
| 7,493,232 B1 | 2/2009 | Surina |
| 7,497,807 B2 | 3/2009 | Neff et al. |
| 7,497,812 B2 | 3/2009 | Neff et al. |
| 7,556,590 B2 | 7/2009 | Watterson et al. |
| 7,559,877 B2 | 7/2009 | Parks et al. |
| 7,602,301 B1 | 10/2009 | Stirling et al. |
| 7,628,730 B1 | 12/2009 | Watterson et al. |
| 7,676,332 B2 | 3/2010 | Damen |
| 7,699,753 B2 | 4/2010 | Daikeler et al. |
| 7,717,858 B2 | 5/2010 | Massad |
| 7,722,502 B2 | 5/2010 | Holkkola |
| 7,736,272 B2 | 6/2010 | Martens |
| 7,771,293 B1 | 8/2010 | Vann |
| 7,771,320 B2 | 8/2010 | Riley et al. |
| 7,782,358 B2 | 8/2010 | Nieminen et al. |
| 7,783,347 B2 | 8/2010 | Abourizk et al. |
| 7,789,800 B1 | 9/2010 | Watterson et al. |
| 7,810,392 B2 | 10/2010 | Kitagawa |
| 7,815,508 B2 | 10/2010 | Dohta |
| 7,821,407 B2 | 10/2010 | Shears et al. |
| 7,825,815 B2 | 11/2010 | Shears et al. |
| 7,846,067 B2 | 12/2010 | Hanoun |
| 7,846,069 B2 | 12/2010 | Martens |
| 7,850,514 B2 | 12/2010 | Weber |
| 7,857,708 B2 | 12/2010 | Ueda et al. |
| 7,894,849 B2 | 2/2011 | Kass et al. |
| 7,927,253 B2 | 4/2011 | Vincent et al. |
| 7,967,728 B2 | 6/2011 | Zavadsky et al. |
| 7,978,081 B2 | 7/2011 | Shears et al. |
| 7,978,217 B2 | 7/2011 | Camhi |
| 7,985,164 B2 | 7/2011 | Ashby |
| 7,988,647 B2 | 8/2011 | Bunn et al. |
| 8,012,064 B2 | 9/2011 | Martens |
| 8,029,411 B2 | 10/2011 | Johnson |
| 8,038,549 B2 | 10/2011 | Vann |
| 8,038,578 B2 | 10/2011 | Olrik et al. |
| 8,083,643 B2* | 12/2011 | Ng ......................... G06Q 10/02 482/1 |
| 8,109,858 B2 | 2/2012 | Redmann |
| 8,118,710 B2 | 2/2012 | Weinman et al. |
| 8,177,260 B2 | 5/2012 | Tropper et al. |
| 8,212,136 B2 | 7/2012 | Shirai et al. |
| 8,230,367 B2 | 7/2012 | Bell et al. |
| 8,235,870 B2 | 8/2012 | Hamilton |
| 8,253,586 B1 | 8/2012 | Matak |
| 8,269,826 B2 | 9/2012 | Nieminen et al. |
| 8,284,157 B2 | 10/2012 | Markovic et al. |
| 8,284,847 B2 | 10/2012 | Adermann |
| 8,346,524 B2 | 1/2013 | Turgiss et al. |
| 8,409,057 B2 | 4/2013 | Martens |
| 8,435,177 B2 | 5/2013 | Lanfermann et al. |
| 8,460,199 B2 | 6/2013 | Rulkov et al. |
| 8,465,108 B2 | 6/2013 | Markovic et al. |
| 8,503,086 B2 | 8/2013 | French et al. |
| 8,523,667 B2 | 9/2013 | Clavin et al. |
| 8,568,277 B2 | 10/2013 | Johnson |
| 8,568,330 B2 | 10/2013 | Mollicone et al. |
| 8,589,114 B2 | 11/2013 | Papadourakis |
| 8,602,988 B2 | 12/2013 | Hunt et al. |
| 8,616,989 B2 | 12/2013 | Bentley |
| 8,676,541 B2 | 3/2014 | Schrock et al. |
| 8,702,485 B2 | 4/2014 | Flury et al. |
| 8,758,201 B2 | 6/2014 | Ashby et al. |
| 8,784,270 B2 | 7/2014 | Ashby et al. |
| 8,784,307 B1 | 7/2014 | Groteke et al. |
| 8,812,428 B2 | 8/2014 | Mollicone et al. |
| 8,814,755 B2 | 8/2014 | Ellis et al. |
| 8,845,496 B2 | 9/2014 | Arrasvuori et al. |
| 8,854,304 B2 | 10/2014 | Nishimoto et al. |
| 8,858,400 B2 | 10/2014 | Johnson |
| 8,861,091 B2 | 10/2014 | French et al. |
| 8,892,219 B2 | 11/2014 | Pryor |
| 8,911,328 B2 | 12/2014 | Alessandri et al. |
| 8,928,484 B2 | 1/2015 | Chang et al. |
| 9,008,973 B2 | 4/2015 | French |
| 9,078,585 B2 | 7/2015 | Miyazaki et al. |
| 9,141,759 B2 | 9/2015 | Burich et al. |
| 9,149,222 B1 | 10/2015 | Zets et al. |
| 9,154,739 B1 | 10/2015 | Nicolaou et al. |
| 9,317,660 B2 | 4/2016 | Burich et al. |
| 9,329,053 B2 | 5/2016 | Lakovic et al. |
| 9,390,229 B1 | 7/2016 | Kahn et al. |
| 9,504,414 B2 | 11/2016 | Coza et al. |
| 9,545,541 B2 | 1/2017 | Aragones et al. |
| 9,630,059 B2 | 4/2017 | Burich et al. |
| 10,610,761 B1 | 4/2020 | Matak et al. |
| 2001/0034014 A1 | 10/2001 | Nishimoto et al. |
| 2002/0019258 A1 | 2/2002 | Kim et al. |
| 2002/0077219 A1 | 6/2002 | Cohen et al. |
| 2002/0116147 A1 | 8/2002 | Vock et al. |
| 2002/0160883 A1 | 10/2002 | Dugan |
| 2002/0183961 A1 | 12/2002 | French et al. |
| 2003/0040348 A1 | 2/2003 | Martens |
| 2003/0054327 A1 | 3/2003 | Evensen |
| 2003/0065561 A1 | 4/2003 | Brown et al. |
| 2003/0077556 A1 | 4/2003 | French et al. |
| 2003/0134714 A1 | 7/2003 | Oishi et al. |
| 2003/0190062 A1 | 10/2003 | Noro et al. |
| 2003/0214408 A1 | 11/2003 | Grajales et al. |
| 2003/0228033 A1 | 12/2003 | Daniel et al. |
| 2003/0228628 A1 | 12/2003 | Powell |
| 2004/0087366 A1 | 5/2004 | Shum et al. |
| 2004/0102931 A1 | 5/2004 | Ellis et al. |
| 2004/0112151 A1 | 6/2004 | Maxwell et al. |
| 2004/0162194 A1 | 8/2004 | Habing |
| 2004/0219498 A1 | 11/2004 | Davidson |
| 2004/0220856 A1 | 11/2004 | Moore |
| 2004/0255490 A1 | 12/2004 | Wan et al. |
| 2005/0001728 A1 | 1/2005 | Appelt et al. |
| 2005/0038679 A1 | 2/2005 | Short |
| 2005/0070809 A1 | 3/2005 | Acres |
| 2005/0079905 A1 | 4/2005 | Martens |
| 2005/0085348 A1 | 4/2005 | Kiefer et al. |
| 2005/0101845 A1 | 5/2005 | Nihtila |
| 2005/0101887 A1 | 5/2005 | Stark et al. |
| 2005/0107723 A1 | 5/2005 | Wehman et al. |
| 2005/0113650 A1 | 5/2005 | Pacione et al. |
| 2005/0113652 A1 | 5/2005 | Stark et al. |
| 2005/0172311 A1 | 8/2005 | Hjelt et al. |
| 2005/0182341 A1 | 8/2005 | Katayama et al. |
| 2005/0196737 A1 | 9/2005 | Mann |
| 2005/0209050 A1 | 9/2005 | Bartels |
| 2005/0223799 A1 | 10/2005 | Murphy |
| 2005/0233861 A1 | 10/2005 | Hickman et al. |
| 2005/0234307 A1 | 10/2005 | Heinonen et al. |
| 2005/0239026 A1 | 10/2005 | Suzuki et al. |
| 2005/0250458 A1* | 11/2005 | Graham ............... G09B 19/0092 455/121 |
| 2005/0272517 A1 | 12/2005 | Funk et al. |
| 2005/0272564 A1 | 12/2005 | Pyles et al. |

(56) References Cited

U.S. PATENT DOCUMENTS

| | | |
|---|---|---|
| 2006/0003872 A1 | 1/2006 | Chiles et al. |
| 2006/0025282 A1 | 2/2006 | Redmann |
| 2006/0040793 A1 | 2/2006 | Martens |
| 2006/0079800 A1 | 4/2006 | Martikka et al. |
| 2006/0088806 A1* | 4/2006 | Quinn .................... G09B 7/02 434/236 |
| 2006/0111944 A1 | 5/2006 | Sirmans et al. |
| 2006/0136173 A1* | 6/2006 | Case, Jr. ............... A63B 24/00 702/182 |
| 2006/0166737 A1* | 7/2006 | Bentley ................. A63B 69/36 463/43 |
| 2006/0173070 A1 | 8/2006 | Murase et al. |
| 2006/0183602 A1 | 8/2006 | Astilean |
| 2006/0189440 A1 | 8/2006 | Gravagne |
| 2006/0205569 A1 | 9/2006 | Watterson et al. |
| 2006/0228681 A1* | 10/2006 | Clarke .................. G16H 20/30 434/236 |
| 2006/0229170 A1 | 10/2006 | Ozawa et al. |
| 2006/0241521 A1 | 10/2006 | Cohen |
| 2006/0247070 A1 | 11/2006 | Funk et al. |
| 2006/0252617 A1 | 11/2006 | Gill |
| 2006/0262120 A1 | 11/2006 | Rosenberg |
| 2006/0282021 A1 | 12/2006 | DeVaul et al. |
| 2006/0284979 A1 | 12/2006 | Clarkson |
| 2006/0293617 A1 | 12/2006 | Einav et al. |
| 2007/0032345 A1 | 2/2007 | Padmanabhan et al. |
| 2007/0050715 A1 | 3/2007 | Behar |
| 2007/0118406 A1 | 5/2007 | Killin et al. |
| 2007/0155588 A1 | 7/2007 | Stark et al. |
| 2007/0177024 A1 | 8/2007 | Camhi |
| 2007/0213178 A1 | 9/2007 | Lemmela |
| 2007/0232453 A1 | 10/2007 | Hanoun |
| 2007/0232455 A1 | 10/2007 | Hanoun |
| 2007/0239479 A1 | 10/2007 | Arrasvuori et al. |
| 2007/0270214 A1 | 11/2007 | Bentley |
| 2007/0271065 A1 | 11/2007 | Gupta et al. |
| 2007/0272011 A1 | 11/2007 | Chapa et al. |
| 2008/0033581 A1 | 2/2008 | Doshi et al. |
| 2008/0076637 A1* | 3/2008 | Gilley ................ G06Q 30/0201 482/9 |
| 2008/0077620 A1* | 3/2008 | Gilley .................... G16H 40/63 |
| 2008/0096726 A1 | 4/2008 | Riley et al. |
| 2008/0146302 A1 | 6/2008 | Olsen et al. |
| 2008/0161733 A1 | 7/2008 | Einav et al. |
| 2008/0176655 A1* | 7/2008 | James ................. G06F 19/3475 463/42 |
| 2008/0189291 A1 | 8/2008 | Hsu |
| 2008/0191864 A1 | 8/2008 | Wolfson |
| 2008/0200312 A1 | 8/2008 | Tagliabue |
| 2008/0207401 A1 | 8/2008 | Harding et al. |
| 2008/0212032 A1 | 9/2008 | Seiller et al. |
| 2008/0221487 A1 | 9/2008 | Zohar et al. |
| 2008/0246629 A1 | 10/2008 | Tsui et al. |
| 2008/0254866 A1 | 10/2008 | Young et al. |
| 2008/0267444 A1 | 10/2008 | Simons-Nikolova et al. |
| 2008/0269016 A1* | 10/2008 | Ungari ................ A63B 69/0053 482/1 |
| 2008/0281550 A1 | 11/2008 | Hogle et al. |
| 2009/0023555 A1* | 1/2009 | Raymond ............. G06Q 10/10 482/9 |
| 2009/0042695 A1 | 2/2009 | Chien et al. |
| 2009/0044429 A1 | 2/2009 | Cook et al. |
| 2009/0062092 A1 | 3/2009 | Mortimer et al. |
| 2009/0069722 A1 | 3/2009 | Flaction et al. |
| 2009/0098519 A1 | 4/2009 | Byerly |
| 2009/0118100 A1 | 5/2009 | Oliver et al. |
| 2009/0144369 A1 | 6/2009 | Brown |
| 2009/0149299 A1 | 6/2009 | Tchao et al. |
| 2009/0150178 A1 | 6/2009 | Sutton et al. |
| 2009/0171614 A1 | 7/2009 | Damen |
| 2009/0209358 A1 | 8/2009 | Niegowski |
| 2009/0227876 A1 | 9/2009 | Tran |
| 2009/0233769 A1 | 9/2009 | Pryor |
| 2009/0233770 A1 | 9/2009 | Vincent et al. |
| 2009/0258710 A1* | 10/2009 | Quatrochi .......... A63B 24/0062 463/43 |
| 2009/0269728 A1 | 10/2009 | Verstegen et al. |
| 2009/0298024 A1 | 12/2009 | Batzler et al. |
| 2009/0298650 A1 | 12/2009 | Kutliroff |
| 2009/0299232 A1 | 12/2009 | Lanfermann et al. |
| 2010/0016678 A1* | 1/2010 | Beck .................. A61N 1/37247 600/300 |
| 2010/0036288 A1 | 2/2010 | Lanfermann et al. |
| 2010/0056340 A1 | 3/2010 | Ellis et al. |
| 2010/0063778 A1 | 3/2010 | Schrock et al. |
| 2010/0063779 A1 | 3/2010 | Schrock et al. |
| 2010/0069148 A1 | 3/2010 | Cargill |
| 2010/0088023 A1 | 4/2010 | Werner |
| 2010/0094174 A1 | 4/2010 | Choi et al. |
| 2010/0105531 A1 | 4/2010 | Crawford |
| 2010/0125026 A1 | 5/2010 | Zavadsky et al. |
| 2010/0125028 A1 | 5/2010 | Heppert |
| 2010/0137748 A1 | 6/2010 | Sone et al. |
| 2010/0144414 A1* | 6/2010 | Edis .................. A63B 24/0006 463/8 |
| 2010/0197462 A1 | 8/2010 | Piane, Jr. |
| 2010/0204616 A1 | 8/2010 | Shears et al. |
| 2010/0205542 A1* | 8/2010 | Walman ............... G06Q 10/10 715/753 |
| 2010/0210359 A1 | 8/2010 | Krzeslo et al. |
| 2010/0210975 A1 | 8/2010 | Anthony, III et al. |
| 2010/0217738 A1 | 8/2010 | Sarel |
| 2010/0227302 A1 | 9/2010 | McGilvery et al. |
| 2010/0234184 A1 | 9/2010 | Le Page et al. |
| 2010/0248901 A1 | 9/2010 | Martens |
| 2010/0273610 A1 | 10/2010 | Johnson |
| 2010/0277411 A1 | 11/2010 | Yee et al. |
| 2010/0281432 A1 | 11/2010 | Geisner et al. |
| 2010/0302142 A1 | 12/2010 | French et al. |
| 2010/0306712 A1 | 12/2010 | Snook et al. |
| 2010/0316983 A1 | 12/2010 | Johns, Jr. |
| 2010/0332243 A1 | 12/2010 | Weigman et al. |
| 2011/0027135 A1 | 2/2011 | Michiaki et al. |
| 2011/0039659 A1 | 2/2011 | Kim et al. |
| 2011/0072457 A1 | 3/2011 | Lanfermann et al. |
| 2011/0077129 A1 | 3/2011 | Martens |
| 2011/0082397 A1 | 4/2011 | Alberts |
| 2011/0111922 A1 | 5/2011 | Weinman et al. |
| 2011/0111924 A1 | 5/2011 | Jones et al. |
| 2011/0112771 A1 | 5/2011 | French |
| 2011/0131005 A1 | 6/2011 | Ueshima et al. |
| 2011/0136627 A1 | 6/2011 | Williams |
| 2011/0158912 A1 | 6/2011 | Wright et al. |
| 2011/0212791 A1 | 9/2011 | Ueda et al. |
| 2011/0224557 A1 | 9/2011 | Banet et al. |
| 2011/0229864 A1 | 9/2011 | Short et al. |
| 2011/0251021 A1 | 10/2011 | Zavadsky et al. |
| 2011/0251495 A1 | 10/2011 | Province et al. |
| 2011/0270135 A1 | 11/2011 | Dooley et al. |
| 2011/0275907 A1 | 11/2011 | Inciardi et al. |
| 2011/0281249 A1* | 11/2011 | Gammell ............... G16H 10/20 434/247 |
| 2011/0304497 A1 | 12/2011 | Molyneux et al. |
| 2011/0306491 A1 | 12/2011 | Belisle |
| 2011/0307821 A1 | 12/2011 | Martens |
| 2012/0015778 A1* | 1/2012 | Lee ....................... G16H 40/63 482/8 |
| 2012/0034971 A1 | 2/2012 | Harp et al. |
| 2012/0038627 A1 | 2/2012 | Sung et al. |
| 2012/0041767 A1 | 2/2012 | Hoffman et al. |
| 2012/0052972 A1 | 3/2012 | Bentley |
| 2012/0077641 A1* | 3/2012 | Dyer .................... A63B 22/0605 715/810 |
| 2012/0130515 A1 | 5/2012 | Homsi et al. |
| 2012/0130886 A1 | 5/2012 | Shergill et al. |
| 2012/0143064 A1 | 6/2012 | Cyphery et al. |
| 2012/0143358 A1 | 6/2012 | Adams et al. |
| 2012/0165703 A1 | 6/2012 | Bottum et al. |
| 2012/0183939 A1 | 7/2012 | Aragones et al. |
| 2012/0183940 A1 | 7/2012 | Aragones et al. |
| 2012/0190505 A1 | 7/2012 | Shavit et al. |
| 2012/0234111 A1 | 9/2012 | Molyneux et al. |
| 2012/0253484 A1 | 10/2012 | Burich et al. |

(56) References Cited

U.S. PATENT DOCUMENTS

| | | |
|---|---|---|
| 2012/0254934 A1 | 10/2012 | Mcbrearty et al. |
| 2012/0268592 A1 | 10/2012 | Aragones et al. |
| 2012/0271143 A1 | 10/2012 | Aragones et al. |
| 2012/0274554 A1 | 11/2012 | Kinoshita et al. |
| 2012/0277891 A1 | 11/2012 | Aragones et al. |
| 2012/0291544 A1 | 11/2012 | Kawabe |
| 2012/0315986 A1 | 12/2012 | Walling |
| 2012/0315987 A1 | 12/2012 | Walling |
| 2013/0019694 A1 | 1/2013 | Molyneux et al. |
| 2013/0022947 A1 | 1/2013 | Muniz Simas et al. |
| 2013/0022950 A1 | 1/2013 | Muniz Simas et al. |
| 2013/0108993 A1 | 5/2013 | Katz |
| 2013/0171596 A1 | 7/2013 | French |
| 2013/0268205 A1 | 10/2013 | Aragones et al. |
| 2013/0281796 A1 | 10/2013 | Pan |
| 2013/0295539 A1 | 11/2013 | Wilson et al. |
| 2013/0324368 A1 | 12/2013 | Aragones et al. |
| 2013/0325396 A1* | 12/2013 | Yuen .................. A61B 5/0002 702/160 |
| 2013/0338802 A1 | 12/2013 | Winsper et al. |
| 2014/0073486 A1 | 3/2014 | Ahmed et al. |
| 2014/0278218 A1 | 9/2014 | Chang |
| 2014/0287388 A1 | 9/2014 | Ferrier |
| 2014/0308640 A1 | 10/2014 | Forman et al. |
| 2015/0105881 A1 | 4/2015 | Guerrero et al. |
| 2016/0199693 A1 | 7/2016 | Vermilyea et al. |

FOREIGN PATENT DOCUMENTS

| | | | |
|---|---|---|---|
| CN | 1457246 A | 11/2003 | |
| CN | 1457546 A | 11/2003 | |
| CN | 1723847 A | 1/2006 | |
| CN | 2803449 Y | 8/2006 | |
| CN | 1933880 A | 3/2007 | |
| CN | 101061949 A | 10/2007 | |
| CN | 101202994 A | 6/2008 | |
| CN | 101330863 A | 12/2008 | |
| CN | 201242749 Y | 5/2009 | |
| CN | 101558996 A | 10/2009 | |
| CN | 101668482 A | 3/2010 | |
| CN | 201643611 U | 11/2010 | |
| CN | 101909705 A | 12/2010 | |
| CN | 101910846 A | 12/2010 | |
| CN | 101964047 A | 2/2011 | |
| CN | 101978374 A | 2/2011 | |
| CN | 102068264 A | 5/2011 | |
| CN | 103493056 A | 1/2014 | |
| DE | 29720110 U1 | 1/1998 | |
| EP | 0956819 A1 | 11/1999 | |
| EP | 2324762 A1 | 5/2011 | |
| GB | 2415788 A | 1/2006 | |
| JP | H8-57093 A | 3/1996 | |
| JP | 857093 | 5/1996 | |
| JP | H08251577 A | 9/1996 | |
| JP | H0938051 A | 2/1997 | |
| JP | H10502465 A | 3/1998 | |
| JP | 2000033184 A | 2/2000 | |
| JP | 2000070242 A | 3/2000 | |
| JP | 2000504854 A | 4/2000 | |
| JP | 2001224853 A | 8/2001 | |
| JP | 2001231904 A | 8/2001 | |
| JP | 2001299975 A | 10/2001 | |
| JP | 2002112984 A | 4/2002 | |
| JP | 2002516121 A | 6/2002 | |
| JP | 2002253718 A | 9/2002 | |
| JP | 2002291952 A | 10/2002 | |
| JP | 2003085288 A | 3/2003 | |
| JP | 2003141260 A | 5/2003 | |
| JP | 2003290406 A | 10/2003 | |
| JP | 2004054393 A | 2/2004 | |
| JP | 2004073272 A | 3/2004 | |
| JP | 2004089727 A | 3/2004 | |
| JP | 2004097649 A | 4/2004 | |
| JP | 2004208995 A | 7/2004 | |
| JP | 2005034195 A | 2/2005 | |
| JP | 3656853 B2 | 6/2005 | |
| JP | 2005198818 A | 7/2005 | |
| JP | 2005230068 A | 9/2005 | |
| JP | 2006130127 A | 5/2006 | |
| JP | 2006167313 A | 6/2006 | |
| JP | 2006263002 A | 10/2006 | |
| JP | 2006302122 A | 11/2006 | |
| JP | 2006320424 A | 11/2006 | |
| JP | 2007143748 A | 6/2007 | |
| JP | 2007144107 A | 6/2007 | |
| JP | 2007260307 A | 10/2007 | |
| JP | 2008104758 A | 5/2008 | |
| JP | 2008295746 A | 12/2008 | |
| JP | 2009048757 A | 3/2009 | |
| JP | 2009050699 A | 3/2009 | |
| JP | 2009078134 A | 4/2009 | |
| JP | 2009172315 A | 8/2009 | |
| JP | 2009201672 A | 9/2009 | |
| JP | 2009213656 A | 9/2009 | |
| JP | 2009213782 A | 9/2009 | |
| JP | 2009219828 A | 10/2009 | |
| JP | 2009247836 A | 10/2009 | |
| JP | 2009279041 A | 12/2009 | |
| JP | 2010502368 A | 1/2010 | |
| JP | 2010069102 A | 4/2010 | |
| JP | 2010075715 A | 4/2010 | |
| JP | 2010086358 A | 4/2010 | |
| JP | 2010188159 A | 9/2010 | |
| JP | 2010246636 A | 11/2010 | |
| JP | 2010259456 A | 11/2010 | |
| JP | 2011152333 A | 8/2011 | |
| KR | 20030041034 A | 5/2003 | |
| KR | 20090084035 A | 8/2009 | |
| KR | 20100086052 A | 7/2010 | |
| TW | 200825989 A | 6/2008 | |
| TW | 200915213 A | 4/2009 | |
| TW | 200950748 A | 12/2009 | |
| WO | 9729814 A1 | 8/1997 | |
| WO | 2001045014 A1 | 6/2001 | |
| WO | 2002035997 A1 | 5/2002 | |
| WO | 2002055959 A1 | 7/2002 | |
| WO | 2002067449 A2 | 8/2002 | |
| WO | 2002101408 A1 | 12/2002 | |
| WO | 2004073494 A2 | 9/2004 | |
| WO | 2005018759 A1 | 3/2005 | |
| WO | 2006098282 A1 | 9/2006 | |
| WO | 2006111687 A1 | 10/2006 | |
| WO | 2008060043 A1 | 5/2008 | |
| WO | 2009043024 A1 | 4/2009 | |
| WO | 2009073607 A2 | 6/2009 | |
| WO | 2010121166 A1 | 10/2010 | |
| WO | 2012021633 A2 | 2/2012 | |
| WO | 2012039467 A1 | 3/2012 | |
| WO | 2012061438 A2 | 5/2012 | |
| WO | 2012061804 A1 | 5/2012 | |
| WO | 2012071548 A1 | 5/2012 | |
| WO | 2012071551 A1 | 5/2012 | |

OTHER PUBLICATIONS

May 31, 2013 (WO)—International Search Report and Written Opinion—App. No. PCT/US2012/066070.
May 29, 2013 (WO)—International Search Report and Written Opinion—App. No. PCT/US2012/066065.
Jun. 6, 2013 (WO)—International Preliminary Report on Patentability—App. No. PCT/US20111062117.
May 16, 2013 (WO)—International Preliminary Report on Patentability—App. No. PCT/US20111059559.
Apr. 3, 2012 (WO)—International Search Report and Written Opinion—Application No. PCT/US20111064711.
Feb. 23, 2012—(WO) ISR & WO—App. No. PCT/US2011/062117.
Feb. 20, 2014 (WO)—International Search Report and Written Opinion—App. No. PCT/US2013/067512.
Sep. 12, 2013—(WO) ISR & WO—App. No. PCT/US2013/044109.

(56) References Cited

OTHER PUBLICATIONS

Zhao, et al., Design and Practice for Individual Specialized PC Expert System for College Student, Journal of Xi An Institute of Physical Education, vol. 22, No. 2 (Mar. 2005) pp. 118-121.
Plagge et al: "Design and Evaluation of the T-Team of the University of Tuebingen for RoboCup '98" in "Network and Parallel Computing", Jan. 1, 1999 (Jan. 1, 1999), Springer Inernational Publishing, Cham 032548, XP055334016, ISSN: 0302-9743, ISBN: 978-3-642-23677-8, vol. 1604, pp. 464-472, DOI: 40.1007/3-540-48422-1_47.
United States District Court Southern District of New York (Foley Square), Defendant's "Disclosure of Preliminary Invalidity Contentions", *NIKE, Inc.* v. *Lululemon Athletica Inc et al.*, Case 1:22-cv-00082, filed Jul. 18, 2022, 1097 pages.
United States District Court Southern District of New York (Foley Square), Defendant's "Amended Exhibits", (Exhs. D-1, E-1, E-2, E-3, E-4, E-5, E-6) *Nike, Inc.* v. *Lululemon Athletica Inc et al.*, Case 1:22-cv-00082, filed Jul. 26, 2022, 183 pages.
David R. Bassett, Jr., Validity and Reliability Issues in Objective Monitoring of Physical Activity, Research Quarterly for Exercise and Sport, vol. 71, No. 2, pp. 30-36 (2000) ("Bassett"), 7 pages.
Chris Hall, Nokia Sports Tracker, Pocket-lint (Jul. 25, 2008), https://www.pocket- lint.com/phones/reviews/nokia/70414-nokia-sports-tracker-mobile-application ("Hall"), 11 pages.
Jozsef Hajdu, Provided Services of Social Networks for Sport, TKK T-110.5190 Seminar on Internetworking (Apr. 28-29, 2008), http://www.cse.tkk.fi/en/publications/B/1/papers/Hajdu_final.pdf ("Hajdu"), 8 pages.
Zee, Breaking: Goodbye Twitter? Facebook adds @mentions to status updates (Sep. 10, 2009, 9:16 PM), https://thenextweb.com/news/breaking-facebook-adds-mentions-status-updates?amp=1 ("Zee"), 6 pages.
Robert Anderson (@rsa), Twitter (Nov. 2, 2006, 11:58 PM), https://twitter.com/rsa/status/55281?lang=en ("Anderson"), 3 pages.
Scott Tousignant (@TheFitB), Twitter (Nov. 27, 2008, 12:27 PM), https://twitter.com/TheFitB/status/1026679285 ("Tousignant"), 1 page.
Internet webpage wii.nintendo.com/controller.jsp, dated Nov. 30, 2006 and retrieved from the Internet Archive ("Nintendo webpage").
Jul. 26, 2022 (EP)—Extended European Search Report—App. No. 22169770.9.
United States District Court Southern District of New York (Foley Square), "Complaint (w/o exhibits)", *NIKE, Inc.* v. *Lululemon Athletica Inc. et al.*, Case 1:22-cv-00082, filed Jan. 5, 2022, 29 pages.
United States District Court Southern District of New York (Foley Square), "Answer", *NIKE, Inc.* v. *Lululemon Athletica Inc. et al.*, Case 1:22-cv-00082, filed Jan. 14, 2022, 15 pages.
United States District Court Southern District of New York (Foley Square), "Docket", *NIKE, Inc.* v. *Lululemon Athletica Inc. et al.*, Case 1:22-cv-00082, printed Jul. 26, 2022, 8 pages.
Jan. 4, 2023—Petition (w/Exh. 1001 (U.S. Pat No. 10,188,930)) for Inter Partes Review of U.S. Pat. No. 10,188,930, Case No. IPR2023-00348, U.S. Patent Office, Before the Patent Trial and Appeal Board, 110 pages.
Declaration and Curriculum Vitae of Dr. Gregory S. Fischer, Jan. 4, 2023, 148 pages (Ex. 1005, IPR Pet.).
Aug. 14, 2017—Application as filed, U.S. Appl. No. 15/675,895 (Ex. 1006, IPR Pet.).
Jun. 19, 2018—Non-Final Rejection, U.S. Appl. No. 15/675,895 (Ex. 1007, IPR Pet.).
Sep. 13, 2018—Response to Non-Final Office Action and Terminal Disclaimer filed, U.S. Appl. No. 15/675,895 (Ex. 1008, IPR Pet.).
Oct. 30, 2018—Notice of Allowance, U.S. Appl. No. 15/675,895 (Ex. 1009, IPR Pet.).
Jan. 9, 2019—Issue Notification, U.S. Appl. No. 15/675,895 (Ex. 1010, IPR Pet.).
Motorola Droid Pro XT610 Description, 2 pages (Ex. 1011, IPR Pet.).
Lara Allet et al., Wearable Systems for Monitoring Mobility-Related Activities in Chronic Disease: A Systematic Review, Sensors 2010, 27 pages (Ex. 1012, IPR Pet.).
Praveen Kumar Diwakar et al., Personal Digital Exercise Trainer for Managing, Monitoring and Recording the Exercise, IEEE, Sep. 1-4, 2005, 4 pages (Ex. 1013, IPR Pet.).
Nike + iPod web page, Internet Archive waybackmachine, https://www.apple.com/ipod/nike/; 1 page (Ex. 1014, IPR Pet.).
Nike + iPod manual, 2009, 28 pages (Ex. 1015, IPR Pet.).
Gregory S. Sawicki et al., Mechanics and Energetics of Level Walking with Powered Ankle Exoskeletons, Journal of Experimental, 12 pages (Ex. 1016, IPR Pet.).
Machine Translation of Zhao Jiang hong, Liu Zhi Qiar, Shi Bin. Design and Practice for Individual Specialized PC Expert System for College Student. Journal Of Xi'An Institute of Physical Education, vol. 22 No. 2 Mar. 2005 (16 pages) <retrieved from Google Translate on Jun. 29, 2016>.
Jun. 25, 2024—Judgement, Final Written Decision, IPR2023-00348, U.S. Pat. No. 10,188,930 B2, Paper 34, 62 pages.

\* cited by examiner

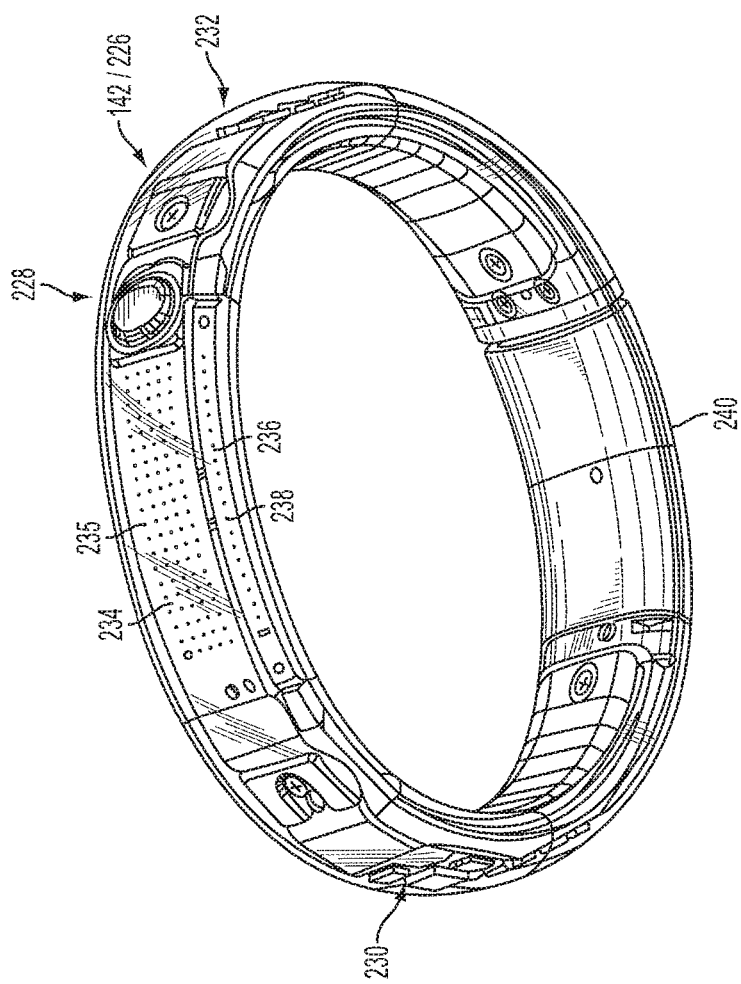
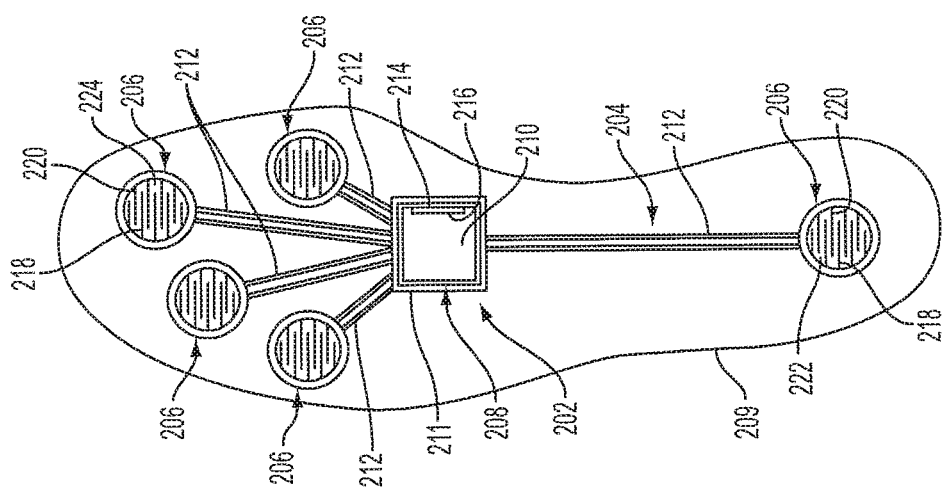
FIG. 2B
FIG. 2A

| Deep Squat | Hurdle Step | In-Line Lunge | Shoulder Mobility |
|---|---|---|---|
| Stand tall with your feet shoulder width apart and toes pointing forward. Hold a dowel in both hands and place it horizontally on top of your head so your shoulders and elbows are at a 90 degree angle (this is to make sure you are grabbing at the right width.) Press the dowel directly overhead. While maintaining an upright torso and keeping your heels down and dowel directly over your head squat as low as you can. Hold the bottom position for one count then come back up. Perform three squats. | Stand tall with your feet together and toes about an inch behind the hurdle. (the hurdle should be just below the knee cap in line with the rough area below their knee) Grab a dowel with both hands and place it behind your neck across your shoulders(the dowel is there to accentuate any movement tilting one direction or the other). While maintaining an upright posture, raise the right leg and step over the hurdle. Be sure to raise your foot toward the shin maintaining good foot alignment with the ankle, knee and hip. Touch the floor with the heel. Then bring the right foot back over the hurdle to the start position again while maintaining foot alignment with the ankle, knee, and hip. Perform three on one leg then switch legs. | Place the dowel along the spine so it touches the back of your head, your upper back and your butt. Grab the dowel overhand with the right hand which should be against the back of your neck and under hand with your left hand against your lower back. Step on to a 2x6 with a flat right foot and your heel at the end. The left heel should be placed the distance equal to the measurement from their ankle bone to their tibial tuberosity (the rough area below the knee the hurdle was in front of). Both toes should be pointing forward with feet flat one in front of the other in one line on the board. Maintaining an upright posture so the dowel stays in contact with your head, upper back and butt lower into a lunge so your right knee touches the 2x6 behind your left heel. Straighten your legs and return to the start. Perform three and then switch legs. | Before performing the test have them open their hand and get a measurement from their wrist to the end of their middle finger. "Stand tall with your feet together and arms hanging at your sides. Make a fist so your fingers are around your thumbs. In one motion place the right fist over head and down your back as far as possible while simultaneously taking your left fist up your back as far as possible. Do not "creep" your hands closer after their initial placement. |

| Active Leg Raise | Push Up | Rotary Stability | |
|---|---|---|---|
| Lay flat on your back with the back of your knees against a 2x6 with your toes pointing up. Place both arms next to your body with the palms facing up. Pull the toes of your right foot toward your shin. With the right leg remaining straight and the back of your left knee maintaining contact with the 2x6, raise your foot as high as possible. | Lie face down on the ground with your arms extended over head and your hands shoulder width apart. Pull the arms down so your thumbs are in line with (the chin first/forehead second for men and the collarbone first/chin second for women). With your legs together, pull your toes toward your shins and lift your knees and elbows off the ground getting ready to get into a push up position. While maintaining a rigid torso keeping your head, upper back and butt in one line, push your body as one unit into a push up. | "Get on your hands and knees straddling over the 2x6 so your hands are under your shoulders and your knees are under your hips. The thumbs, knees and toes must be in contact with the sides of the 2x6 and the toes must be pulled toward the shins. At the same time reach your right hand forward and your left leg backward. Then without touching down touch your right elbow to your left knee directly over the 2x6. Return to the extended position and perform 3 repetitions. If this is easy then you can progress to reach your same arm and same leg so reaching your right hand and your right leg and then touching your right elbow to your right knee without touching then reach back out to the extended position." | |

FIG. 6

PROGRAM A | SIX MONTHS

| | SCORE 1 | SCORE 2 | PHASE 1 | PHASE 2 | PHASE 3 | PHASE 4 | PHASE 5 | PHASE 6 |
|---|---|---|---|---|---|---|---|---|
| CORE STABILITY | Plank on Knees- Hold for 30s-60s | Plank- HOLD for 30s-60s | Plank w/ alt leg reach 2 SIDED | Plank w/ Alt arm reach 2 SIDED | Side Plank- HOLD 30s-60s ea 2 SIDED | Side Plank with knee bend 2 SIDED | Plank with opp arm/opp leg lift 2 SIDED | Push Up Position Row 2 SIDED |
| TWIST | Dead Bug w/ Opp Arm/Opp Leg | Quadruped Vertical | Bird Dog | Core Stability Russian Twist | Side plank w/ rotation | Plank to side plank | T stabilization | Wood Chop w/ band or dumbell |
| SQUAT | Heel Lift Body Weight Squat | Body Weight Squat | 1 1/2 Body weight Squat | Bottom Half Body Weight Squat | Iso Squat Hold w/ side to side step | Iso Squat Hold w/ alternate leg reach cross behind | OH Body Weight 1 1/2 Overhead Body Squat | Weight Squat |
| BEND | Double Hip Extension | Straight Leg Hip Extension | Hip Thigh Extension | Romanian Deadlift | Deadlift | 1 1/2 deadlift | Boot Strappers | Romanian Deadlift/Deadlift Combo |
| PUSH | Push Ups on Knees or on incline | Plank to Push Up | Push Up | Pike Push Up | Dive Bomber Push Up | Offset Push Up | SL Push Up | T Push Ups |
| PULL | Prone on Floor Is | Prone on Floor Ts | Reach, Roll and Lift | Bent Over YTs | Bent Over YTWLs | Bent Over Rows | Bent Over Single Arm Rows | Bent Over single leg one arm row |
| SINGLE LEG STANCE | Single Leg Balance with Knee lift | Single Leg Romanian Deadlift w/ kickstand | Single Leg Romanian Deadlift | Single Leg Deadlift | Single Leg Romanian Deadlift/Deadlift Combo | Partial Single Leg Squat | 1/2 Single Leg Squat | Full Range Single Leg Squat |
| LUNGE | Static Lunge | 1 1/2 range static lunge | Bottom Half Lunge | Reverse Lunge | Dynamic Forward Lunge | Dynamic Lateral Lunge | Front/Back Step Through Lunges | Lunge Matrix |
| Finisher | none | none | Leg Matrix- body weight squats, lunges, lunge jumps, squat jumps 10 reps each | Squat Thrust/ Body weight squat pyramid Up to 6 reps | Leg Matrix- body weight squats, lunges, lunge jumps, squat jumps 15 reps each | Squat Thrust/ Body weight squat pyramid Up to 8 reps | Leg Matrix- body weight squats, lunges, lunge jumps, squat jumps 20 reps each | Squat Thrust/ Body weight squat pyramid Up to 10 reps |

702, 704, 706, 708a, 708b, 708c, 708d, 708e, 708f

**If Score 0 on Push - Give 2 Pulls (whatever they scored for the Pull + the one above or below)

FIG. 7

| Tempos |
|---|
| Slow 2-1-2 down 2, hold 1, up 2 |
| Moderate 2-1-1 down 2, hold 1, up 1 |
| Normal 1-1 down 1, up 1 |
| Explosive "Looks Fast" |

FIG. 17

PROGRAM A | SIX MONTHS

| BODY MOVEMENT | SCORE 1 | SCORE 2 | PHASE 1 | PHASE 2 | PHASE 3 | PHASE 4 | PHASE 5 | PHASE 6 |
|---|---|---|---|---|---|---|---|---|
| CORE STABILITY | Low Ab Leg Lowering | Plank | Plank w/ Alt Leg Reach | Side Plank | Plank w/ Alt Arm Reach | Side Plank with Rotation | Quadruped Row | Renegade Row |
| TWIST | Dead Bug w/ Opp Arm/Opp Leg | Standing Rotary Stability | Horse Stance Vertical | Bird Dog | Rotary Stability- Same Arm Same Leg | Plank to Side Plank | T Stabilization | Seated Russian Twist |
| SQUAT | Heel Lift Body Weight Squat | Body Weight Squat | 1 1/2 Body Weight Squat | Bottom Half Body Weight Squat | Iso Squat Hold w/ Side to Side Step | Iso Squat Hold w/ Alt Leg Reach | OH Body Weight Squat | 1 1/2 Overhead Body Weight Squat |
| BEND | Double Hip Extension | Straight Leg Hip Extension | Hip Thigh Extension | Romanian Deadlift | Deadlift | 1 1/2 Deadlift | Bottom 1/2 Deadlift | Romanian Deadlift/Deadlift Combo |
| PUSH | T Stabilization | Plank to Push Up | Push Up | Pike Push Up | Hands at Forehead Push Up | Offset Push Up | SL Push Up | T Push Ups |
| PULL | Reach Roll n'Lift | Lying T's | Prone Cobra | Bent Over T's | Bent Over YTWL's | Bent Over Row | Bent Over Single Arm Row | 1 Leg Single Arm Row |
| SINGLE LEG BALANCE | Single Leg Balance w/ Knee Lift | Single Leg Romanian Deadlift w/ Kickstand | Single Leg Romanian Deadlift | Single Leg Deadlift | Single Leg Romanian Deadlift/Deadlift Combo | Partial Single Leg Squat | 1/2 Single Leg Squat | Full Range Single Leg Squat |
| LUNGE | Static Lunge | 1 1/2 Range Static Lunge | Bottom Half Lunge | Reverse Lunge | Dynamic Forward Lunge | Static Lateral Lunge | Dynamic Lateral Lunge | Matrix Lunge |

FIG. 20

BASELINE | WORKOUT A

| EXERCISE LIST | WORKOUT PHASE | HMS RELATIONSHIP | PHASE DETAILS |
|---|---|---|
| ROTATE 1-6 | DYNAMIC WARM-UP (DWU) | NA | 6 DIFFERENT DYNAMIC WARM-UP ROUTINES: ROTATE EACH WORKOUT |
| EXERCISE 1A | CORE STABILITY | 1 SET A | 1 SET B |
| EXERCISE 1B | TWIST | |
| EXERCISE 2A | SQUAT | 1 SET A | 1 SET B |
| EXERCISE 2B | PULL | |
| EXERCISE 3A | SINGLE LEG BALANCE | 1 SET A | 1 SET B |
| EXERCISE 3B | PUSH | |
| EXERCISE 4A | BEND | 1 SET A | 1 SET B |
| EXERCISE 4B | LUNGE | |
| HMS 14 (+) | METABOLIC | 1-2 SETS |
| 1-3 EXERCISES | REGENERATION | 1-3 MOVES BASED ON TIME AND TOTAL HMS SCORE |

FIG. 21

MONTH 1-2 | WORKOUT A

| EXERCISE LIST | WORKOUT PHASE | HMS RELATIONSHIP | PHASE DETAILS |
|---|---|---|
| ROTATE 1-6 | DYNAMIC WARM-UP (DWU) | NA | 6 DIFFERENT DYNAMIC WARM-UP ROUTINES: ROTATE EACH WORKOUT (APPROXIMATELY 10 MINUTES TOTAL AND COULD BE USED FOR A QUICK START ROUTINE) |
| EXERCISE 1A | CORE STABILITY | ROTARY STABILITY | ROTATE 1 SET A | 1 SET B (REPEAT FOR MULTIPLE SETS) |
| EXERCISE 1B | TWIST | ROTARY STABILITY | |
| EXERCISE 2A | SQUAT | OVERHEAD SQUAT | ROTATE 1 SET A | 1 SET B (REPEAT FOR MULTIPLE SETS) |
| EXERCISE 2B | PULL | SHOULDER STABILITY | |
| EXERCISE 3A | SINGLE LEG BALANCE | HURDLE STEP | ROTATE 1 SET A | 1 SET B (REPEAT FOR MULTIPLE SETS) |
| EXERCISE 3B | PUSH | PUSH UP | |
| EXERCISE 4A | BEND | ACTIVE LEG RAISE | ROTATE 1 SET A | 1 SET B (REPEAT FOR MULTIPLE SETS) |
| EXERCISE 4B | LUNGE | IN-LINE LUNGE | |
| HMS 14 (+) | METABOLIC | 1-2 SETS |
| 1-3 EXERCISES | REGENERATION | 1-3 MOVES BASED ON TIME AND TOTAL HMS SCORE |

Groupings:
- SOME CORRECTIVE MOVEMENTS: Dynamic Warm-Up
- CORRECTIVE & CORE: Exercises 1A, 1B
- STRENGTH & POWER: Exercises 2A–4B
- WORKOUT B CARDIO & METABOLIC: HMS 14 (+)
- WORKOUT C REGENERATION: 1-3 Exercises

FIG. 22

MONTH 3-4 | WORKOUT A

| EXERCISE LIST | WORKOUT PHASE \| HMS RELATIONSHIP | PHASE DETAILS | |
|---|---|---|---|
| ROTATE 1-6 | DYNAMIC WARM-UP (DWU) \| NA | 6 DIFFERENT DYNAMIC WARM-UP ROUTINES: ROTATE EACH WORKOUT | SOME CORRECTIVE MOVEMENTS |
| EXERCISE 1A | CORE STABILITY \| ROTARY STABILITY | 1 SET A \| 1 SET B | CORRECTIVE & CORE |
| EXERCISE 1B | TWIST \| ROTARY STABILITY | | |
| EXERCISE 2A | SQUAT \| OVERHEAD SQUAT | 1 SET A \| 1 SET B \| 1 SET C | STRENGTH & POWER |
| EXERCISE 2B | PULL \| SHOULDER STABILITY | | |
| EXERCISE 2C | SINGLE LEG BALANCE \| HURDLE STEP | | |
| EXERCISE 3A | PUSH \| PUSH UP | 1 SET A \| 1 SET B \| 1 SET C | WORKOUT B CARDIO & METABOLIC |
| EXERCISE 3B | BEND \| ACTIVE LEG RAISE | | |
| EXERCISE 3C | LUNGE \| IN-LINE LUNGE | | |
| HMS 14 (+) | METABOLIC | 1-2 SETS | |
| 1-3 EXERCISES | REGENERATION | 1-3 MOVES BASED ON TIME AND TOTAL HMS SCORE | WORKOUT C REGENERATION |

FIG. 23

MONTH 5-6 | WORKOUT A

| EXERCISE LIST | WORKOUT PHASE | HMS RELATIONSHIP | PHASE DETAILS | |
|---|---|---|---|
| ROTATE 1-6 | DYNAMIC WARM-UP (DWU) | NA | 6 DIFFERENT DYNAMIC WARM-UP ROUTINES: ROTATE EACH WORKOUT | SOME CORRECTIVE MOVEMENTS |
| EXERCISE 1A | CORE STABILITY | ROTARY STABILITY | 1 SET A | 1 SET B | 1 SET C | 1 SET D | CORRECTIVE & CORE |
| EXERCISE 1B | TWIST | ROTARY STABILITY | | |
| EXERCISE 1C | SQUAT | OVERHEAD SQUAT | | |
| EXERCISE 1D | PULL | SHOULDER STABILITY | | |
| EXERCISE 2A | SINGLE LEG BALANCE | HURDLE STEP | 1 SET A | 1 SET B | 1 SET C | 1 SET D | STRENGTH & POWER |
| EXERCISE 2B | PUSH | PUSH UP | | |
| EXERCISE 2C | BEND | ACTIVE LEG RAISE | | |
| EXERCISE 2D | LUNGE | IN-LINE LUNGE | | |
| HMS 14 (+) | METABOLIC | 1-2 SETS | WORKOUT B CARDIO & METABOLIC |
| 1-3 EXERCISES | REGENERATION | 1-3 MOVES BASED ON TIME AND TOTAL HMS SCORE | WORKOUT C REGENERATION |

FIG. 24

Workout B | Metabolic

| TYPE OF METABOLIC EXERCISE | MONTH 1 | MONTH 2 | MONTH 3 | MONTH 4 | MONTH 5 | MONTH 6 |
|---|---|---|---|---|---|---|
| LOCOMOTION | Hop Scotch | Run | Rope Jumping | Lateral Ski Jump | Over/Under | High Knee Run |
| CHANGE OF LEVELS | Body Weight Squat | Body Weight Jump Squat | Body Weight Jump Squat w/ Reach | Squat In & Out Jumps | Explosive Jumps | Lunge Jumps |
| CORE | Mountain Climber | Prone Cross Toe Touch | Spiderman | Squat Thrusts | Squat Thrusts w/ Jump | Single Leg Squat Thrusts |
| AGILITY/SKILL | In Place | Front to Back | Side to Side | Moving Front to Back & Side to Side | Chaos Drills | Chaos Drills |

FIG. 25

B | SETS | WORK | REST

| S\|W\|R BY MONTH | MONTH 1 | MONTH 2 | MONTH 3 | MONTH 4 | MONTH 5 | MONTH 6 |
|---|---|---|---|---|---|---|
| SETS | 2-3 | 2-3 | 2-3 | 2-3 | 2-3 | 2-3 |
| WORK | 20 S | 30 S | 30 S | 45 S | 45 S | 60 S |
| REST | 20 S | 30 S | 20 S | 30 S | 20 S | 30 S |

FIG. 26

Month 1 | Workout B

| EXERCISE LIST | WORKOUT PHASE | PHASE DETAILS |
|---|---|---|
| Rotate 1 - 6 | DWU | ROTATE |
| Exercise 1A | LOCOMOTION | CIRCUIT OF 4 \| 20 S WORK \| 20 S REST |
| Exercise 1B | CHANGE OF LEVELS | |
| Exercise 1C | CORE | |
| Exercise 1D | AGILITY/SKILL | |
| REST | 3 MINUTES | REPEAT X 1 |

FIG. 27

Month 2 | Workout B

| EXERCISE LIST | WORKOUT PHASE | PHASE DETAILS |
|---|---|---|
| Rotate 1 - 6 | DWU | ROTATE |
| Exercise 1A | LOCOMOTION | CIRCUIT OF 4 \| 30 S WORK \| 30 S REST |
| Exercise 1B | CHANGE OF LEVELS | |
| Exercise 1C | CORE | |
| Exercise 1D | AGILITY/SKILL | |
| REST | 3 MINUTES | REPEAT X 1 |

FIG. 28

Month 3 | Workout B

| EXERCISE LIST | WORKOUT PHASE | PHASE DETAILS |
|---|---|---|
| Rotate 1 - 6 | DWU | ROTATE |
| Exercise 1A | LOCOMOTION | CIRCUIT OF 8 | 30 S WORK | 20 S REST |
| Exercise 1B | CHANGE OF LEVELS | |
| Exercise 1C | CORE | |
| Exercise 1D | AGILITY/SKILL | |
| Exercise 1E | LOCOMOTION | |
| Exercise 1F | CHANGE OF LEVELS | |
| Exercise 1G | CORE | |
| Exercise 1H | AGILITY/SKILL | |
| REST | 3 MINUTES | REPEAT X 1 |

FIG. 29

Month 4 | Workout B

| EXERCISE LIST | WORKOUT PHASE | PHASE DETAILS |
|---|---|---|
| Rotate 1 - 6 | DWU | ROTATE |
| Exercise 1A | LOCOMOTION | CIRCUIT OF 4 \| 45 S WORK \| 30 S REST |
| Exercise 1B | CHANGE OF LEVELS | |
| Exercise 1C | CORE | |
| Exercise 1D | AGILITY/SKILL | |
| REST | 3 MINUTES | REPEAT X 1 |

FIG. 30

Month 5 | Workout B

| EXERCISE LIST | WORKOUT PHASE | PHASE DETAILS |
|---|---|---|
| Rotate 1 - 6 | DWU | ROTATE |
| Exercise 1A | LOCOMOTION | CIRCUIT OF 8 | 45 S WORK | 20 S REST |
| Exercise 1B | CHANGE OF LEVELS | |
| Exercise 1C | CORE | |
| Exercise 1D | AGILITY/SKILL | |
| Exercise 1E | LOCOMOTION | |
| Exercise 1F | CHANGE OF LEVELS | |
| Exercise 1G | CORE | |
| Exercise 1H | AGILITY/SKILL | |
| REST | 3 MINUTES | REPEAT X 1 |

FIG. 31

Month 6 | Workout B

| EXERCISE LIST | WORKOUT PHASE | PHASE DETAILS |
|---|---|---|
| Rotate 1 - 6 | DWU | ROTATE |
| Exercise 1A | LOCOMOTION | |
| Exercise 1B | CHANGE OF LEVELS | |
| Exercise 1C | CORE | |
| Exercise 1D | AGILITY/SKILL | CIRCUIT OF 4 \| 60 S WORK \| 30 S REST |
| Exercise 1E | LOCOMOTION | |
| Exercise 1F | CHANGE OF LEVELS | |
| Exercise 1G | CORE | |
| Exercise 1H | AGILITY/SKILL | |
| REST | 3 MINUTES | REPEAT X 1 |

FIG. 32

Workout C | REGENERATION

| Exercise | BODY REGENERATION 1 | BODY REGENERATION 2 | BODY REGENERATION 3 |
|---|---|---|---|
| 1 | Foam Roll/Stick, Ball 2 Stations | Foam Roll/Stick, Ball SMR 2 Stations | Foam Roll/Stick, Ball SMR 2 Stations |
| 2 | Post Chain, Floor 90-90 | 2 Way HS Stretch | 1/2 Kneel Hip Flexor w/ Arm Slides |
| 3 | 3 Way Hip Flexor w/ Quad Out | 1/2 Kneel Hip Flexor, Hands Behind Head | Quadruped w/ T/S Rot/Ext |
| 4 | UT, Lat | Lev Scap, Wall Pec Minor Stretch | SL Wall Ankle Mobility |
| 5 | 1A SL Ankle Mobility | 1A 1/2 Kneel Hip Flexor w/ Ankle Mob | 1A 1/2 Kneel Hip Flexor w/ BB Twist/ Tilt |
| 6 | 2A Toe Touch Progression | 2A Quadruped T/S Rot, Ext | 2A OH Reach and Toe Touch |
| 7 | 3A Wall Slides | 3A Forearm Wall Slides | 3A Floor Dyn Blackburns |
| 8 | 1B 1/2 Kneel Hip FLexor w/ T/S Ext Rot | 4A Wave Squat | 4A Squat to Stand |
| 9 | 2B Horizontal Horse Stance | 1B Supine Knee Fall-Ins | 1B Supine Knee Int Iso hold |
| 10 | 3B Squat to Post Chain Stretch | 2B Sleeper Stretch | 2B Supine Floor Slides |

FIG. 33

C | SETS | WORK | REST

| S/W/T BY MONTH | MONTH 1 | MONTH 2 | MONTH 3 | MONTH 4 | MONTH 5 | MONTH 6 |
|---|---|---|---|---|---|---|
| SETS | 1 | 1 | 1 | 1 | 1 | 1 |
| WORK | 60 S | 60 S | 60 S | 60 S | 60 S | 60 S |
| TRANSITION | 30 S | 30 S | 30 S | 30 S | 30 S | 30 S |

FIG. 34

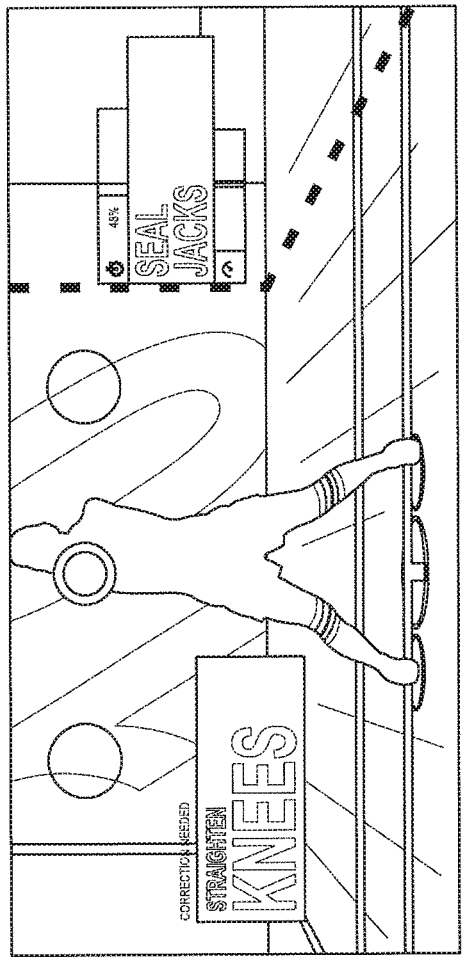
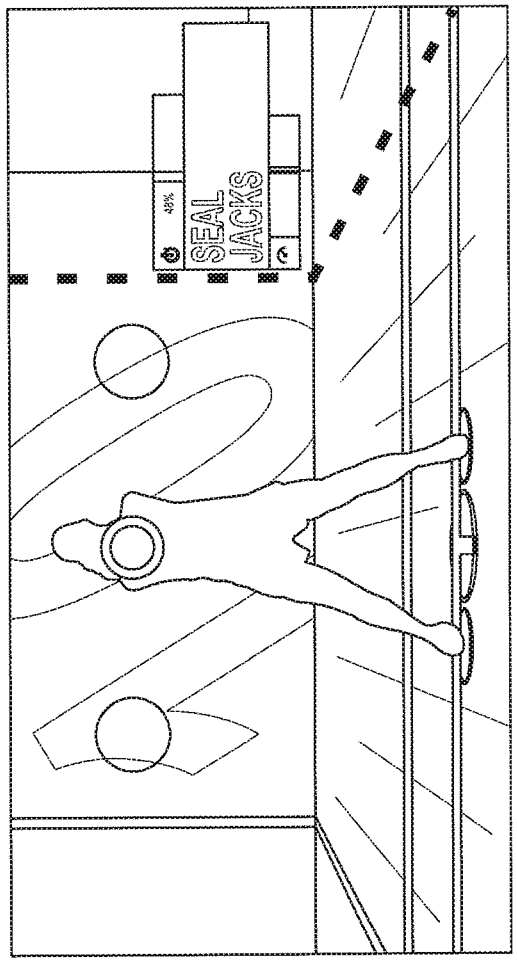
FIG. 43A
FIG. 43B

| KEY TRIGGERS | ADJUSTMENT | HOW TO ADDRESS |
|---|---|---|
| 1ST rep same as Last | W1: add reps<br>W2: add set<br>W3: add set + reps<br>W4: max set + reps | W1: instructional, technique<br>W2: few corrections, reminders<br>W3: push them, more motivation<br>W4: max push, pure motivation |
| 1st rep better than as last | W1<br>W2<br>W3<br>W4 | |
| 1st rep worse then last | W1<br>W2<br>W3<br>W4 | |
| Multiple reps in Red Zone | W1<br>W2<br>W3<br>W4 | |

FIG. 48

DROP-IN SESSION DURATION SELECTION

METHOD AND SYSTEM FOR AUTOMATED PERSONAL TRAINING THAT INCLUDES TRAINING PROGRAMS

CROSS REFERENCE TO RELATED APPLICATIONS

This application is a continuation of U.S. patent application Ser. No. 15/255,566, filed Sep. 2, 2016, which is a continuation of U.S. patent application Ser. No. 13/304,064, filed Nov. 23, 2011, now U.S. Pat. No. 9,457,256, which is a continuation-in-part of U.S. patent application Ser. No. 13/290,359, filed Nov. 7, 2011, now U.S. Pat. No. 9,283,429, which claims the benefit of, and priority to, U.S. Provisional Patent Application Nos. 61/410,777 filed Nov. 5, 2010, 61/417,102 filed Nov. 24, 2010, 61/422,511 filed Dec. 13, 2010, 61/432,472 filed Jan. 13, 2011, and 61/433,792 filed Jan. 18, 2011, each of which is entitled "Method and System for Automated Personal Training." The content of each of the applications is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this separation between athletic activity and other activities reduces the amount of motivation that an individual might have toward exercising. Further, athletic activity services and systems directed toward encouraging individuals to engage in athletic activities might also be too focused on one or more particular activities while an individual's interests are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the invention provide systems and methods for creating personalized exercise programs. A computer device, such as a video game console may be used with an image capture device, such as a group of cameras to capture images of a user performing athletic movements. As used herein, an "athletic movement" includes movements relating to fitness, exercise, flexibility, including movements that may be part of one or more single and multiple participant athletic competitions, exercise routines, and/or combinations thereof. The images may then be evaluated to create a human movement screen score. The human movement screen score may be used to create a personalized exercise program tailored to the specific user. A human movement screen (HMS) is a ranking and grading system that documents movement patterns that may be key to normal function. The functional movement screen (FMS) developed by Gray Cook is an example of a human movement screen.

In some embodiments the user may also provide preference data, such as data relating to time commitments, preferred exercises and a preferred number of exercise sessions in a predetermined time period. The computer device may consider these factors when creating a personalized exercise program.

Certain other embodiments may capture athletic movement data with accelerometers, gyroscopes or position locating devices, such as GPS devices.

In other embodiments, the present invention can be partially or wholly implemented on a tangible non-transitory computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments.

FIGS. 2A-B illustrate example sensor assemblies that may be worn by a user in accordance with example embodiments.

FIG. 6 shows exemplary instructions that may be provided to a user to perform the athletic movement.

FIG. 7 illustrates exemplary personalized exercise program phases in accordance with an embodiment of the invention.

FIG. 17 provides an example of different tempos at which a same drill can be performed.

FIG. 20-34 illustrates an example six month workout plan that may include a baseline workout and six month long programs.

FIGS. 43A-B illustrate example graphical user interfaces providing a user with feedback on their form and removing the corrective feedback when the user's form improves.

FIGS. 46-49 illustrate examples of revising a workout session based on the amount of time a user can commit to a workout.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
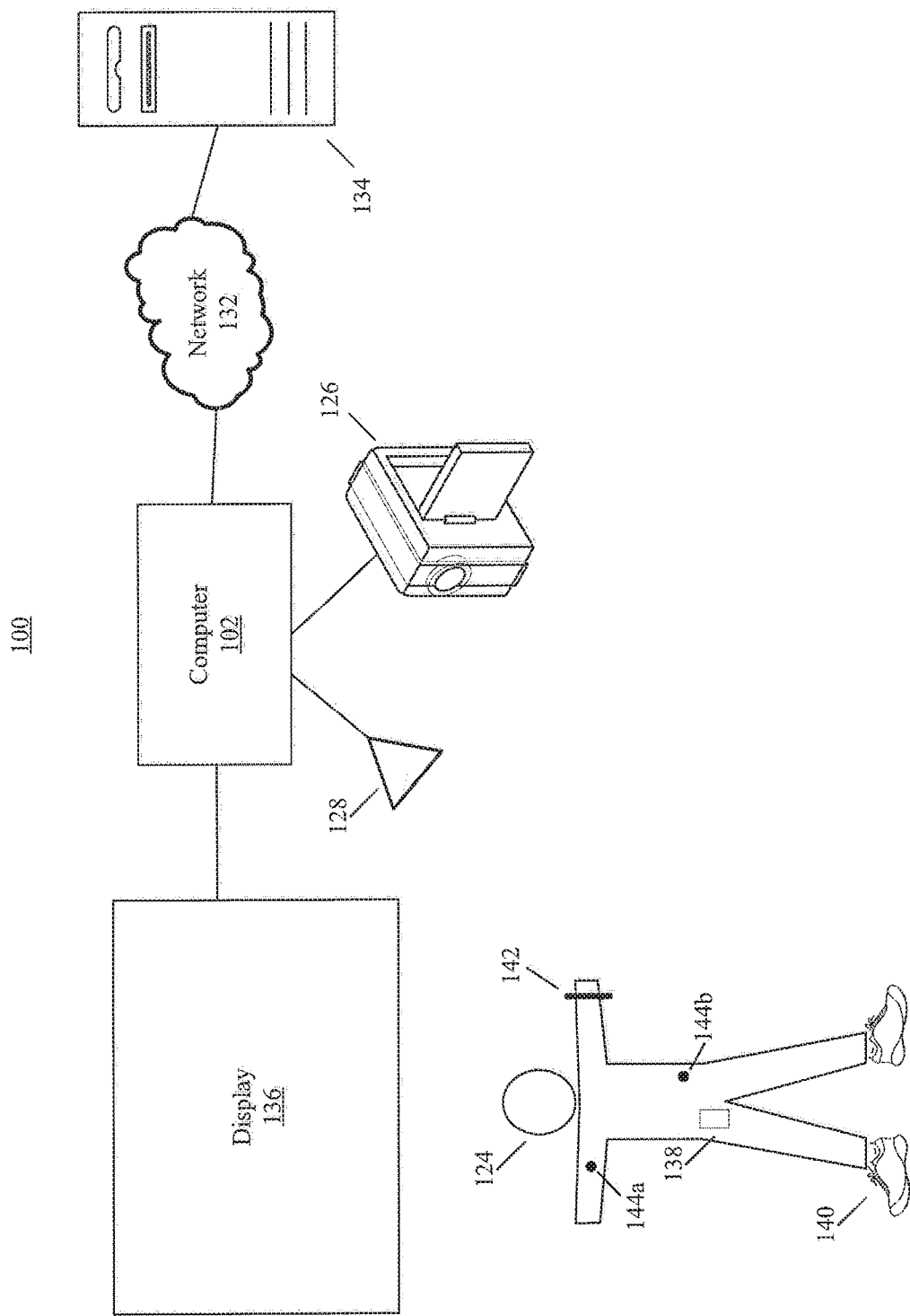

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
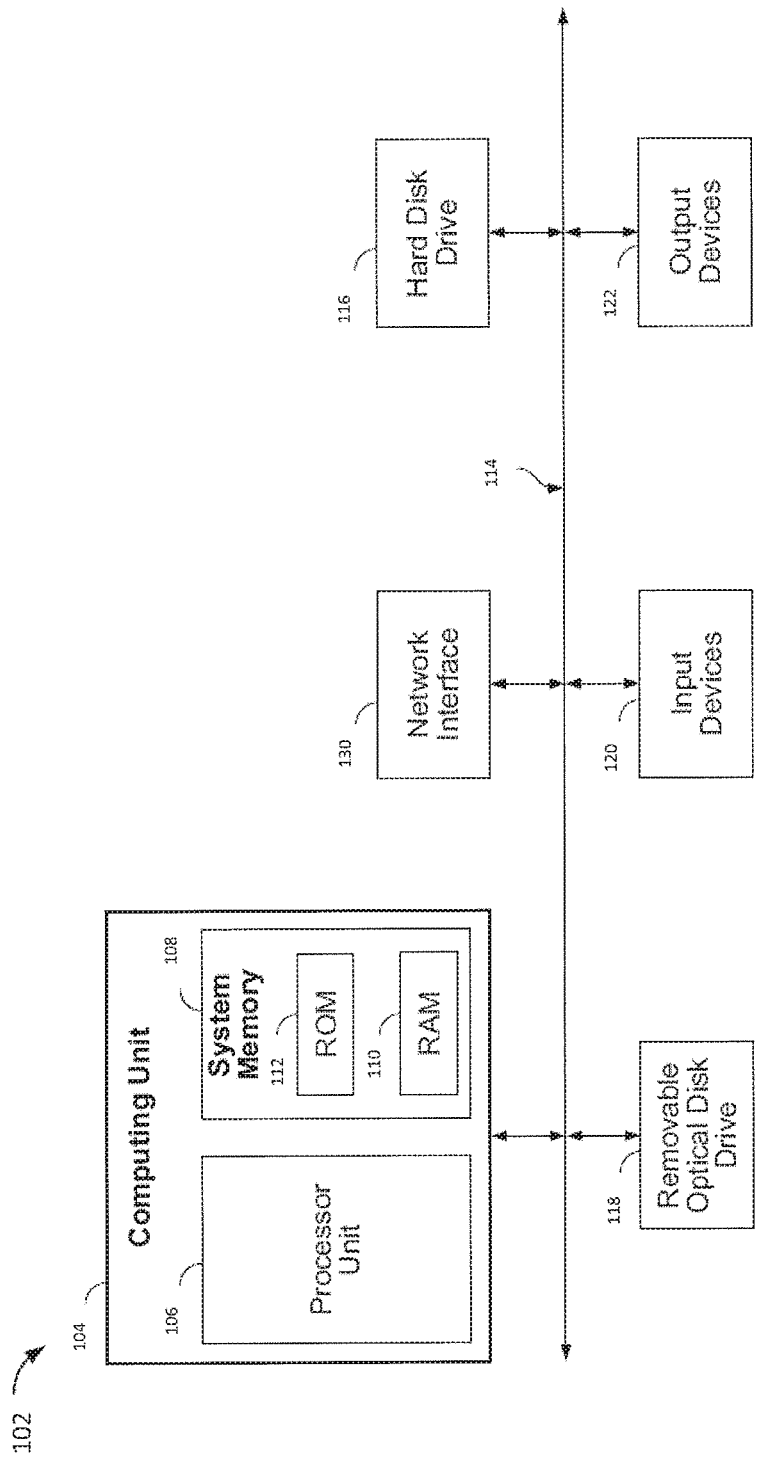

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card, as well as to input devices 120, and output devices 122. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained image-capturing device 126 or sensor 128 may directly detect athletic movements, such that the data obtained from image-capturing device 126 or sensor 128 is directly correlated to a motion parameter. For example, and with reference to FIG. 4, image data from image-capturing device 126 may detect that the distance between sensor locations 402g and 402i has decreased and therefore, image-capturing device 126 alone may be configured to detect that user's 124 right arm has moved. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Still further, computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topography(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128, may include but not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oregon Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, California or Zune® or Microsoft® Windows devices available from Microsoft of Redmond, Washington As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144a-b. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may communicate through computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one exemplary embodiment of an example sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 and/or 224 disposed between the electrodes 218, 220 to electrically connect the electrodes 218, 220 together. When pressure is applied to the force-sensitive material 222/224, the resistivity and/or conductivity of the force-sensitive material 222/224 changes, which changes the electrical potential between the electrodes 218, 220. The change in resistance can be detected by the sensor system 202 to detect the force applied on the sensor 216. The force-sensitive resistive material 222/224 may change its resistance under pressure in a variety of ways. For example, the force-sensitive material 222/224 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222/224 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 and/or the surface resistance between a conducting layer (e.g. carbon/graphite) and a force-sensitive layer (e.g. a semiconductor) of a multi-layer material 222/224. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222/224, as defined herein, may be or include a doped or non-doped semiconducting material.

The electrodes 218, 220 of the FSR sensor 206 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead(s) 212 may be formed of a single piece of the same material 222/224. In further embodiments, material 222 is configured to have at least one electric property (e.g., conductivity, resistance, etc.) than material 224. Examples of exemplary sensors are disclosed in U.S. patent application Ser. No. 12/483,824, filed on Jun. 12, 2009, the contents of which are incorporated herein in their entirety for any and all non-limiting purposes.

ii. Wrist-Worn Device

As shown in FIG. 2B, device 226 (which may be, or be a duplicative of or resemble sensory device 142 shown in FIG. 1A) may be configured to be worn by user 124, such as around a wrist, arm, ankle or the like. Device 226 may monitor movements of a user, including, e.g., athletic movements or other activity of user 124. For example, in one embodiment, device 226 may be activity monitor that measures, monitors, tracks or otherwise senses the user's activity (or inactivity) regardless of the user's proximity or interactions with computer 102. Device 226 may detect athletic movement or other activity (or inactivity) during user's 124 interactions with computer 102 and/or operate independently of computer 102. Device 226 may communicate directly or indirectly, wired or wirelessly, with network 132 and/or other devices, such as devices 138 and/or 140. Athletic data obtained from device 226 may be utilized in determinations conducted by computer 102, such as determinations relating to which exercise programs are presented to user 124. As used herein, athletic data means data regarding or relating to a user's activity (or inactivity). In one embodiment, device 226 may wirelessly interact with a remote website such as a site dedicated to fitness or health related subject matter, either directly or indirectly (e.g., via a mobile device, such as device 138 associated with user 124). In this or another embodiment, device 226 may interact with a mobile device, such as device 138, as to an application dedicated to fitness or health related subject matter. In these or other embodiments, device 226 may interest with both a mobile device as to an application as above, such as device 138, and a remote website, such as a site dedicated to fitness or health related subject matter, either directly or indirectly (e.g., via the mobile device, such as device 138). In some embodiments, at some predetermined time(s), the user may wish to transfer data from the device 226 to another location. For example, a user may wish to upload data from a portable device with a relatively smaller memory to a larger device with a larger quantity of memory. Communication between device 226 and other devices may be done wirelessly and/or through wired mechanisms.

As shown in FIG. 2B, device 226 may include an input mechanism, such as a button 228, to assist in operation of the device 226. The button 228 may be a depressible input operably connected to a controller 230 and/or any other electronic components, such as one or more elements of the type(s) discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system 236 may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140, and/or recharging an internal power source.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), a gyroscope, a location-determining device (e.g., GPS), light sensor, temperature sensor (including ambient temperature and/or body temperature), heart rate monitor, image-capturing sensor, moisture sensor and/or combinations thereof. Detected movements or parameters from device's 142 sensor(s), may include (or be used to form) a variety of different parameters, metrics or physiological characteristics including but not limited to speed, distance, steps taken, and energy expenditure such as calories, heart rate and sweat detection. Such parameters may also be expressed in terms of activity points or currency earned by the user based on the activity of the user. Examples of wrist-worn sensors that may be utilized in accordance with various embodiments are disclosed in U.S. patent application Ser. No. 13/287,064, filed on Nov. 1, 2011, the contents of which are incorporated herein in their entirety for any and all non-limiting purposes.

iii. Identify Sensory Locations

The system 100 may process sensory data to identify user movement data. In one embodiment, sensory locations may be identified. For example, images of recorded video, such as from image-capturing device 126, may be utilized in an identification of user movement. For example, the user may stand a certain distance, which may or may not be predefined, from the image-capturing device 126, and computer 102 may process the images to identify the user 124 within the video, for example, using disparity mapping techniques. In an example, the image capturing device 126 may be a stereo camera having two or more lenses that are spatially offset from one another and that simultaneously capture two or more images of the user. Computer 102 may process the two or more images taken at a same time instant to generate a disparity map for determining a location of certain parts of the user's body in each image (or at least some of the images) in the video using a coordinate system (e.g., Cartesian coordinates). The disparity map may indicate a difference between an image taken by each of the offset lenses.

Figure 3:
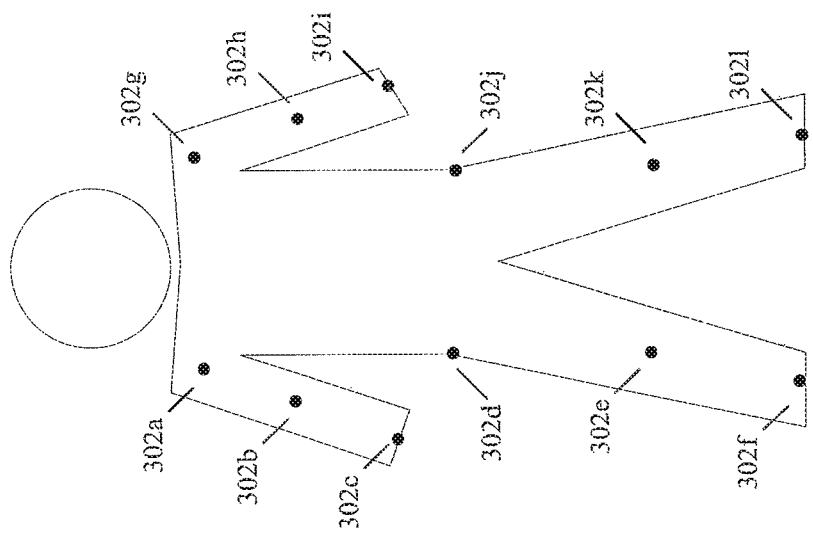
FIG. 3 illustrates example points on a user's body to monitor in accordance with example embodiments.

In a second example, one or more sensors may be located on or proximate to the user's 124 body at various locations or wear a suit having sensors situated at various locations. Yet, in other embodiments, sensor locations may be determined from other sensory devices, such as devices 138, 140, 142 and/or 144. With reference to FIG. 3, sensors may be placed (or associated with, such as with image-capturing device 126) body movement regions, such as joints (e.g., ankles, elbows, shoulders, etc.) or at other locations of interest on the user's 124 body. Example sensory locations are denoted in FIG. 3 by locations 302a-302o. In this regard, sensors may be physical sensors located on/in a user's clothing, yet in other embodiments, sensor locations 302a-302o may be based upon identification of relationships between two moving body parts. For example, sensor location 302a may be determined by identifying motions of user 124 with an image-capturing device, such as image-capturing device 126. Thus, in certain embodiments, a sensor may not physically be located at a specific location (such as sensor locations 302a-302o), but is configured to sense properties of that location, such as with image-capturing device 126. In this regard, the overall shape or portion of a user's body may permit identification of certain body parts. Regardless of whether an image-capturing device, such as camera 126, is utilized and/or a physical sensor located on the user 124, such as sensors within or separate from one or more of device(s) 138, 140, 142, 144 are utilized, the sensors may sense a current location of a body part and/or track movement of the body part. In one embodiment, location 302m may be utilized in a determination of the user's center of gravity (a.k.a, center of mass). For example, relationships between location 302a and location(s) 302f/302l with respect to one or more of location(s) 302m-302o may be utilized to determine if a user's center of gravity has been elevated along the vertical axis (such as during a jump) or if a user is attempting to "fake" a jump by bending and flexing their knees. In one embodiment, sensor location 302n may be located at about the sternum of user 124. Likewise, sensor location 302o may be located approximate to the naval of user 124. In certain embodiments, data from sensor locations 302m-302o may be utilized (alone or in combination with other data) to determine the center of gravity for user 124. In further embodiments, relationships between multiple several sensor locations, such as sensors 302m-302o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 302m-302o may serve as a point for a center of moment location of user 124. In another embodiment, one or more locations may serve as a center of moment of specific body parts or regions.

In certain embodiments, a time stamp to the data collected indicating a specific time when a body part was at a certain location. Sensor data may be received at computer 102 (or other device) via wireless or wired transmission. A computer, such as computer 102 and/or devices 138, 140, 142, 144 may process the time stamps to determine the locations of the body parts using a coordinate system (e.g., Cartesian coordinates) within each (or at least some) of the images in the video. Data received from image-capturing device 126 may be corrected, modified, and/or combined with data received from one or more other devices 138, 140, 142 and 144.

In a third example, computer 102 may use infrared pattern recognition to detect user movement and locations of body parts of the user 124. For example, the sensor 128 may include an infrared transceiver, which may be part of image-capturing device 126, or another device, that may emit an infrared signal to illuminate the user's 124 body using infrared signals. The infrared transceiver 128 may capture a reflection of the infrared signal from the body of user 124. Based on the reflection, computer 102 may identify a location of certain parts of the user's body using a coordinate system (e.g., Cartesian coordinates) at particular instances in time. Which and how body parts are identified may be predetermined based on a type of exercise a user is requested to perform.

Figure 4:
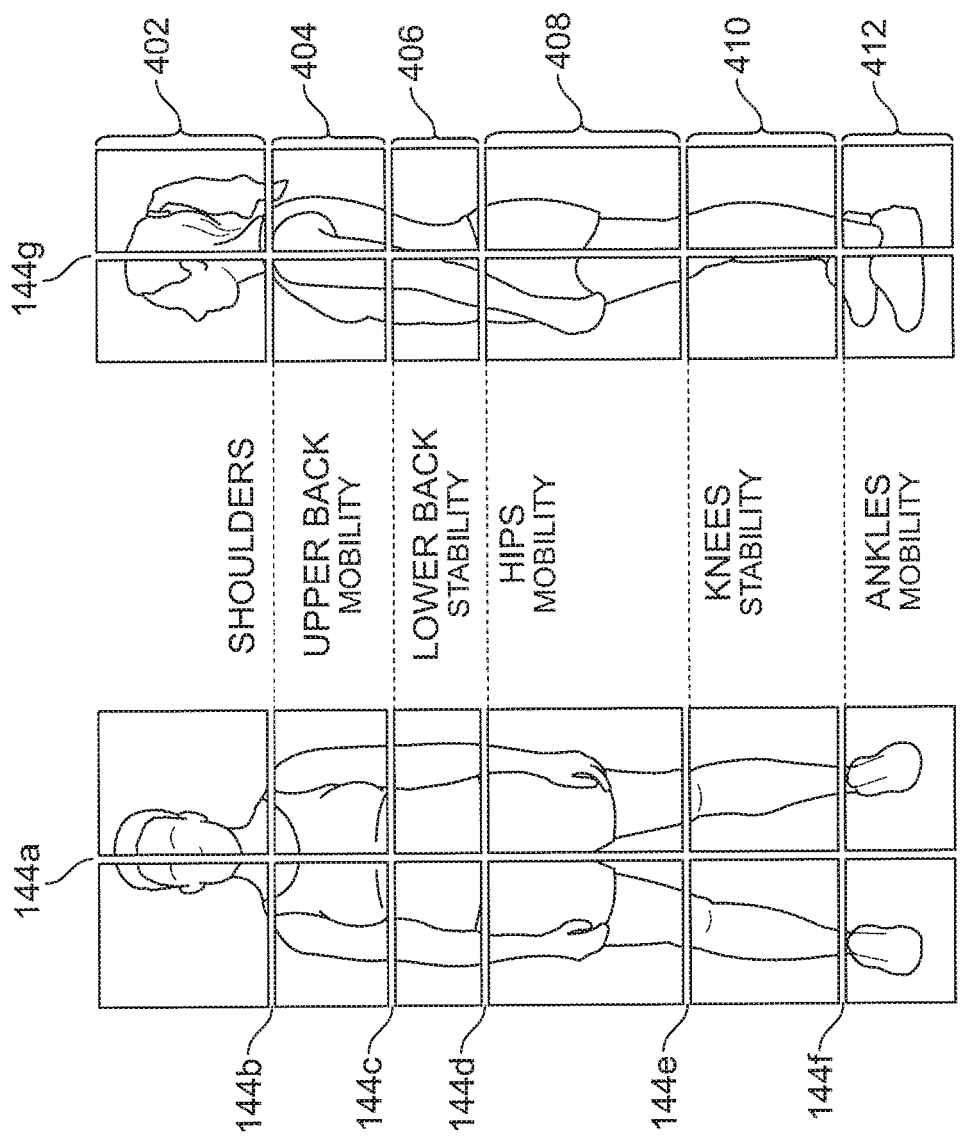
FIG. 4 illustrates an example posture assessment in accordance with example embodiments.

As part of a workout routine, computer 102 may make an initial postural assessment of the user 124 as part of the initial user assessment. With reference to FIG. 4, computer 102 may analyze front and side images of a user 124 to determine a location of one or more of a user's shoulders, upper back, lower back, hips, knees, and ankles. On-body sensors and/or infrared techniques may also be used, either alone or in conjunction with image-capturing device 126, to determine the locations of various body parts for the postural assessment. For example, computer 102 may determine assessment lines 124a-g to determine the locations of a various points on a user's body, such as, for example, ankles, knees, hips, upper back, lower back, and shoulders.

3. Identify Sensory Regions

In further embodiments, system 100 may identify sensor regions. In one embodiment, assessments lines 144a-g may be utilized to divide the user's body into regions. For example, lines 144b-f may be horizontal axes. For example, a "shoulders" region 402 may correlate to a body portion having a lower boundary around the user's shoulders (see line 144b), region 404 may correlate to the body portion between the shoulders (line 144b) and about half the distance to the hips (see line 144c) and thus be an "upper back" region, and region 406 may span the area between line 144c to the hips (see line 144d) to comprise a "lower back region." Similarly, region 408 may span the area between the "hips" (line 144d) and the "knees" (see line 144e), region 410 may span between lines 144e and 144f and region 412 (see "ankles") may have an upper boundary around line 144f. Regions 402-412 may be further divided, such as into quadrants, such as by using axes 144a and 144g 4. Categorize Locations or Regions Regardless of whether specific points (e.g., locations shown in FIG. 3) and/or regions (e.g. regions shown in FIG. 4), body parts or regions that are not proximate to each other may nonetheless be categorized into the same movement category (see, e.g. block 302c). For example, as shown in FIG. 4, the "upper back", "hips", and "ankles" regions 404, 408,412 may be categorized as belonging to a "mobility" category. In another embodiment, the "lower back" and "knees" regions 406, 410 may be categorized as belonging to a "stability" category. The categorizations are merely examples, and in other embodiments, a location or region may belong to multiple categories. For example, a "center of gravity" region may be formed from regions 404 and 406. In one embodiment, a "center of gravity" may comprise portions of regions 404 and 406. IN another embodiment, a "center of moment" category may be provided, either independently, or alternatively, as comprising a portion of at least another category. In one embodiment, a single location may be weighted in two or more categories, such as being 10% weighted in a "stability" category and 90% weighted in a "mobility" category.

Computer 102 may also process the image to determine a color of clothing of the user or other distinguishing features to differentiate the user from their surroundings. After processing, computer 102 may identify a location of multiple points on the user's body and track locations of those points, such as locations 302 in FIG. 3. Computer 102 may also prompt the user to answer questions to supplement the postural assessment, such as, for example, age, weight, etc.

II. Creation of Personal Training Programs

A. Overview

Figure 5:
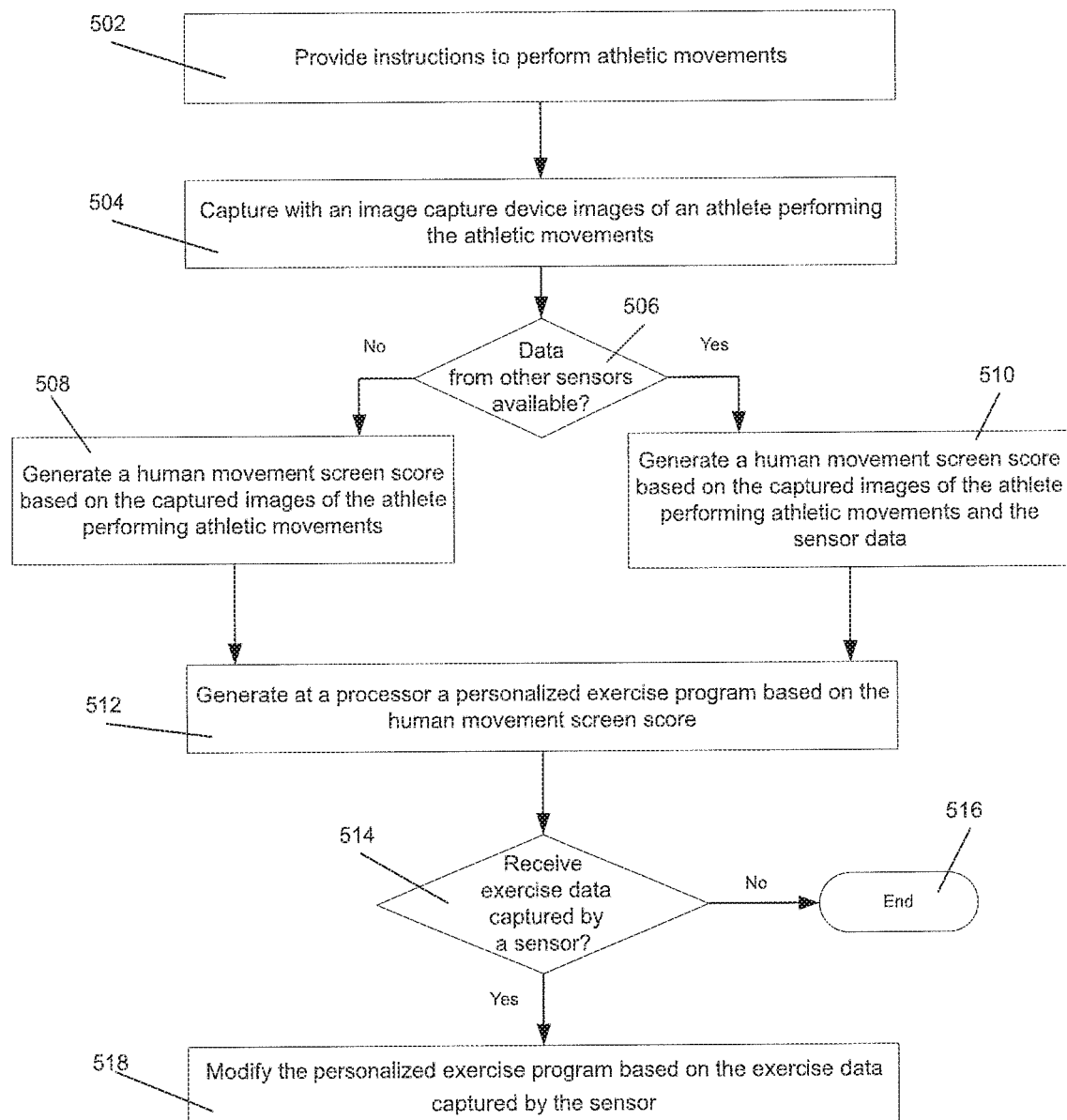
FIG. 5 illustrates an exemplary method that may be used to generate personalized training programs in accordance with an embodiment of the invention

FIG. 5 illustrates an exemplary method that may be used to generate personalized training programs in accordance with an embodiment of the invention. First, in step 502, instructions to perform athletic movements are provided. The instructions may be generated at a video game console and displayed on a display device, such as a television. Exemplary instructions to perform athletic movements are described in detail below. The athletic movements may be used to generate a human movement screen score. The movements may each map to a specific body movement. In one embodiment, the athletic movements include deep squat, hurdle step, in-line lunge, shoulder mobility, active leg raise, push up and rotary stability. FIG. 6 show exemplary instructions that may be provided to a user to perform the athletic movements.

Next, an image capture device may be used to capture images of an athlete performing the athletic movements in step 504. The image capture device may include multiple cameras. In one embodiment the image capture device includes three cameras and is used to capture movement in three dimensions. Various embodiments may include cameras that capture light in the visible and/or infrared spectrums.

It step 506 it is determined if data from one or more other sensors is available. Others sensors may include an accelerometer worn on the wrist or embedded in or attached to footwear, a gyroscope, a heart rate monitor, a compass, a location tracking device, such as a GPS device, pressure sensors inserted into footwear or any of the sensors described above that can be used to capture athletic movements and/or athletic performance. The data received from the image capture device and one or more sensors may be used to generate a human movement screen score. When only data from the image capture device is available, in step 508 a human movement screen score is generated with data from the image capture device. When additional sensor data is available, in step 510 a human movement screen score is generated with data from the image capture device and data from more or more additional sensors. In alternative embodiments a human movement screen score may be generated with only data from the image capture device even when other sensor data is available. For example, sensor data may be available but determined not to be credible or below a threshold. In some embodiments the system may also selectively use data from any of the available sensors.

After a human movement screen score is generated, in step 512 a personalized exercise program is generated based on a human movement screen score. The personalized exercise program may be generated via a device, such as a video game console, a server, or computer 102, that includes one or more processors. The human movement screen score may reveal areas that can be improved and the personalized exercise program may address those areas. FIG. 7 illustrates exemplary personalized exercise program phases in accordance with an embodiment of the invention. Column 702 lists exercises that may be used to generate human movement screen scores for various body movements. Columns 704 and 706 show exemplary criteria that may be used to score each exercise. Two levels are shown for illustration purposes only. Various embodiments may use three, four or more scoring levels. In one embodiment, four scoring levels are used and the levels include (1) experienced pain during the exercise; (2) exercise was not functionally performed; (3) exercise performed acceptably; and (4) exercise performed well. Columns 708a-708c shown exemplary exercises that may be part of a personalized training program. A personalized exercise program may include exercises that start at different phases based on the relevant human movement screen score. For example, core stability may start at phase 1 and twist may start at phase 2.

In alternative embodiments a user may also provide preference data that is used to generate the personalized exercise program. The preference data may include time commitments, numbers of exercise sessions, preferred days to exercise, preferred exercises and goals. In one embodiment a user may provide access to an electronic calendar, such as one stored on a website, that shows the user's availability to exercise and the personal training system scans the calendar to determine availability and time commitments. The personal training system may look at historical calendar data to determine probable best times and available time commitments or future calendar data to determine actual availability. The personal training system may also be configured to update the exercise program based on the user's actual availability. For example, a user may have an exercise session scheduled for Monday evening and a scan of the user's calendar reveals that the user has an appointment Monday evening that makes exercising not practical. The personal training system may modify the exercise program to reschedule the exercise to another day. Other changes to the exercise program may also be made to keep the user on track to reach goals. The personal training system may even add calendar events to the user's calendar.

Users may exercise at locations away from the personal training system. Exercise data may be captured by a variety of sensors, such as accelerometers worn on the wrist or other body parts. Accelerometers may also be embedded in or attached to footwear or articles of clothing. Other sensors that may be used to capture exercise data away from the personal training system include gyroscopes, location tracking devices, such as a GPS device, heart rate monitors, pressure sensor systems placed in footwear and any of the sensors described above. The captured exercise data may be provided to the personal training system via a network connection or hardware port, such as a USB port. Returning to FIG. 5, in step 514 it is determined whether exercise data has been captured by a sensor while the user was exercising away from the personal training system. Step 514 may include determining that GPS data that was captured with a mobile phone while a user ran is available. If no sensor data is available, the process ends in step 516. One skilled in the art will appreciate that the method shown in FIG. 5 is merely exemplary and may be modified to include other steps and various loops. For example, instead of ending in step 516, the process may wait a predetermined time and repeat step 514.

When sensor data is received, in step 518, the personal training system may modify the personalized exercise program based on the exercise data captured by the sensor. Modifications may include one or more changes to the types of exercises or durations of exercises. For example, if the sensor data indicates that the user recently ran, the next session of the personalized exercise program may be modified to not exercise the primary muscle groups involved in running. Other exemplary modifications include reducing the duration or eliminating an exercise session.

B. Illustrative Embodiments

When a user begins an exercise program, the computer 102 may prompt the user to perform a series of exercises in front of an image capturing device. The computer 102 may process the images and assign a score indicating how well the user was able to complete each of the exercises to establish a baseline physical fitness level. When performing an exercise, the computer 102 may instruct the user to position him or herself at a certain distance and orientation relative to an image capturing device. The computer 102 may process each image to identify different parts of the user's body, such as, for example, their head, shoulders, arms, elbows, hands, wrists, torso, hips, knees, ankles, feet, or other body parts. The computer 102 may generate a set of data identifying a location of various body parts within the image. The computer 102 may process the data set to determine a relationship between certain body parts. These relationships may include an angle of one body part relative to another. For example, when the user is doing a squat, the computer 102 may compare the angle of a user's torso with an angle of the user's thigh. In another example, the computer 102 may compare a location of a user's shoulder relative to their elbow and hand during a push up.

The computer 102 may compare the data set to a desired data set for each exercise to monitor the user's form while performing an exercise. The desired data set may include multiple comparison points throughout an exercise. For example, a push up may be divided into four events: (1) the lowest point where the user's chest is nearest to the ground and their arms are bent; (2) a highest point where the user's chest is farthest from the ground and their arms are straightened; (3) an upward event where the user transitions form the lowest point to the highest point; and (4) a downward event where the user transitions form the highest point to the lowest point. The desired data set may specify comparison points for each of these events focusing on certain body parts. For example, at each comparison point during a pushup, the computer 102 may monitor the spacing of the user's hands, the straightness of the user's back, a location of the user's head relative to their torso, the spacing of the user's feet relative to one another, or other aspects. The desired data set may specify desired locations for each body part being monitored during comparison points within an exercise, as well as permitted variations from the desired locations. If the user's body part varies beyond what is permitted, the computer 102 may provide the user with feedback identifying the body part and a correction to the user's form (e.g., back is arched, and not straight, during a pushup).

The computer 102 may also score the user's performance of an exercise. Scoring may be based on the user's form, how quickly the user was able to complete the exercise (e.g., 20 pushups in 60 seconds), a number of repetitions the user completed, the amount of weight the user used during an exercise, or other exercise metrics. In additional to processing the images, the computer 102 may receive data from other sources. For example, the user may run a predetermined distance as measured by a sensor attached to the user (e.g., sensor in a shoe) or global positioning system (GPS) device and may upload the data to the computer 102. Based on the images and/or data acquired by other sensors, the computer 102 may determine areas of weakness for the user (e.g., inability to do a pull up) and design a workout to help the user improve their overall fitness level. Score may be a function of a particular drill and may be focused on position, accuracy and correct execution. Scoring may also be based on time and/or a number sets or repetitions within a set time period.

Figure 8:
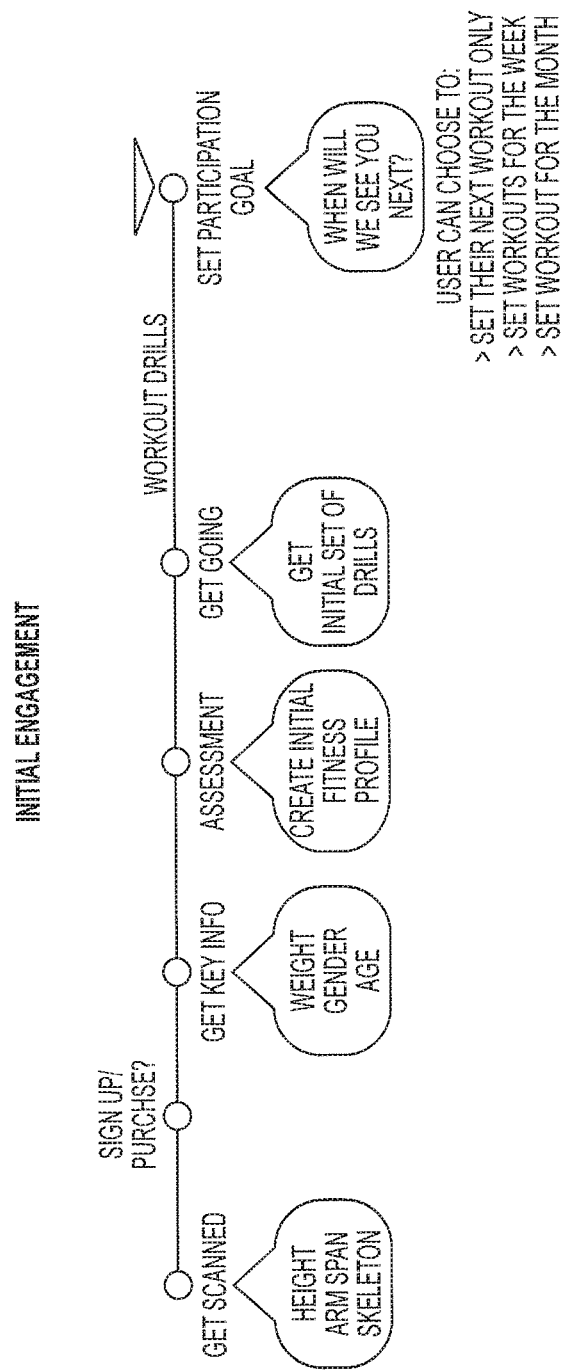
FIG. 8 illustrates another example flow diagram for a user's initial interaction to determine a user's baseline physical fitness level.

FIG. 8 illustrates an example flow diagram for a user's initial interaction to determine a user's baseline physical fitness level. In this example, the system may scan the user and prompt the user to sign up and purchase automated training. The system 300 may obtain information from the user about weight, gender, and age, and create an initial baseline physical fitness level. The system may lead the user through an initial set of drills, and set a participation goal.

After completing the baseline physical fitness level for the user, the computer 102 may then create an initial personalized program. The initial personalized program may be a function of user input, static assessment of the user, and a human movement screen. User input may include a user's time commitment, as well as number of exercise sessions per week and one or more goals. The status assessment may provide the user with information and coaching on exercises. The human movement screen score may be assessments of the user's performance of the exercise drills.

Figure 9:
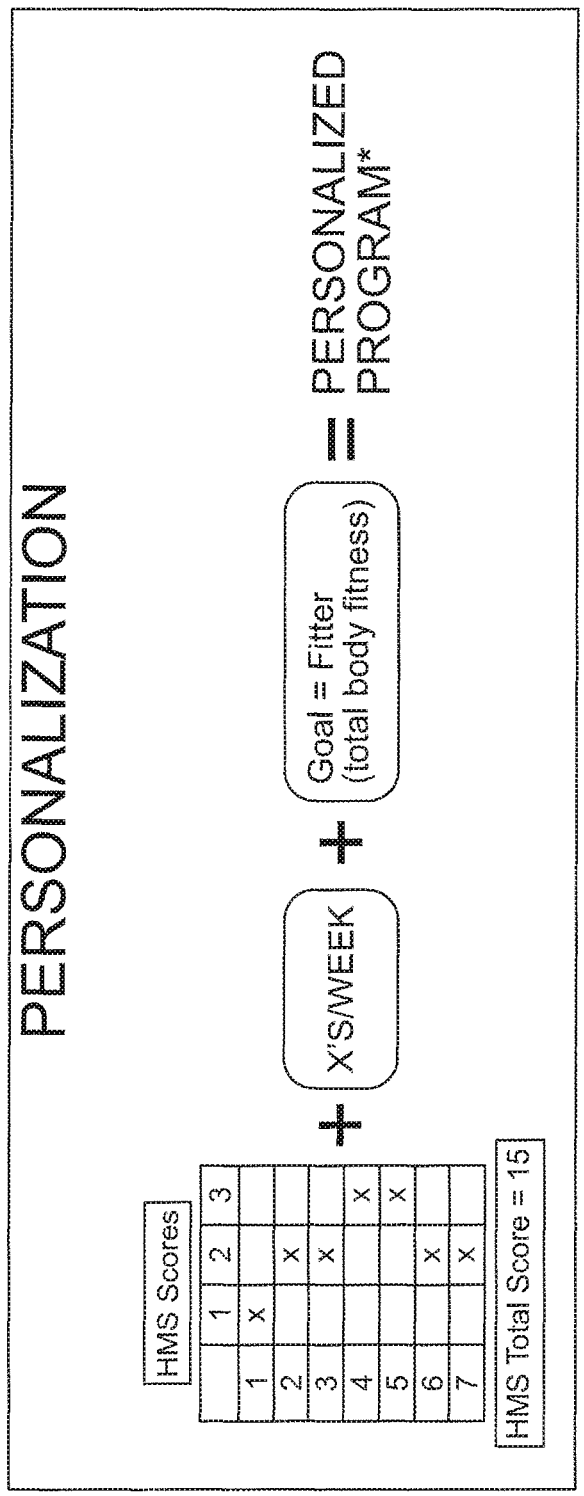
FIG. 9 illustrates an example flow diagram creating a personalized exercise program

FIG. 9 illustrates an example of creating a personalized exercise program. The personalized program may be a function of human movement screen scores, the number of exercise sessions per week the user desires, and the goal of the user (e.g., total body fitness, run a marathon, lose weight, etc.). Goals may also include "get strong", "get lean" and/or "get toned." Other factors that may be considered include a user's fitness profile that may consider a current assessment of a user's fitness level as well as user preferences. The user may also specify multiple goals, including to be fitter, stronger, faster, centered, etc. The user may specify a fitness level, such as, for example, beginner, intermediate, advanced. The computer 102 may evaluate the user's fitness level over time to confirm the user input fitness level or to adjust exercises based on measured performance rather than the user specified fitness level. The user may also specify a desired length of their program, such as 1 week, 2 weeks, 4 weeks or a custom length.

Figure 10:
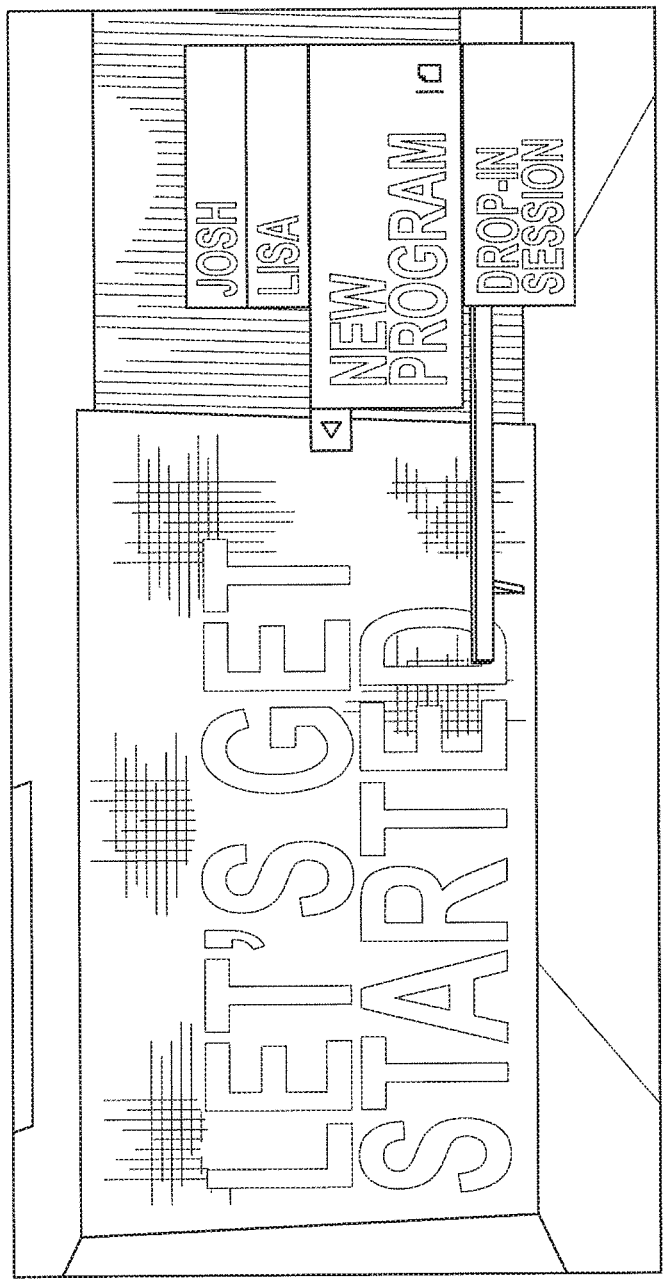
FIG. 10 illustrates an example graphical user interface with options to select a trainer, to start a new program, or to do a drop-in workout session.
Figure 11:
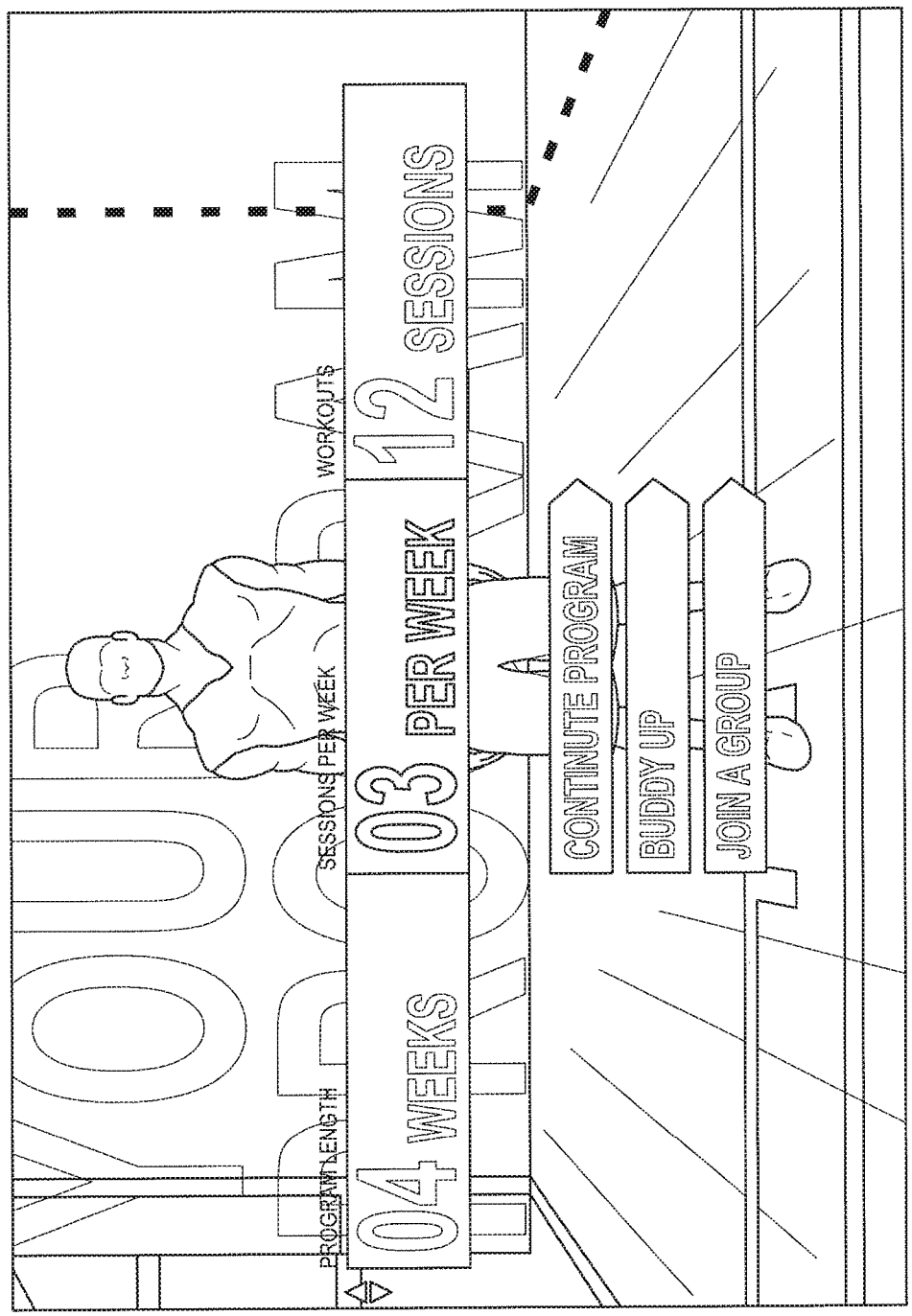
FIG. 11 illustrates an example graphical user interface prompting a user to input user desired workout selections.

To obtain these inputs, the computer 102 may present a graphical user interface (GUI) on the display 302 prompting the user to start a new program and to provide input for the initial personalized program, as shown in FIGS. 10-13. In FIG. 10, the graphical user interface may present the user with options to select a trainer (e.g., tabs for Josh or Lisa), to start a new program, or to do a drop-in session. In response to selecting to start a new program, the graphical user interface may prompt the user to input user desired workout selections, as depicted in FIG. 11. The user may, for example, select a program length and a number of sessions per week. The GUI may then present the user with a total number of workout sessions. The GUI may also present the user with options to buddy up or to join a group where a user may be networked (e.g., via the Internet) with at least one other user to exercise at the same time. When a drop in session is selected, drills for a single session may be selected in a manner that appears random to users, i.e. pseudo random. The selection may be based on one or more goals of the user, such as strength and cardio goals. The selection may also be based on time or performance of the user. The system may select drills for as long as the user wishes to exercise.

Figure 12:
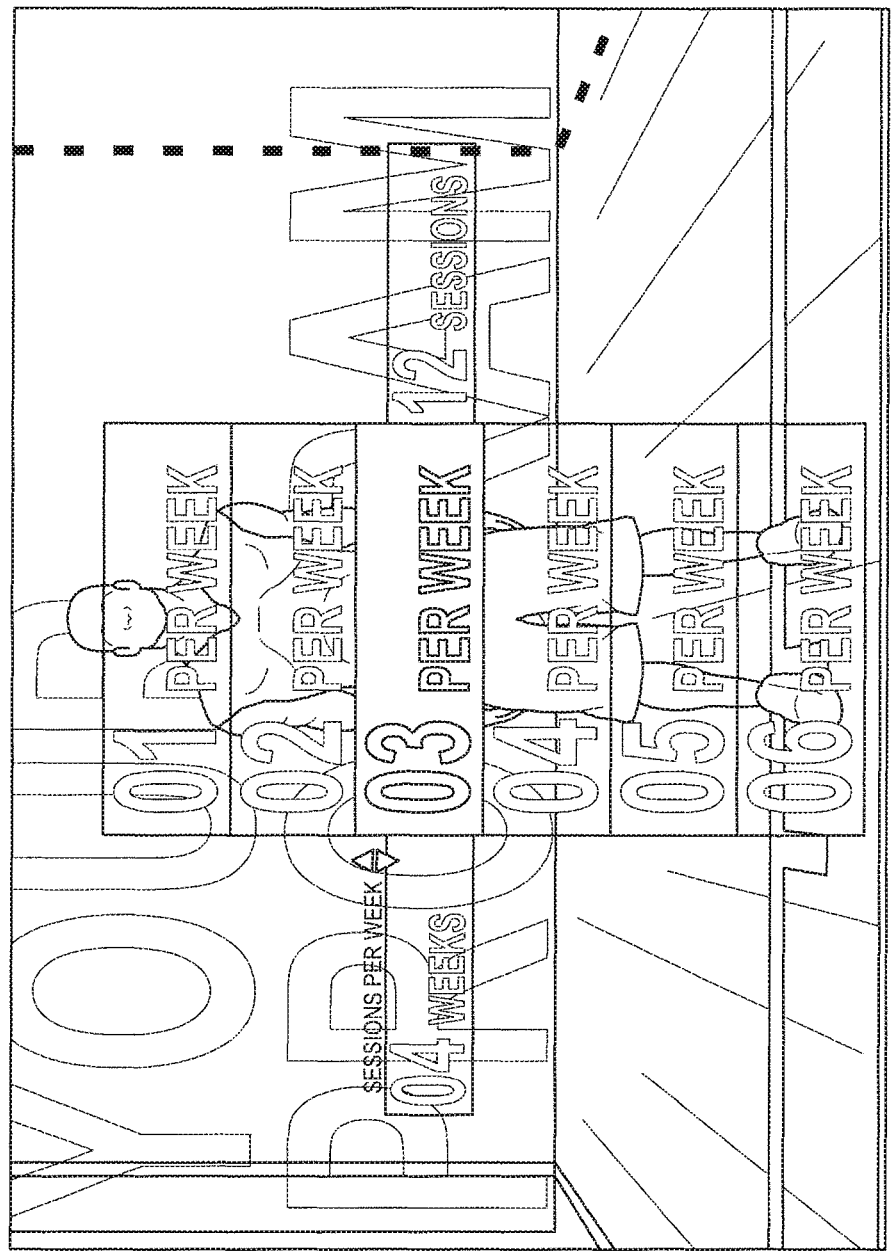
FIG. 12 illustrates an example graphical user interface that includes a scroll bar permitting a user to select a desired number of times to exercise per week.
Figure 13:
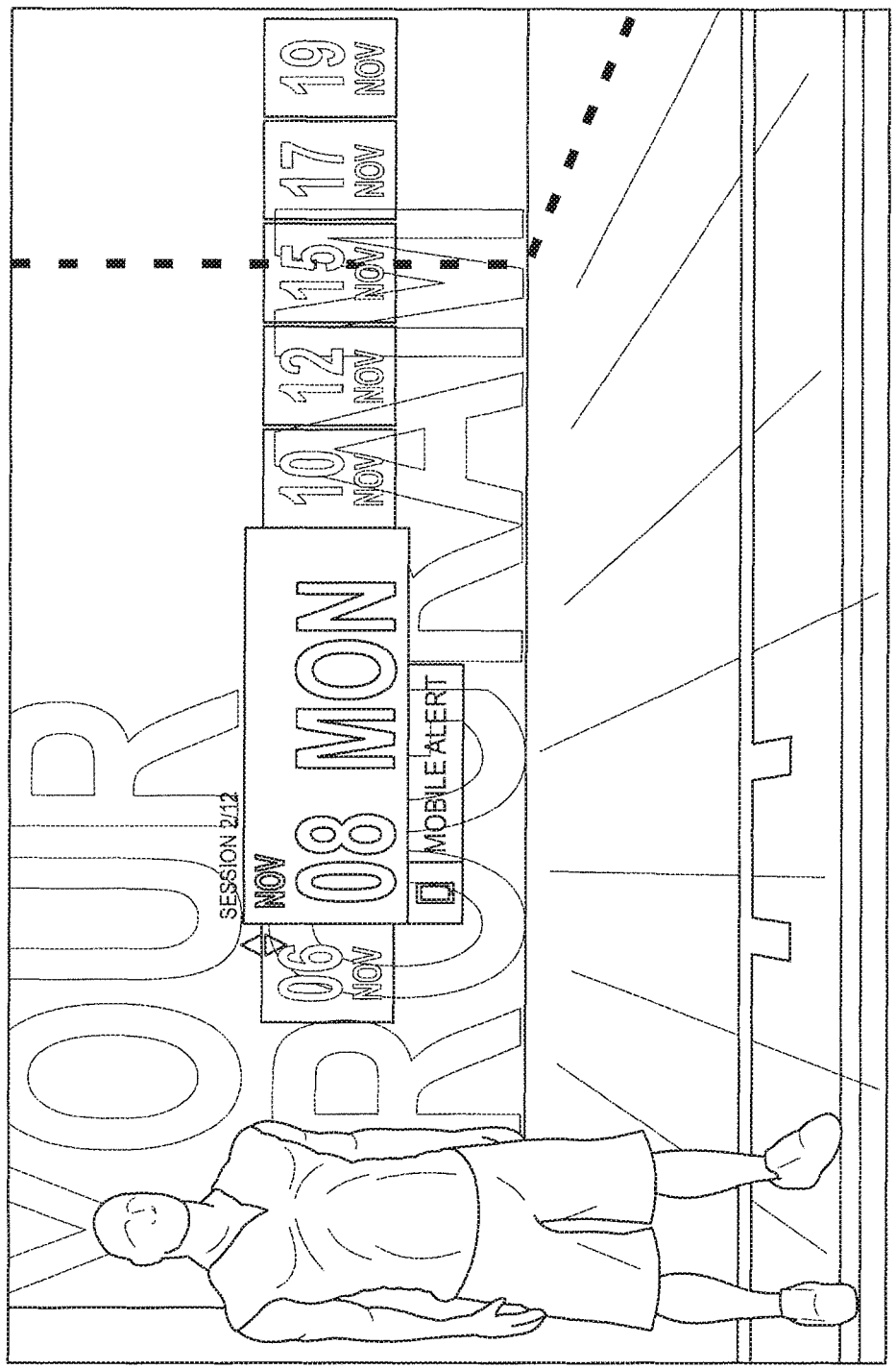
FIG. 13 illustrates an example graphical user interface permitting a user to input reminders so that an email or text message may be sent to a device (e.g., mobile phone) to remind the user about an upcoming workout session.

FIG. 12 shows a scroll bar in the GUI where a user may select a desired number of times to exercise per week. In FIG. 13, the GUI permits the user to input reminders so that an email or text message may be sent to a device (e.g., mobile phone) to remind the user about an upcoming workout session. The reminder may include a time and date of one or more upcoming workout sessions.

Figure 14:
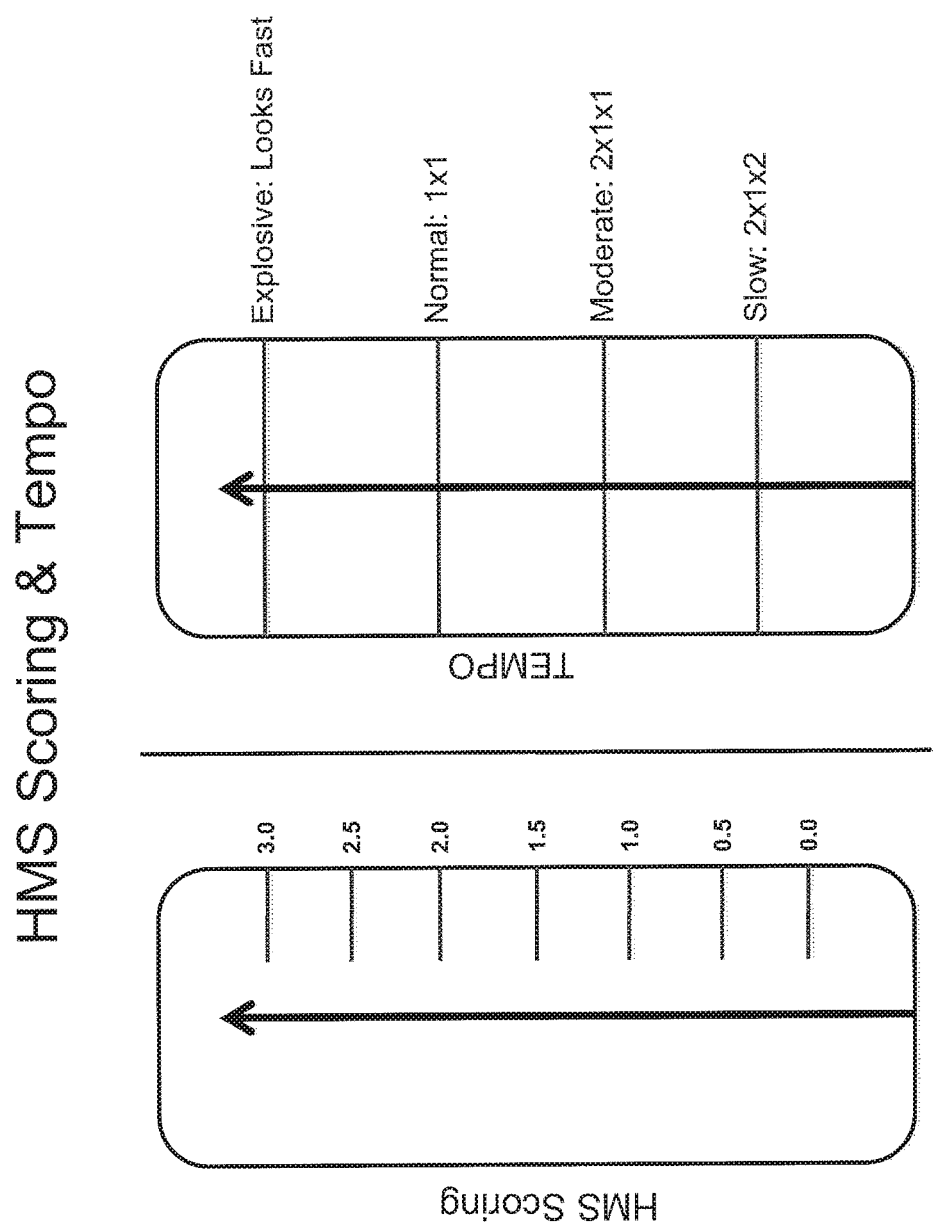
FIG. 14 illustrates an example initial baseline physical fitness level based on human movement screen scoring and tempo.

FIG. 14 illustrates an example baseline physical fitness level assessment determined using human movement screen scoring and tempo. The computer 102 may prompt the user to perform one or more exercise drills, and determine a score each of the assessment exercises using human movement screen scoring as well as the tempo of the user completing the exercise drills. The human movement screen scoring may range from 0 to 3, and the tempo may have categories of slow, moderate, normal, and explosive.

Figure 15:
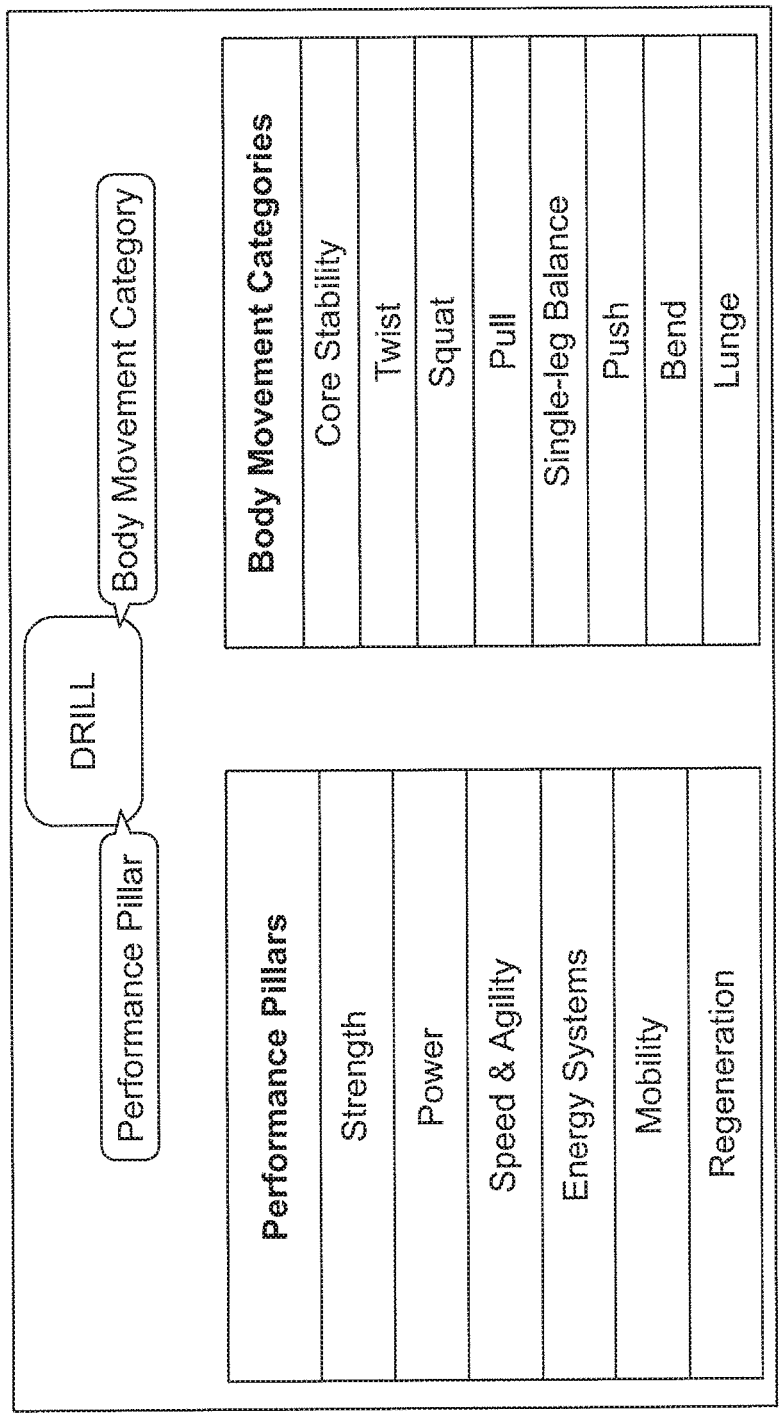
FIG. 15 illustrates example drills for assessing user performance relative to performance pillars and body movement categories.

The drills may be used for assessing user performance relative to performance pillars and body movement categories, as depicted in FIG. 15. The performance pillars may be assessments designed to analyze a user's strength, power, speed & agility, energy systems, mobility, and regeneration. Body movement drill categories may include assessments of core stability, twist, squat, pull, single-leg balance, push, bend, and lunge.

Figure 16:
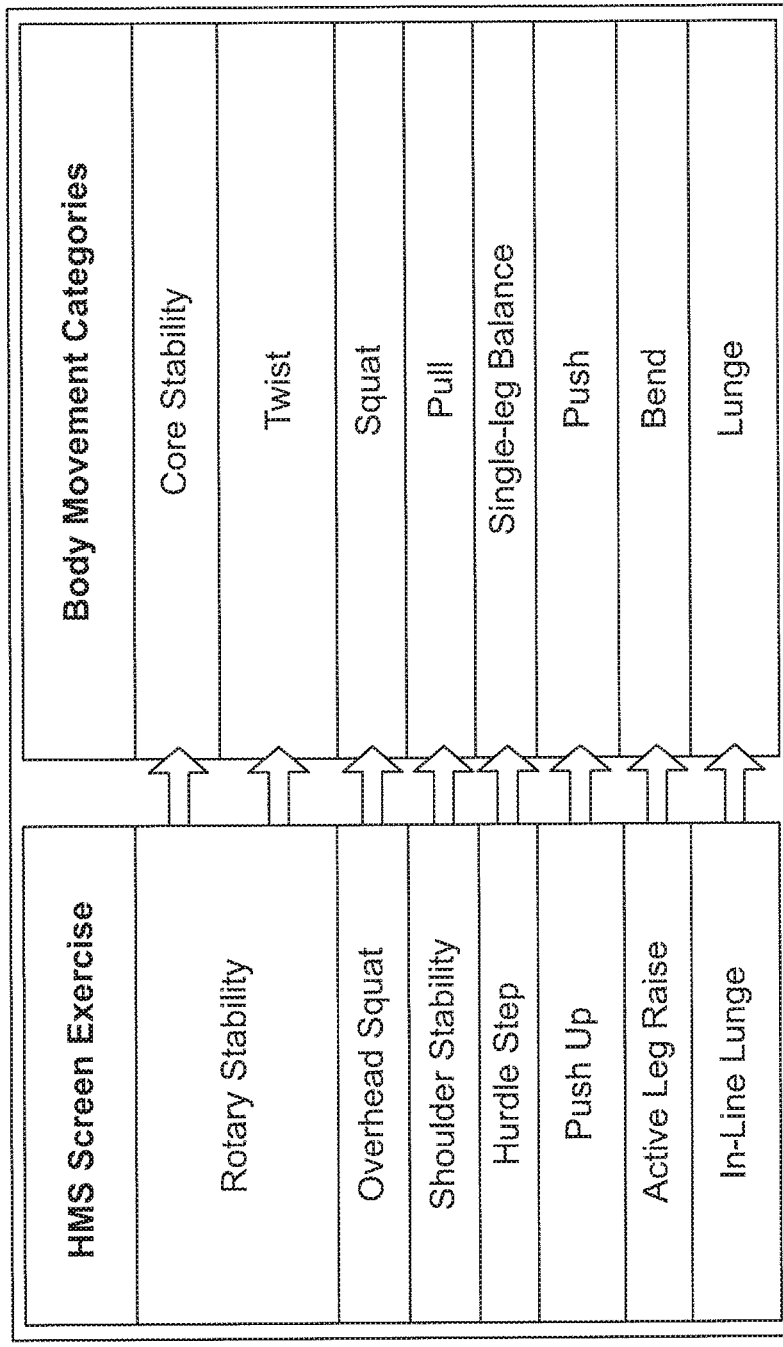
FIG. 16 illustrates an example relationship between body movement categories and human movement screen exercises.

FIG. 16 illustrates an example relationship between body movement categories and human movement screen exercises. Human movement screen exercises may include rotary stability, overhead squat, shoulder stability, hurdle step, push up, active leg raise, and in-line lunge. Rotary stability may correspond to the core stability and twist body movement categories, overhead squat may correspond to the squat body movement category, shoulder stability may correspond to the pull body movement category, hurdle step may correspond to the single-leg balance body movement category, push up may correspond to the push body movement category, active leg raise may correspond to the bend body movement category, and in-line lunge may correspond to the lunge body movement category.

Figure 18:
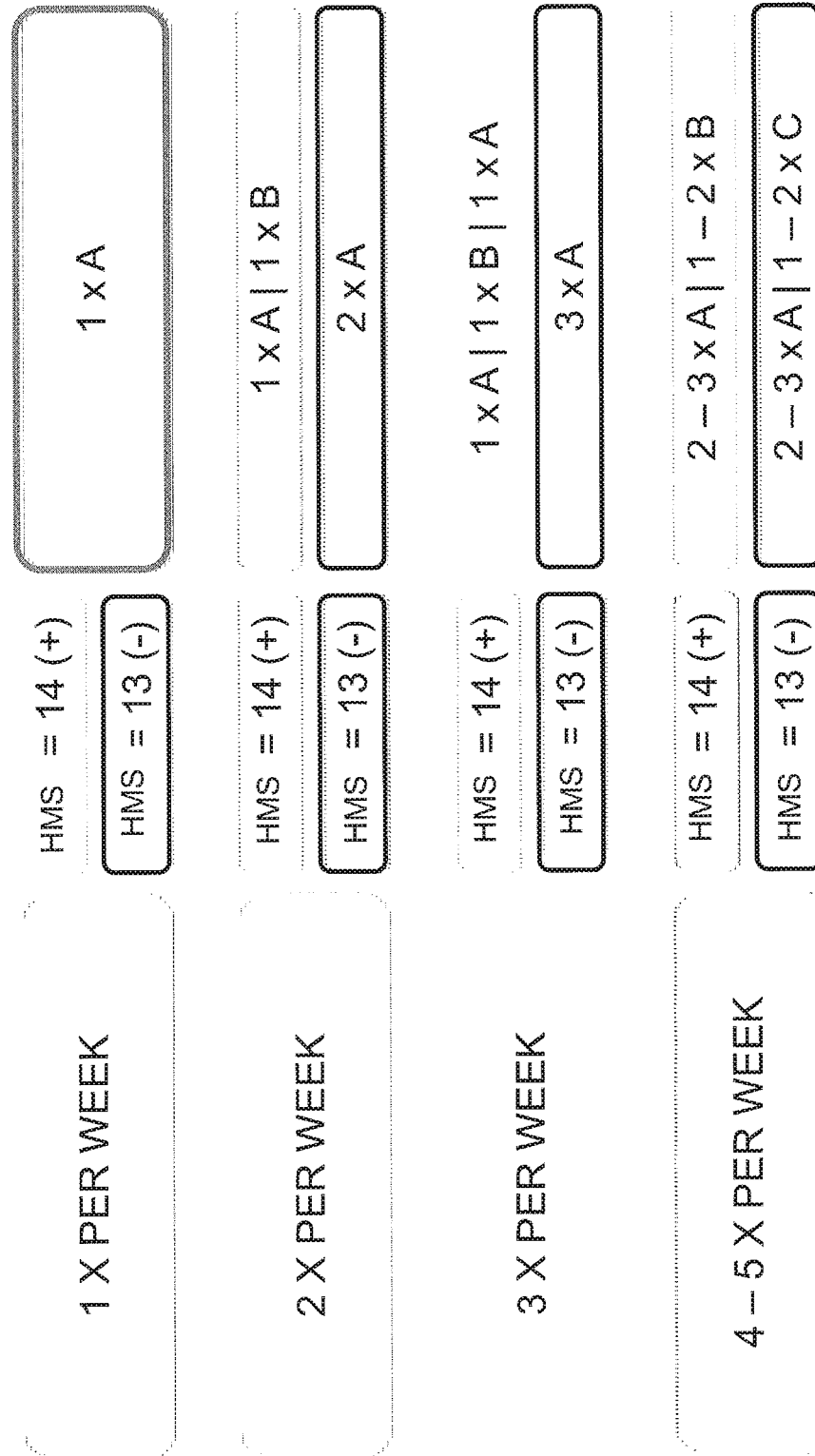
FIG. 18 illustrates an example workout structure.

The computer 102 may instruct the user to perform the same drill at various tempos, as described in FIG. 17. The tempo of the drill can affect which performance pillar is being assessed. In a squat, for example, the computer 102 may assess a user's strength in a slow tempo and a user's power in an explosive tempo. FIG. 18 illustrates four different tempo categories including slow, moderate, normal, and explosive. Slow may involve the user moving down in an exercise over two seconds, holding for one second, and moving up in the next two seconds.

Figure 19:
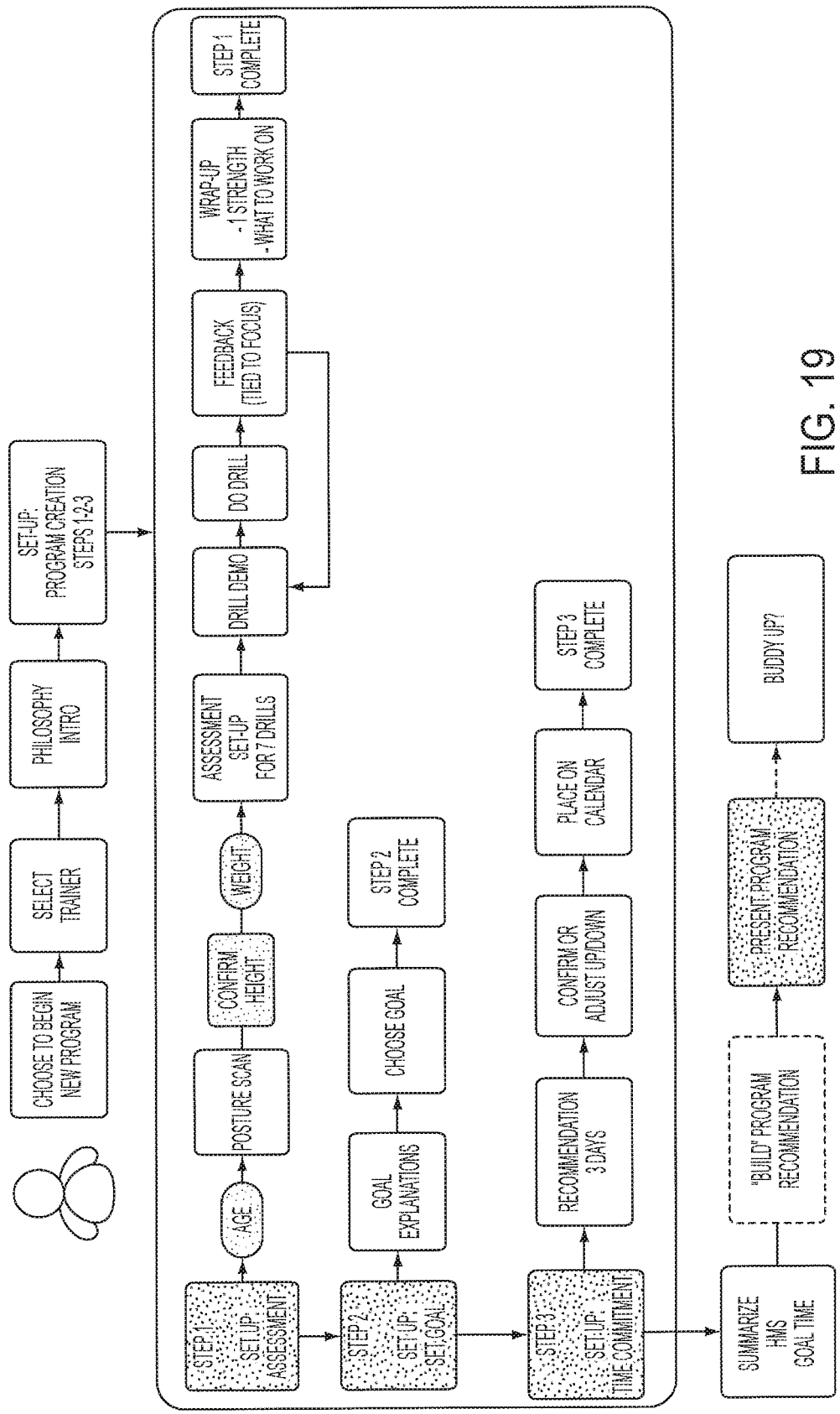
FIG. 19 illustrates an example flow diagram for setting goals and encouraging commitment from a user.

Based on the human movement screen scoring, the computer 102 may generate a workout structure for the user, an example of which is depicted in FIG. 18. The computer 102 may consider the number of exercise sessions the user is willing to do per week in combination with the human movement screen score to generate a workout program. The workouts may focus on one of three activities: an A strength workout, a B cardio and metabolic workout, and a C regeneration workout. If a user is only willing to workout once per week, the computer 102 may assign a strength workout (i.e., 1×A). If the user is willing to workout more than once per week, the computer 102 may consider the human movement screen score for the user. Generally, the computer 102 may differentiate between scores 14 and above and scores 13 and below. For human movement screen scores 14 and above, the computer 102 may assign one strength workout, one cardio and metabolic workout per week, and no regeneration workouts. For human movement screen scores 13 and below, the computer 102 may assign two strength workouts, no cardio and metabolic workout per week, and no regeneration workouts. The computer 102 may also structure workouts for users desiring to workout 3 or more times per week, as shown in FIG. 19. Alternative embodiments of the invention many include other workout structures that include different types of workouts and numbers of sessions.

FIG. 19 illustrates an example flow diagram for setting goals and encouraging commitment from the user. The computer 102 may present the user with a result of the assessment and comments, and prompt the user to select 1 or more goals (e.g., lose weight, gain strength, etc.). Based on the user's selection and the baseline physical fitness level, the computer 102 may recommend a workout plan. The computer 102 may also permit the user to record a statement of their goal. Goals may be tailored to performing certain events and may include training sessions developed for or by professional athletes. For example, the computer 102 may load a training session pack developed for or by a pro athlete (e.g., 'Paula Radcliffe's marathon training') for real life events.

FIG. 20 illustrates an example workout plan. In this example, the workout plan is for a six month exercise program designed to improve the user's human movement screen score over time. Other workout plans could have different durations, such as one month. In some embodiments users are not presented with an entire workout plan when it is created. The leftmost column may indicate the body movements that correspond to the human movement screen scoring areas, and the remaining columns may correspond to month long programs specifying a drill in each of the body movement categories. Each of phases 1-6 may be a month long program, and the score 1 and 2 columns may correspond to month long programs of remedial exercises for users having human movement screen scores less then 3 in a particular body movement category. In phase 6, for example, the program includes a renegade row exercise in the core stability movement category, a seated Russian twist exercise in the twist movement category, and so forth. The user may perform the same exercise drills during each exercise session over the month, but the intensity and duration of each exercise drill may change over the month according to a 4 week routine. The computer 102 may also permit the user to swap one drill for an equivalent drill.

If a user receives a human movement screen score of 3 in all categories, the computer 102 may prompt the user to performance exercises shown in the month 1 column. If the user receives a human movement screen score of 1 or 2 in any body movement category, the computer 102 may prompt the user to perform the body movement in the score 1 or score 2 columns for that category. For example, if the user receives a score of 1 in the pull category, the computer 102 may prompt the user to perform the reach roll'n lift exercise in month 1, the Lying T's in month 2, and so forth along that row and the six month program would end at the bent over row exercise from the month 4 column.

In another example, the workout plan may include a baseline workout and six month long programs, examples of which are depicted in FIGS. 21-34. FIGS. 21-24 describe Workout A, which includes exercises focusing on developing a user's strength and power. FIGS. 25-32 describe Workout B, which includes metabolic focus with exercises to develop a user's speed, agility, and power. FIGS. 33-34 describe Workout C, which includes regeneration exercises such as stretching exercises. Workout A, for example, may be the priority workout if a user only works out once per week, but other workouts may be prioritized as well.

With reference to FIG. 22, the Workout A program for months 1-2 may include an exercise list, a relationship between workout phases and human movement screen, and phase details. The program may include a dynamic warm-up, followed by exercises in each of the body movement categories. After completed the listed exercises, if the user has a human movement screen score of 14 or more, the program may include a metabolic challenge where the user is prompted to perform an exercise attempting to physically challenge the user (e.g., run as fast as you can, do repetitions until muscle failure, etc.). Thereafter, the program may include regeneration exercises (e.g., stretching).

With reference to FIG. 26, the workout plan may specify a number of sets, an amount of time of exercise, and an amount of time of rest. For example, in month 1, Workout B specifies 2-3 sets per exercise, where the user works for 20 seconds followed by 20 seconds of rest.

Figure 35:
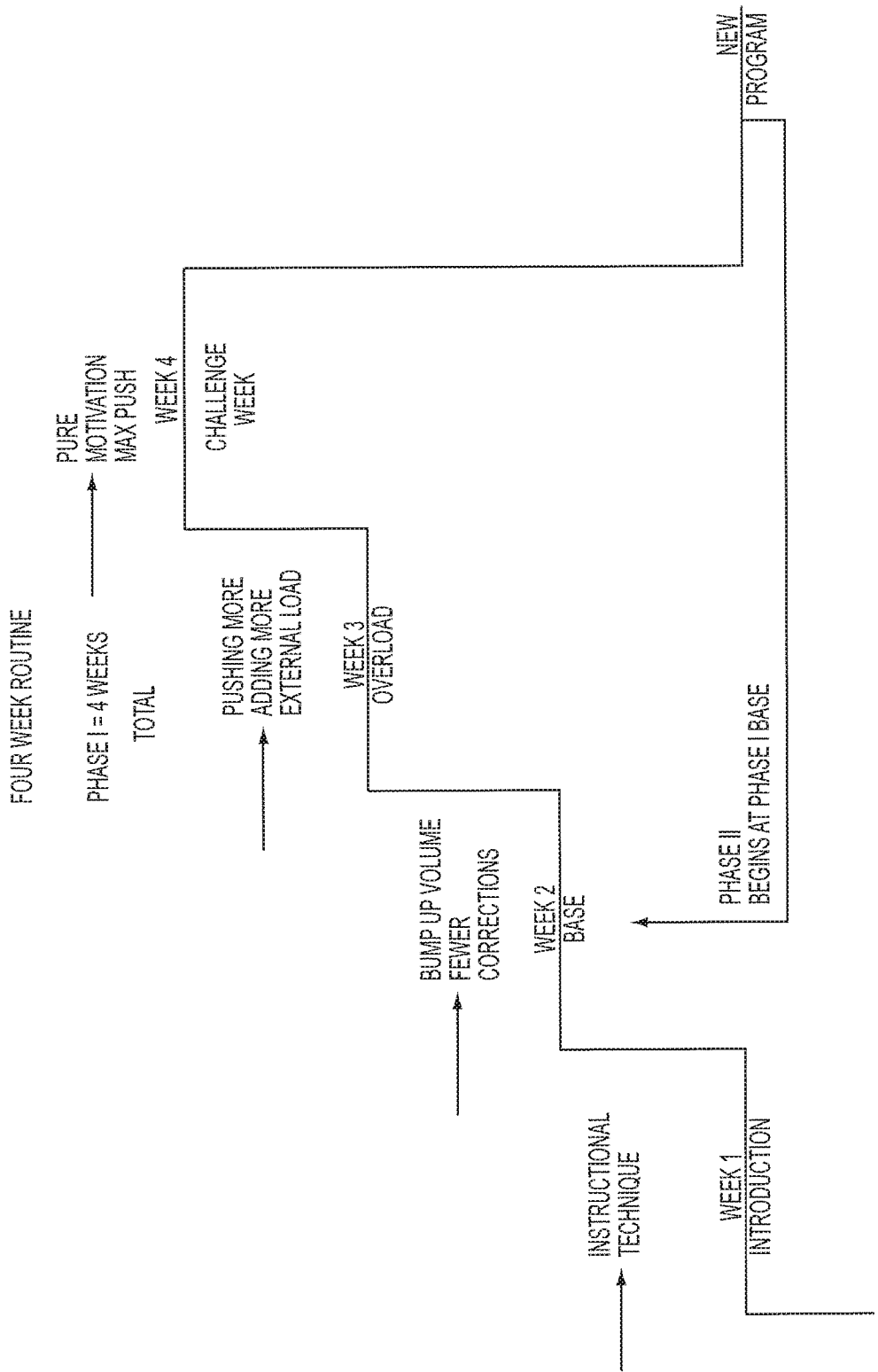
FIG. 35 illustrates an example 4 week routine to aid a user in achieving a goal.

Each month long program over the six month program may be divided into 4 phases each lasting a week, an example of which is depicted in FIG. 35. Week 1 may be the "introduction week" to introduce the user to an instructional technique and to obtain a baseline physical fitness level. Week 2 may be the "base week" and may involve the user improving their technique as well as increasing workout intensity. Week 3 may be the "overload week" and may involve adding more load (e.g., weight) to a working program and increasing intensity. Week 4 may be the "challenge week" and may involve pushing a user to their maximum. Other 4 week progressions may also be used. Generally, the human body adapts every 4-6 weeks. Some users may adapt at different intervals and the program may be structure to account for these differences. Some programs may also include shorter or longer progressions and the progressions may be determined by analyzing the performance of a user. The computer 102 prompts the user to learn proper technique which leads to progression. Challenges are increased over time by adding repetitions and equipment. As the user conquers a workout, they are given a new routine to learn, providing an intrinsic reward. The computer 102 attempts to learn a user's most effective workout, and reassess a user's performance every 4 weeks.

Figure 36:
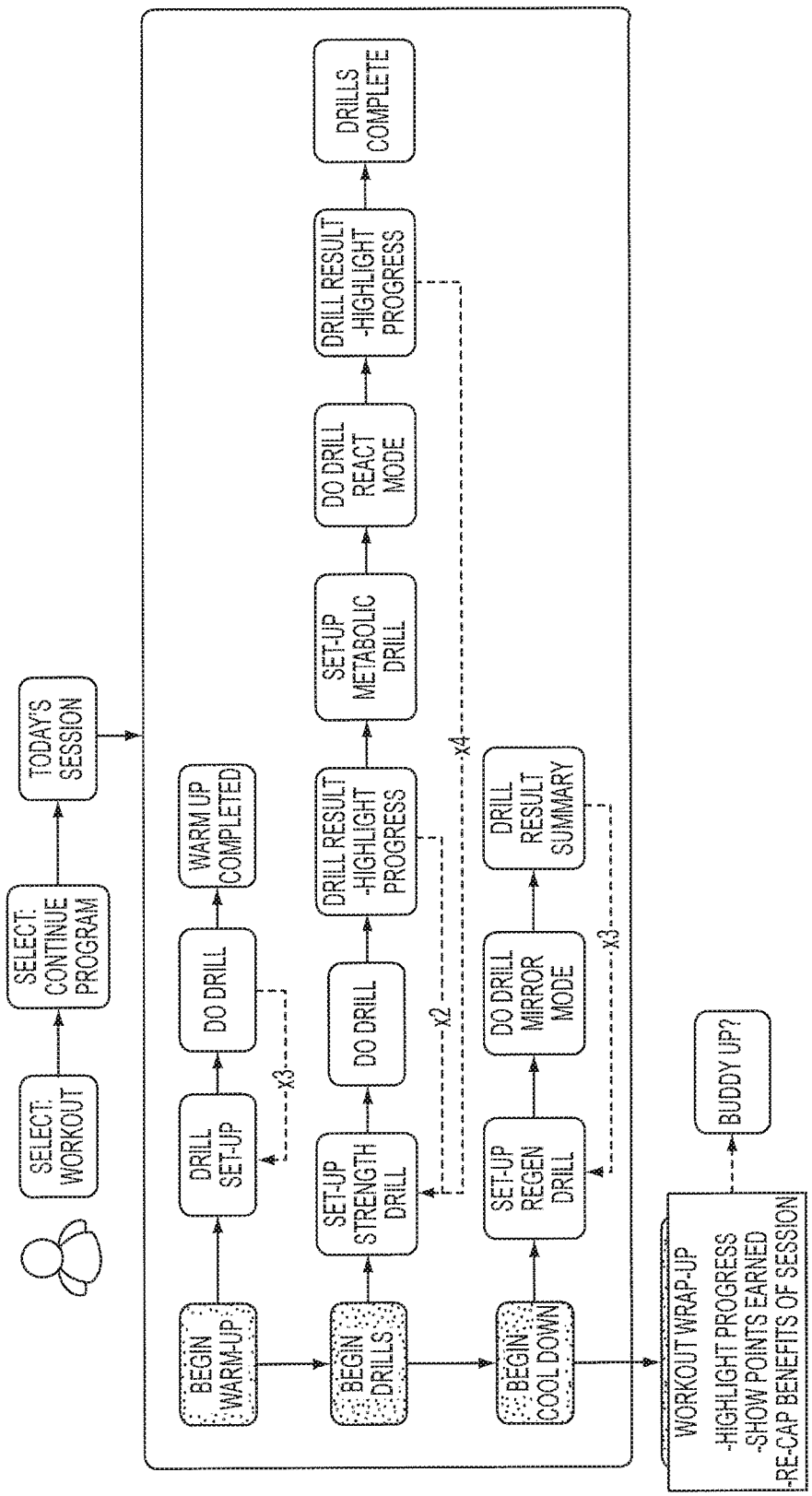
FIG. 36 illustrates an example leading a user through a workout session.
Figure 37:
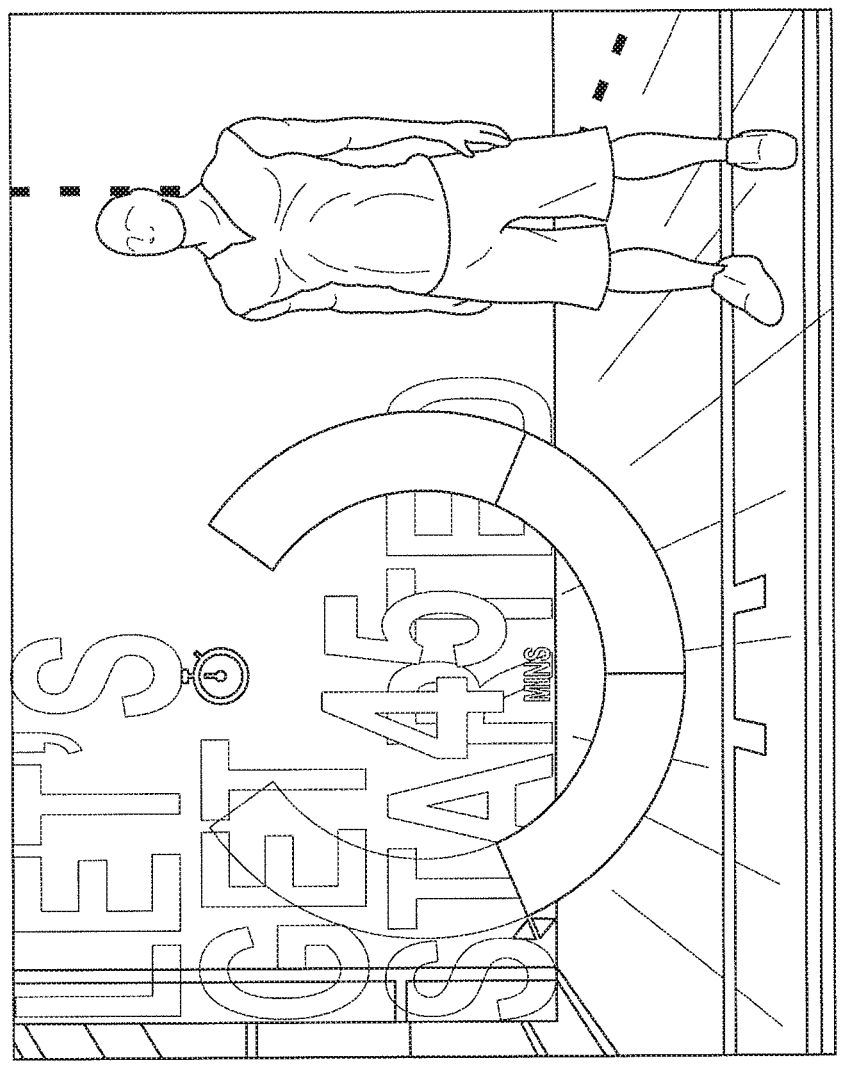
FIG. 37 illustrates an example graphical user interface prompting a user to begin a workout session, and asking how long the user has to work out.
Figure 38:
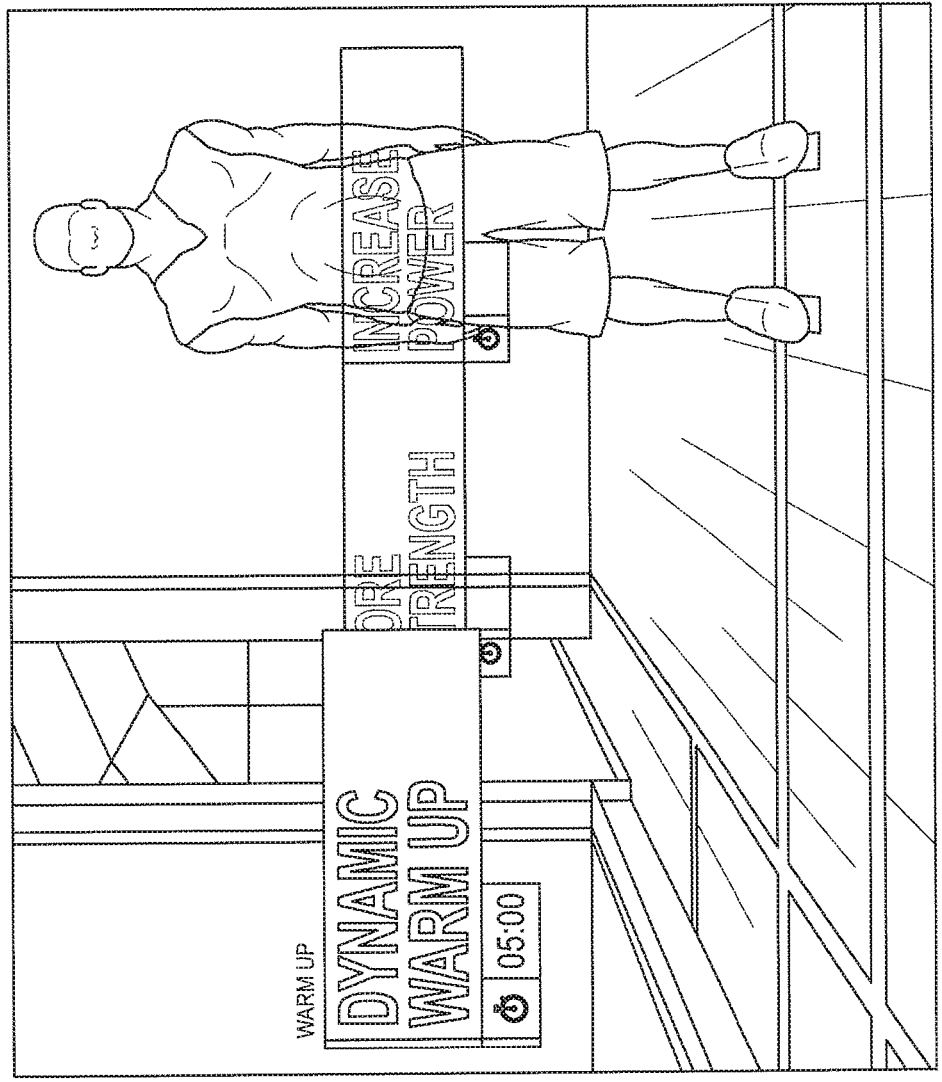
FIG. 38 illustrates an example graphical user interface leading a user through a warm up session.
Figure 39:
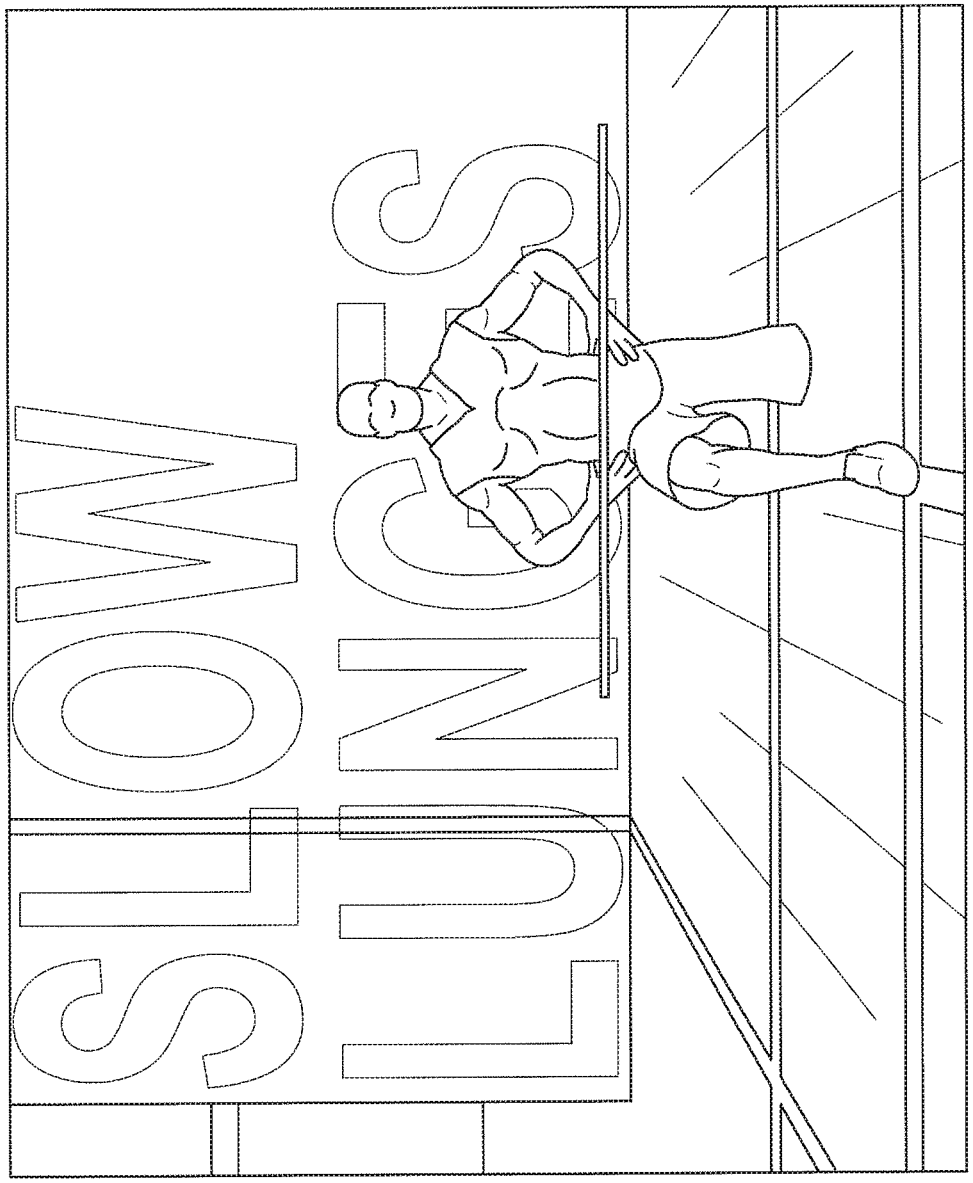
FIG. 39 illustrates an example graphical user interface providing a demonstration of a first exercise drill.
Figure 40:
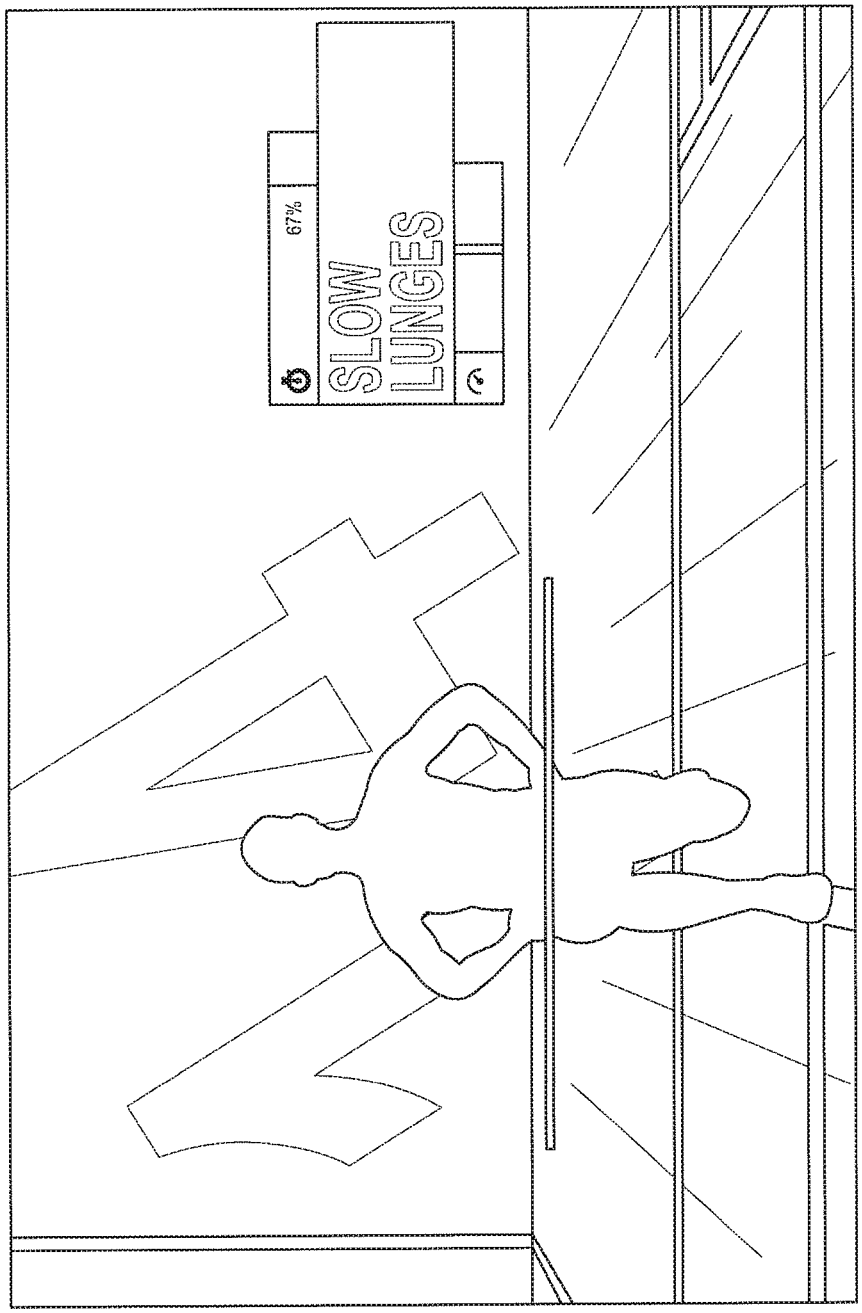
FIG. 40 illustrates an example graphical user interface displaying an image of the user performing a drill.

FIG. 36 illustrates a flow diagram for leading a user through a workout session. The computer 102 may prompt the user to begin a workout session, and ask how long the user has to work out, as seen in FIG. 37. The computer 102 may then provide a summary of the exercise drills the user is going to perform. The computer 102 may provide the how and the why of workouts to help the user get into the mindset of a competitive athlete. Competitive athletes may include professional athletes, college athletes, personal trainers, community leaderboard participants and others. For example, the drills may relate to corrective/core exercises, strength/power exercises, energize/metabolic exercises, regenerate/stretch exercises. The computer 102 may lead the user through a warm up session (as seen in FIG. 38). The warm up session may be a dynamic warm-up designed to warm up the user's muscles in each of the body movement categories. The computer 102 may then provide a demonstration of a first drill (as seen in FIG. 39). The user may then perform the drill in front of the image capturing device 304 as the computer 102 process images of the user. The computer 102 may cause a display to display an image of the user performing the drill (see FIG. 40). The computer 102 may also provide encouragement to the user to keep going (e.g., just 5 more repetitions) as well as feedback. Encouragement may be given after detecting a predetermined number of repetitions (e.g., every 3-5 repetitions), in response to detecting a repetition rate decreases below a level, or other metric.

Figure 41:
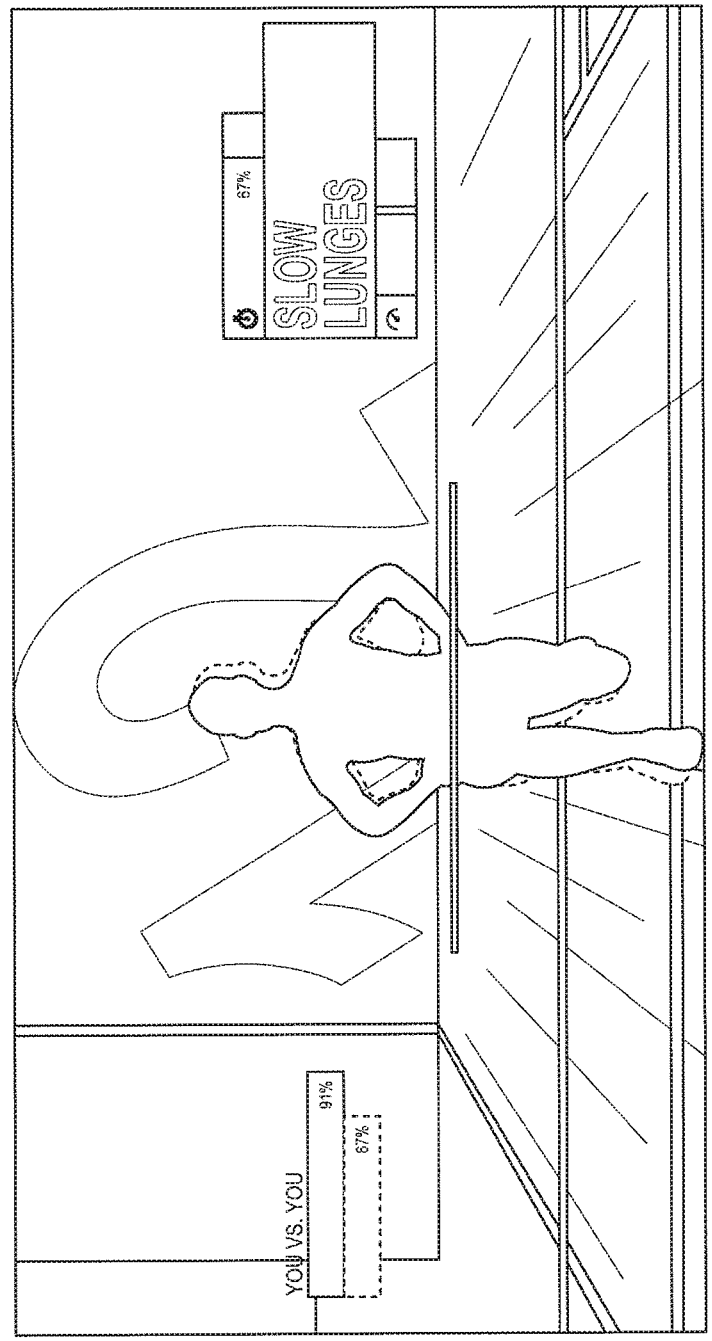
FIG. 41 illustrates an example graphical user interface comparing a user's form versus desired form.
Figure 42:
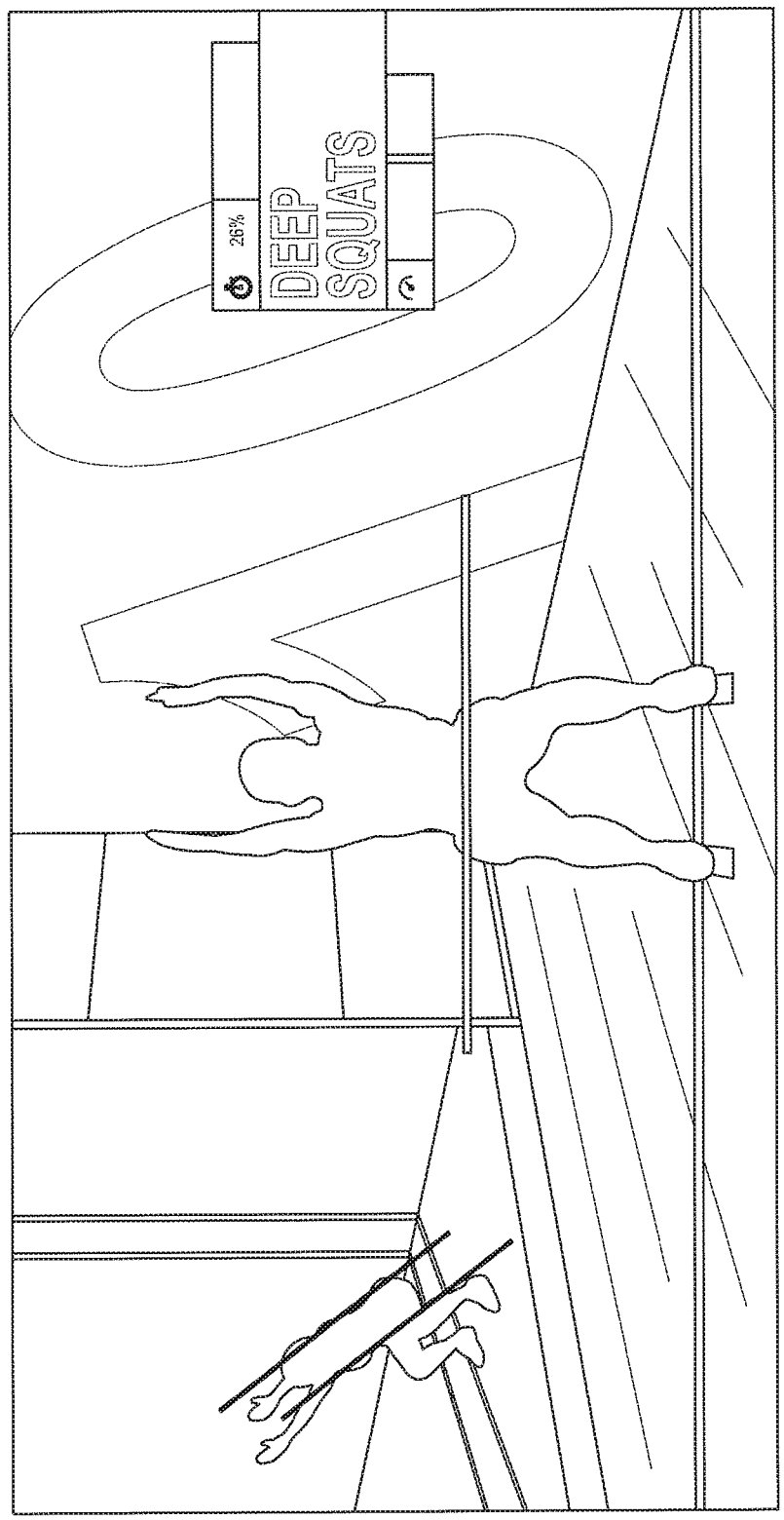
FIG. 42 illustrates an example graphical user interface including an image of a user exercising with added straight lines to show proper back and hip posture during a deep squat.
Figure 44:
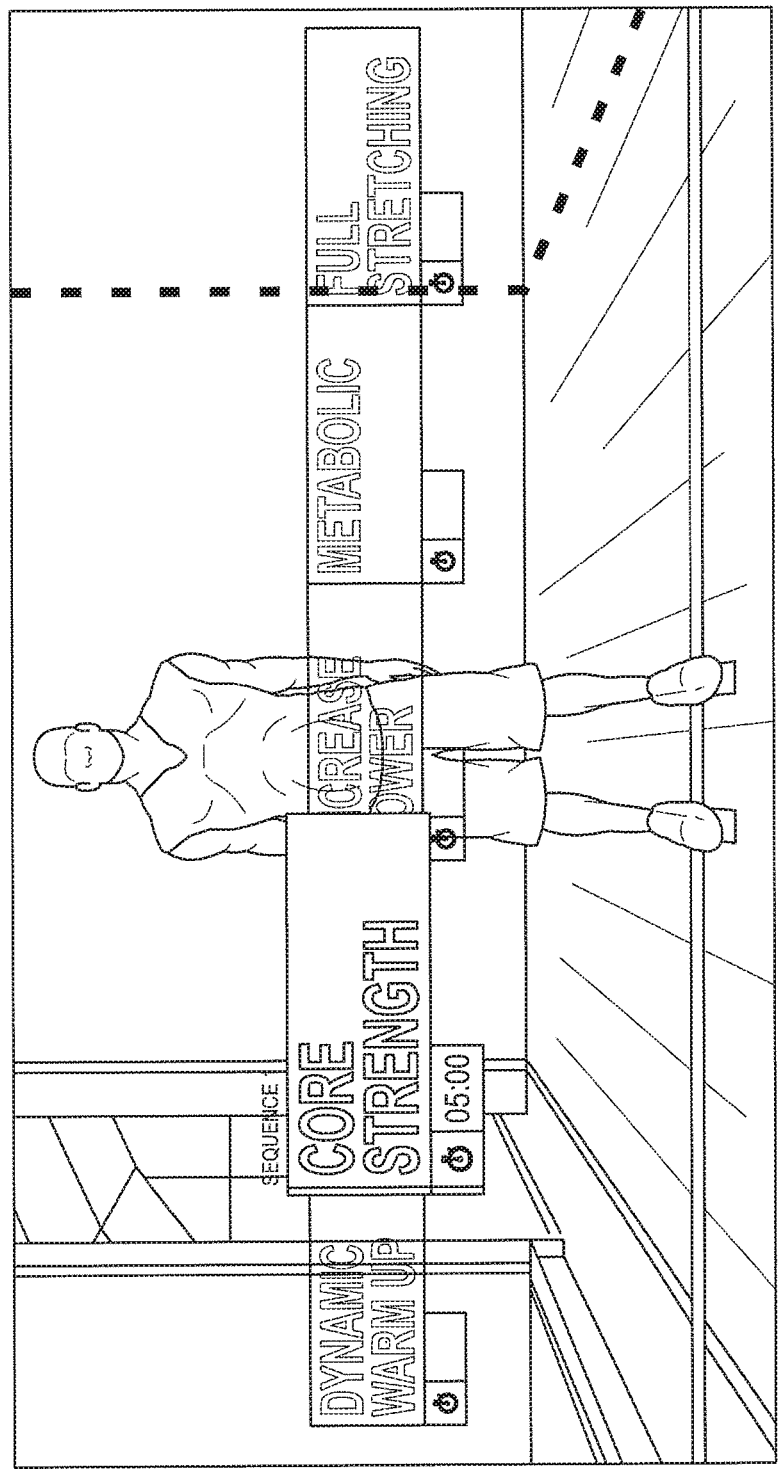
FIG. 44 illustrates an example graphical user interface informing a user of a next training category during the workout session.

The feedback may allow the user to compete against their own benchmarks to see improvement in real-time and over time. FIG. 41, for example, illustrates a comparison of a user's form versus desired form. In another example, FIG. 42 illustrates an image of the user exercising with added straight lines to show proper back and hip posture during a deep squat. In a further example, FIGS. 43A-B illustrates graphical user interfaces providing the user with feedback on their form (i.e., Correction needed: straighten knees), and removes the corrective feedback when the user's form improves. Once one drill is completed, the computer 102 may prompt the user to move onto the next drill. FIG. 44, for instance, illustrates a graphical user interface informing the user of the next training category during the workout session.

Figure 45:
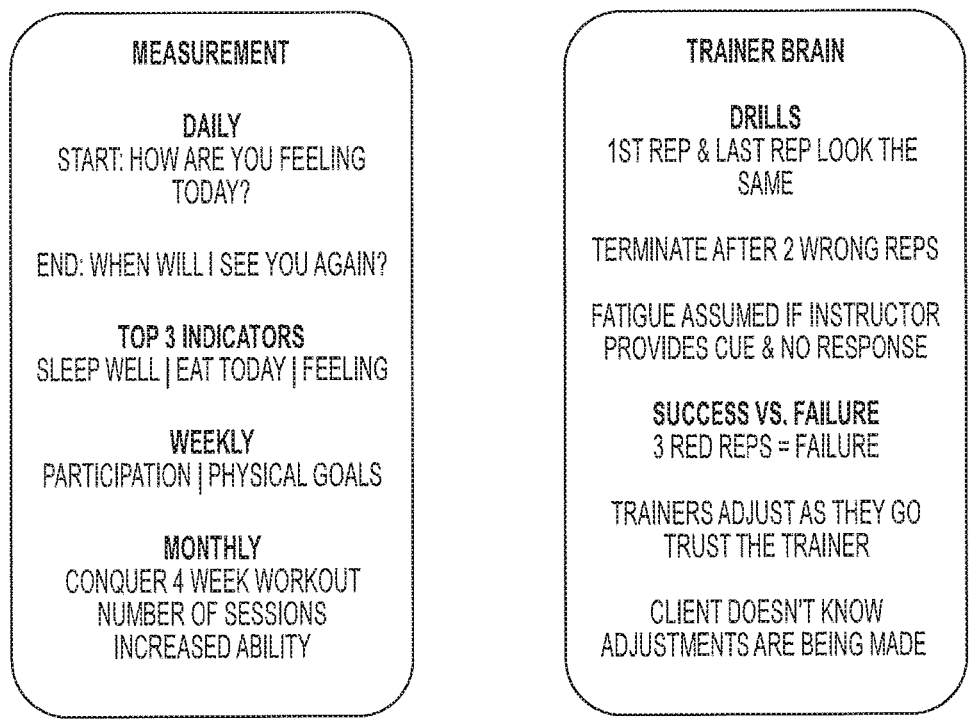
FIG. 45 illustrates example data points used by a computer to determine feedback and motivation to provide to a user during a workout session.
Figure 46:
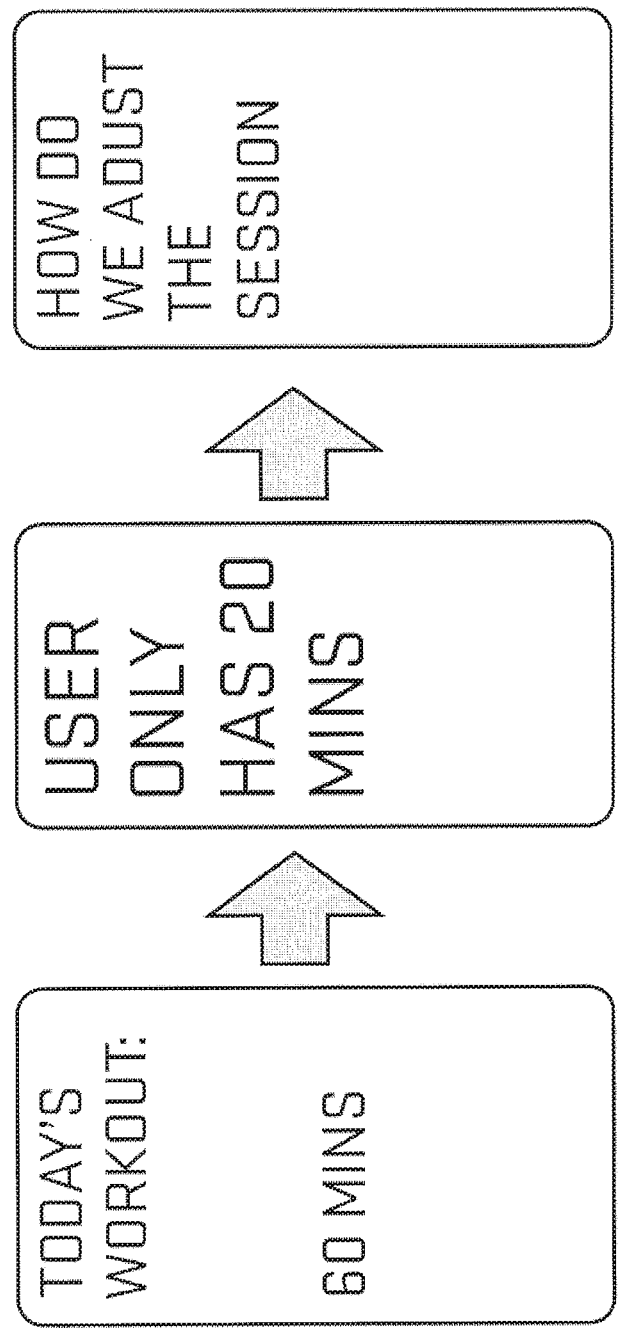
Figure 47:
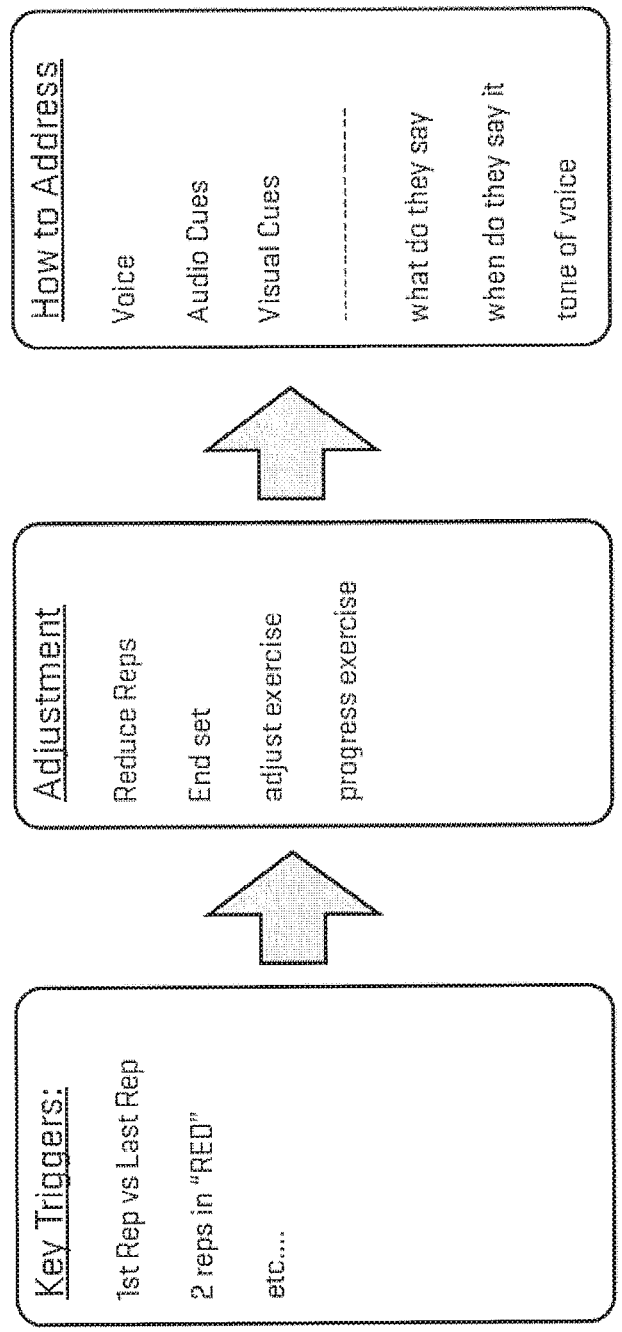
Figure 49:
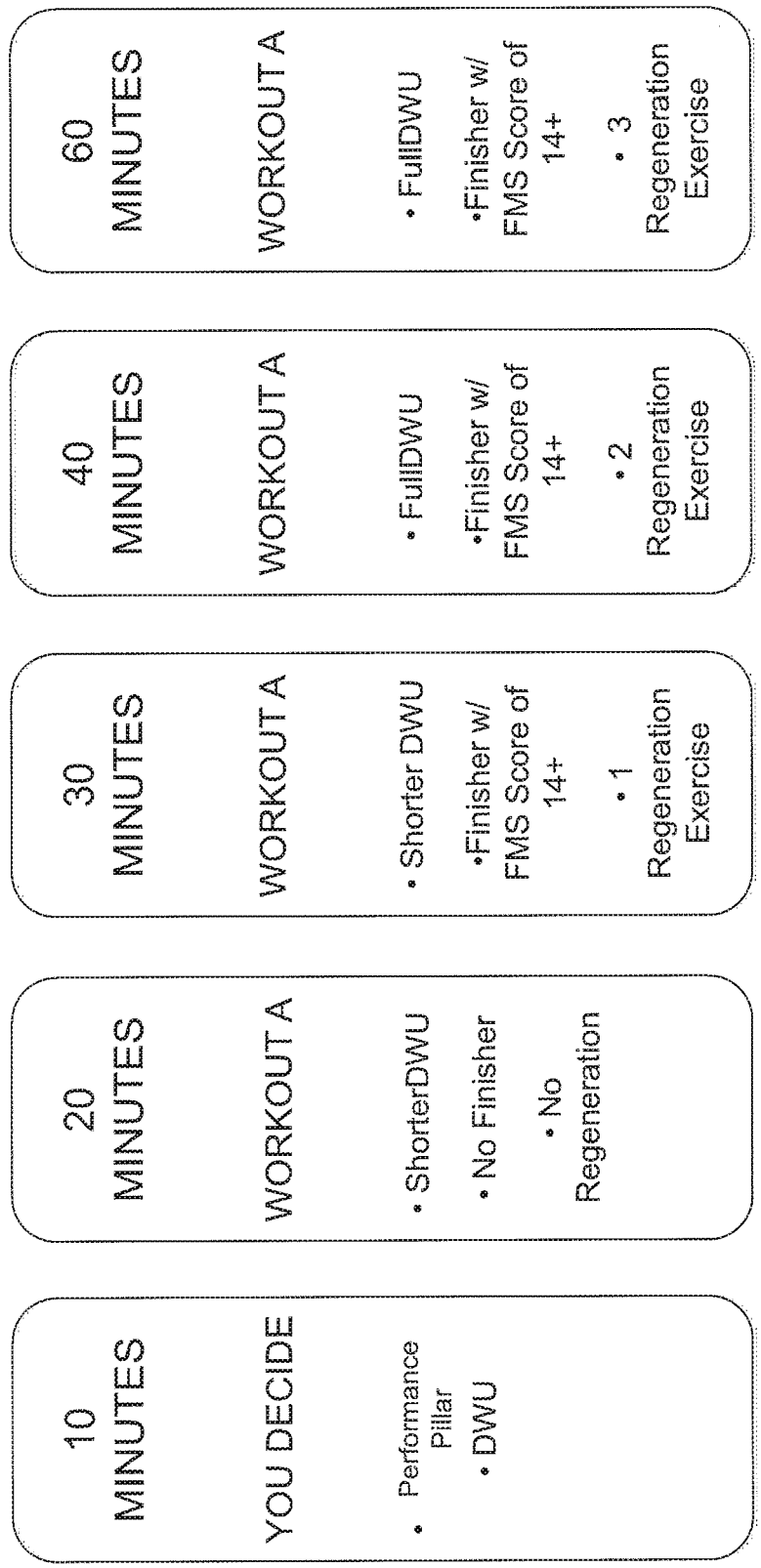

As shown by the examples in FIG. 45, the system may use data points to determine feedback and motivation to provide to a user during a workout session. The system may also revise a workout session based on the amount of time a user can commit to a workout, as described with reference to FIGS. 46-49. For example, a workout may require 60 minutes, but a user may only have 20 minutes (see FIGS. 46-47). The system may scale down the workout session based on the amount of time a user has (see FIG. 49). Adjustments may include altering an amount of warm up time, a number of sets, a number of repetitions, substitution of exercises, and the like.

The system may also account for missed workout session. If a user is able to make at least one workout session per week, the computer 102 may continue with the scheduled workout program (see, for example, FIG. 20). If the user misses an entire week, the computer 102 may start the user to perform the next workout where they left off. If the user has missed two or more weeks, the computer 102 may have the user repeat the last week they attended. The computer 102 may also send a message to a user's device (e.g., desktop computer, smart phone, laptop computer, etc.) informing of the missed workout, how many workouts have been missed, and how the missed workout has affected reaching the user's goals. The computer 102 may also include in the message a prompt to reschedule the missed workout. In some embodiments users may skip workouts.

Figure 50:
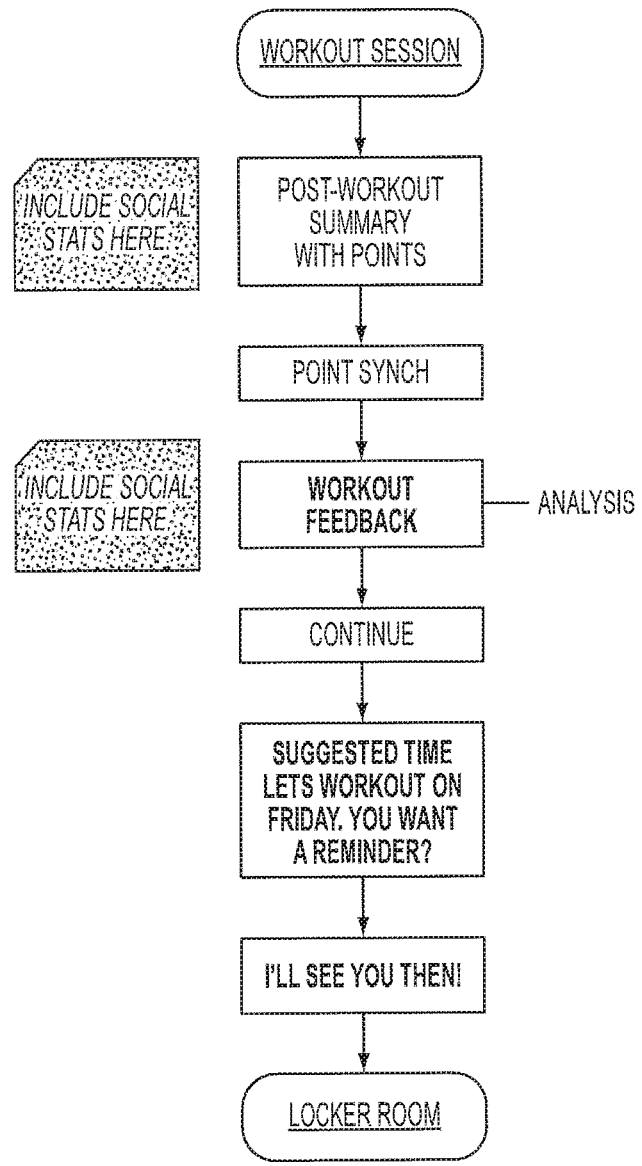
FIG. 50 illustrates an example flow diagram for providing a user with post-workout information.
Figure 51:
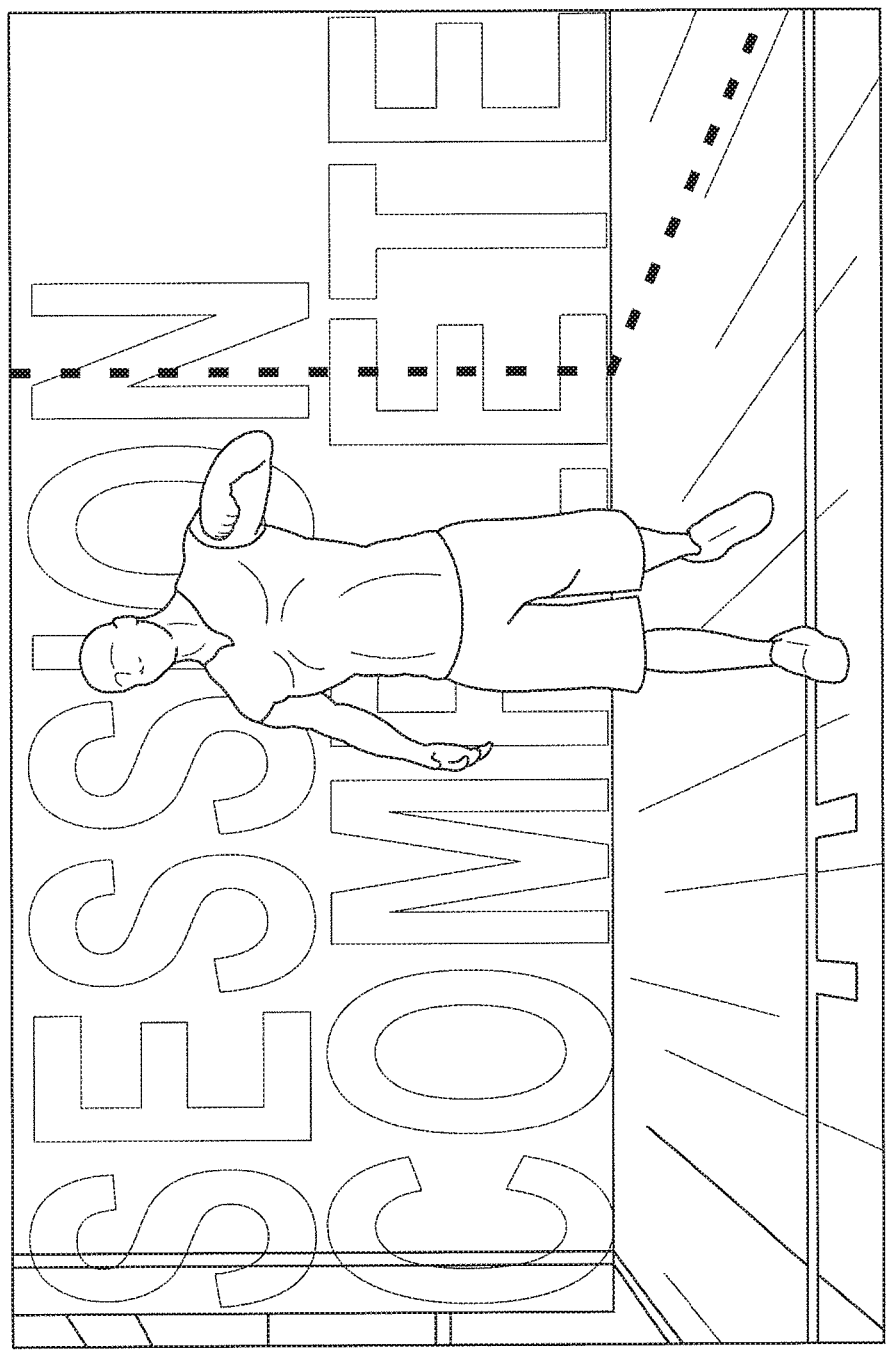
FIG. 51 illustrates an example graphical user interface informing a user that a workout session is complete.
Figure 52:
FIG. 52-53 illustrates example graphical user interfaces informing a user of their workout performance and an amount of points they have received during the workout.
Figure 53:
Figure 54:
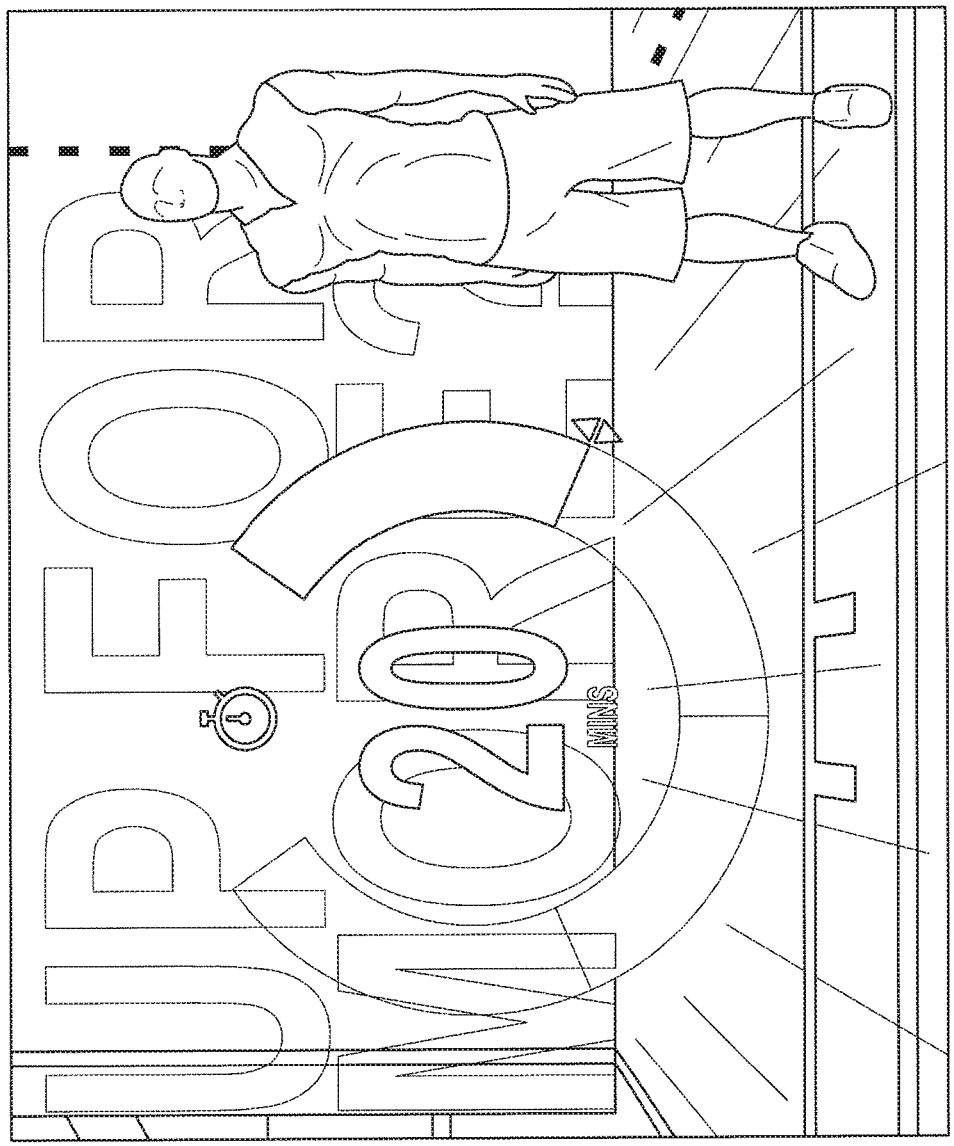
FIG. 54 illustrates an example graphical user interface prompting a user to continue exercising.

FIG. 50 illustrates a flow diagram for providing a user with post-workout information. Upon completion of a workout, the computer 102 may inform the user that the workout session is complete and may cause the trainer avatar to extend a first for a virtual first bump or other congratulatory movement (see FIG. 52). The computer 102 may inform the user of their workout performance and an amount of points associated with the workout (see FIG. 52-53). The computer 102 may also prompt the user to continue exercising (see FIG. 54). The computer 102 may also provide the user with feedback on their form, and may indicate a number of repetitions in the preferred, red, and green zones, discussed above, for each of the exercise drills.

The computer 102 may also calculate a fatigue index indicating how well the user maintained good form over the duration of a drill. For example, the fatigue index may indicate that the user was in the preferred zone for the first 4 repetitions, in the good zone for the next 5 repetitions, and in the red zone for the last repetition.

If the user trains hard during a session, the computer 102 may associate a greater number of points and unlock new workouts. Upon reaching point milestones, the user may unlock workouts and online challenges, or the user may purchase these items online through a gaming console. Other incentives may include obtaining certification as a trainer upon reaching certain fitness milestones. The user may also purchase products from a particular clothing or footwear supplier to increase rewards. For example, a product may have an embedded barcodes or other information that a user may scan or otherwise input to the computer 102 to unlock new training sessions (e.g., a session about stretching for a run). In some embodiments the purchase of certain products may allow a user to unlock new workouts. The new workouts may be related to or use the purchased products.

A display device may present a graphical user interface of a post-workout-dashboard permitting a user to review training data with analysis to view progress and improve future sessions. The user may also elect to post their workout online via social networking (e.g., via a social networking website) or otherwise share their workout sessions. Users may post comments and provide recommendations when reviewing workouts of other users. Users may also post messages to provide motivation to other users. The computer 102 may also post information to a social network when a user improves their fitness level (e.g., Bob improved his fitness level from intermediate to advanced). The computer 102 may have a dynamic recommendation engine that suggests new workouts based on profile and previous training successes. Trainers may also recommend different types of engagements such as joining a challenge or going head to head with a friend. The computer 102 may then suggest a time and date for a next workout session.

Figure 55:
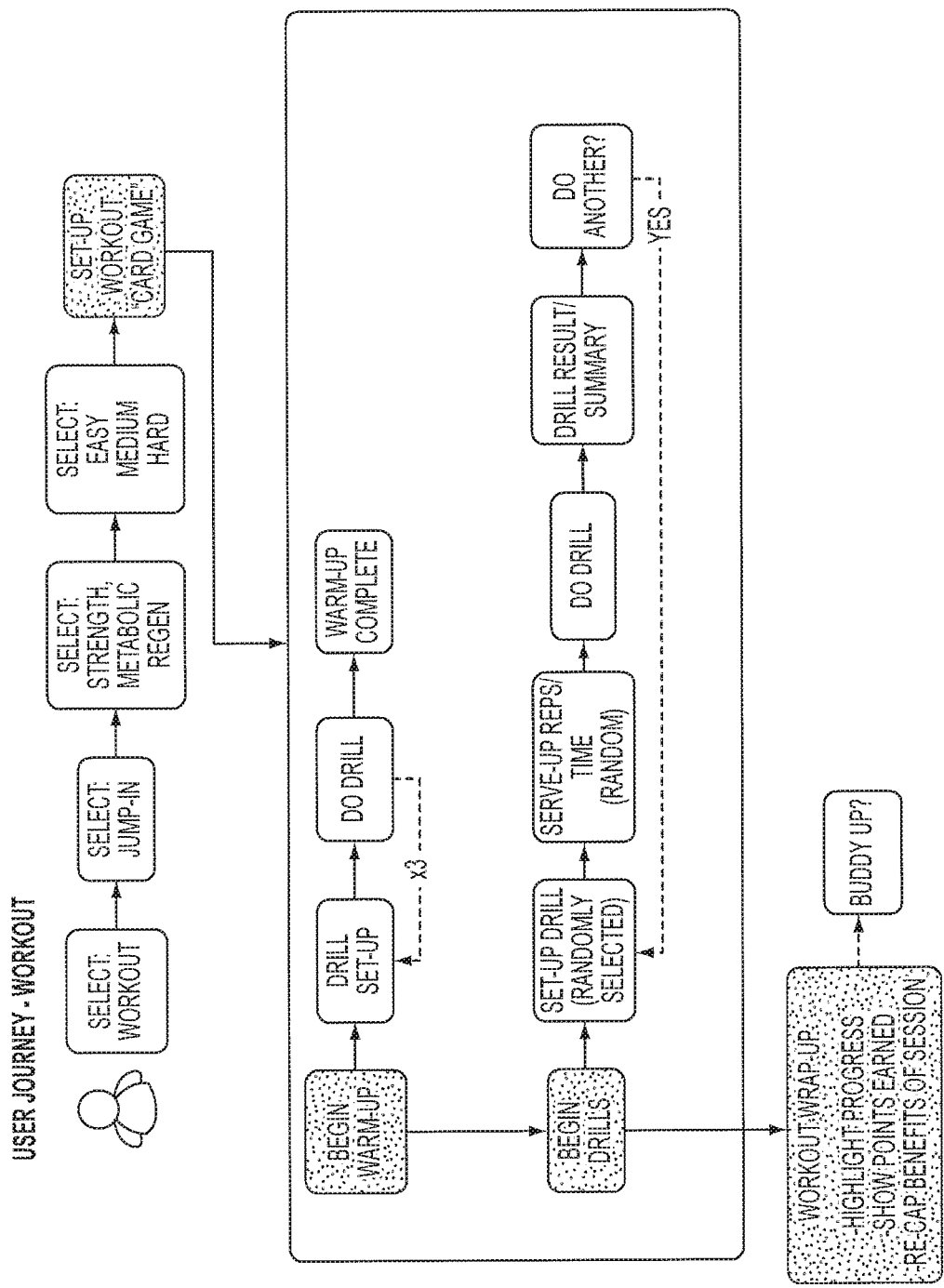
FIG. 55 illustrates an example flow diagram of a drop-in workout session.

FIG. 55 illustrates a flow diagram of a drop-in workout session and FIGS. 56-59 illustrate corresponding graphical user interfaces. A drop-in workout session may be an extra workout session in addition to the ones a user has scheduled for a particular week. A drop-in session may also be where a user opts to do a different workout than the one the scheduled for the user. The computer 102 may adjust future workouts based on the drop-in session. Adjustments may include adding or removing a future workout of a particular type (e.g., Drop-in session is an A workout, so replace a future A workout with a B workout). If a user is avoiding a particular exercise, the computer 102 may identify one or more equivalent exercises and may adjust future workouts to exclude the particular exercise. Other adjustments may also be made.

Figure 56:
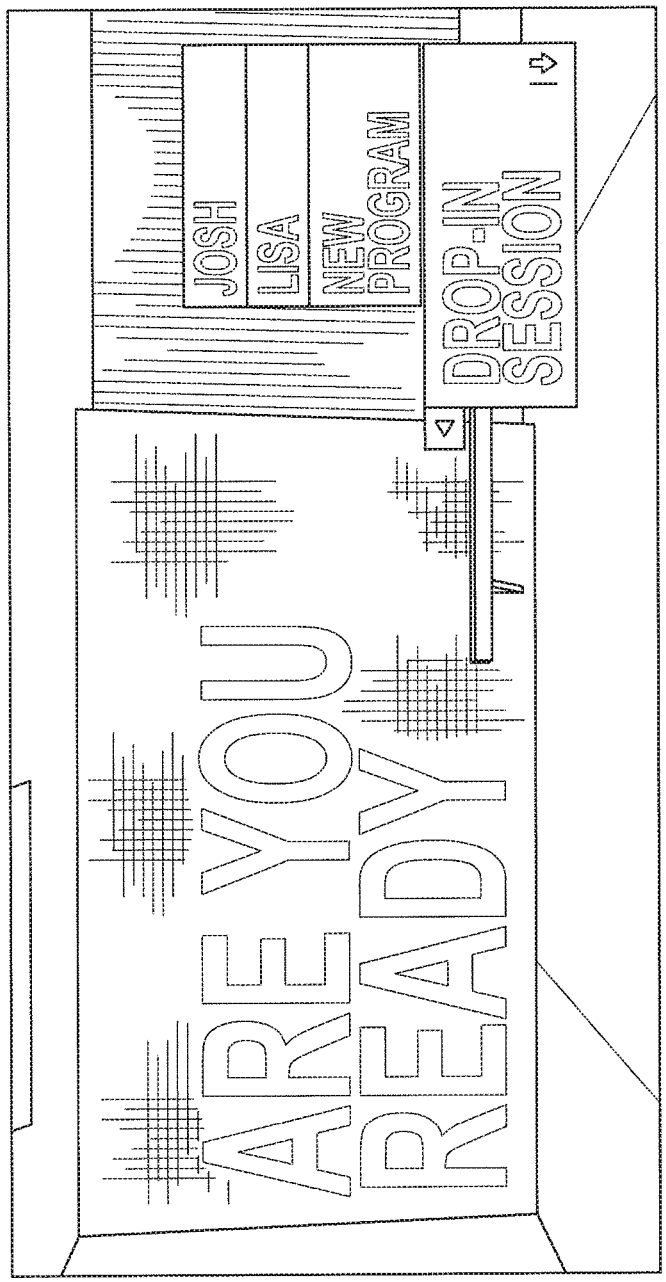
FIG. 56 illustrates an example graphical user interface permitting a user to select a drop-in workout session.
Figure 57:
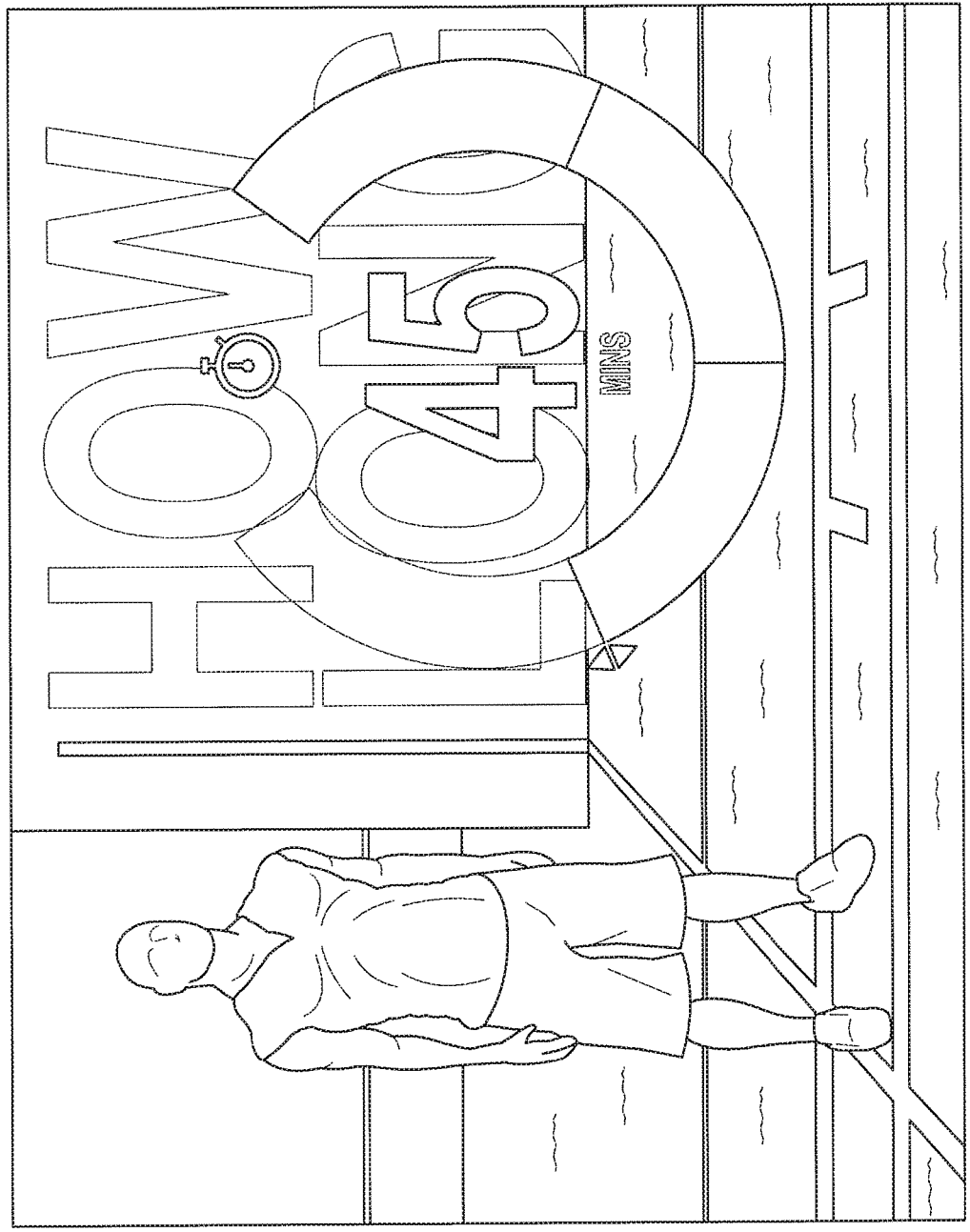
FIG. 57 illustrates an example graphical user interface prompting a user to input how long they have to work out during a drop-in session.
Figure 58:
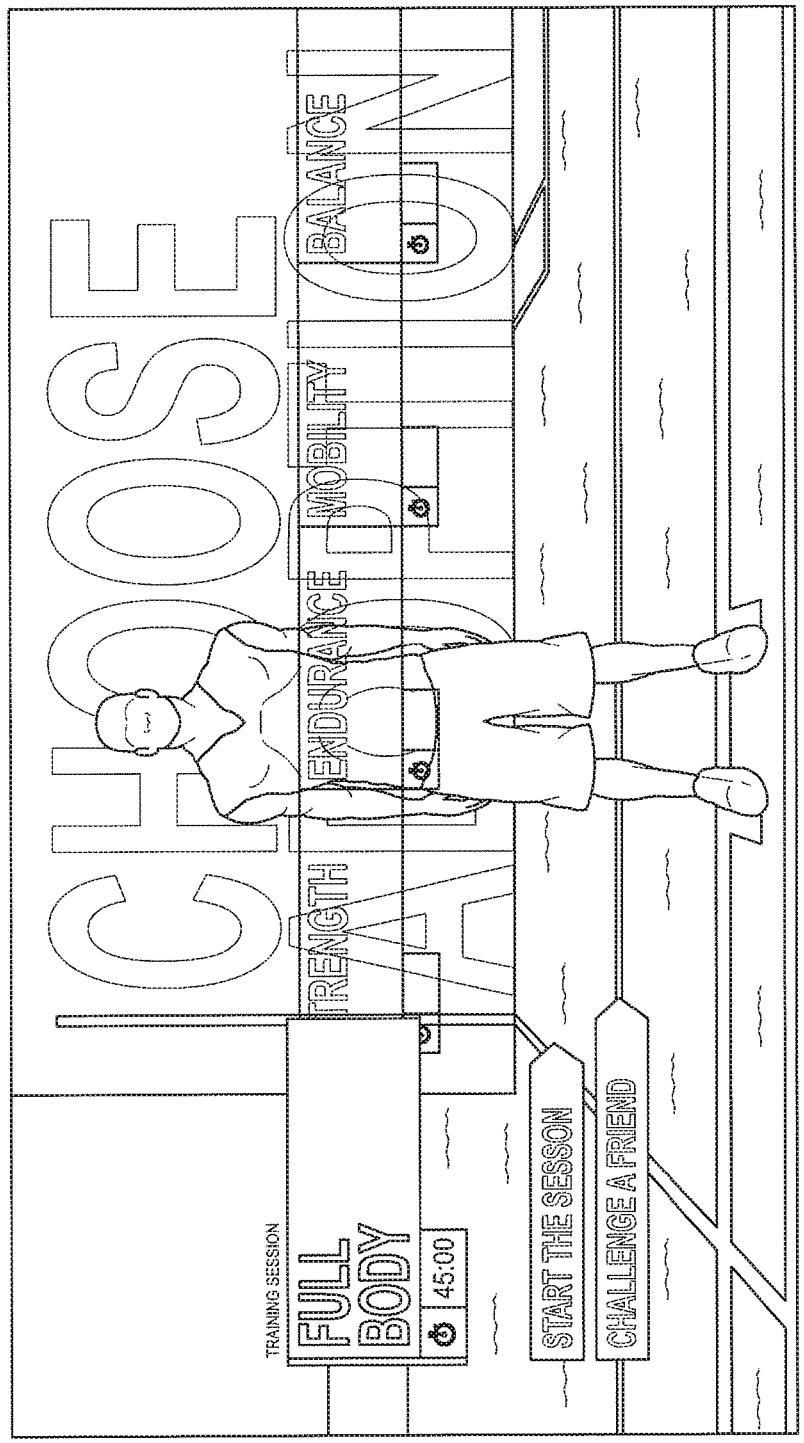
FIG. 58 illustrates an example graphical user interface prompting a user to input what type of session they want to do during a drop-in session.
Figure 59:
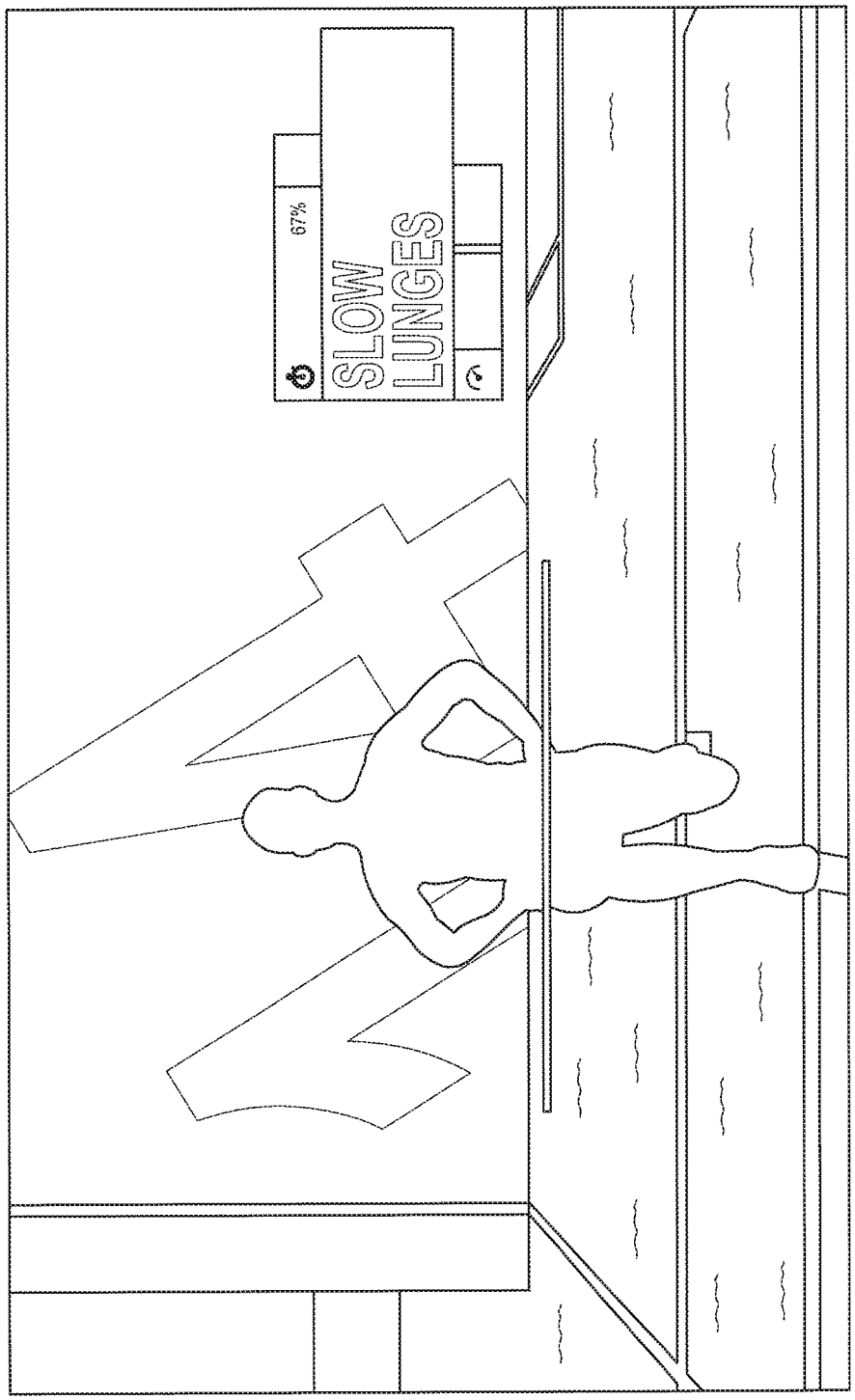
FIG. 59 illustrates an example graphical user interface of an image captured of a user working out during a drop-in session.

To initiate a drop-in session, the user may select a drop-in workout session tab of a graphical user interface (see FIG. 56). The computer 102 may ask how long the user has to work out (see FIG. 57) and what type of session the user wants to do, examples of which may include a fully body workout, a strength workout, an endurance workout, a mobility workout, or a balance workout (see FIG. 58). The computer 102 may then perform static postural analysis and/or a body scan. The computer 102 may then provide a summary of the exercise drills the user is going to perform. For example, the drills may relate to corrective/core exercises, strength/power exercises, energize/metabolic exercises, regenerate/stretch exercises. The computer 102 may lead the user through a warm up session, and then proceed to a first drill (see FIG. 59). A display device may present a demonstration of the drill. The user may then perform the drill in front of the image capturing device as the computer 102 process images of the user. The computer 102 may also provide encouragement to the user to keep going (e.g., just 5 more repetitions). The computer 102 then presents feedback to the user. Once one drill is completed, the computer 102 may prompt the user to move onto the next drill. After completion of the last drill, the computer 102 may then update a user's points and provide them with a post-workout summary.

A challenge session may be where a user competes against a ghost of their previous workout or another user. For example, the computer 102 may store video of a user performing a set of exercises, as well as performance metrics. The display may present the video of the user where the user appears translucent, and hence is denoted as a ghost. The display may overlay video recorded by the image capturing device for comparison with the ghost. The computer 102 may provide a demonstration of the challenge, and the user may perform the challenge. Upon completion of the challenge, the computer 102 may display the challenge results.

The user may also create their own challenges and workout sessions for more focused training or sharing with a social network. The user may receive points, money, or other incentives based on a number of other users who download a user created workout session. The user may also cause the computer 102 to request ghost workouts from friends or pros to aid or compare.

Figure 60:
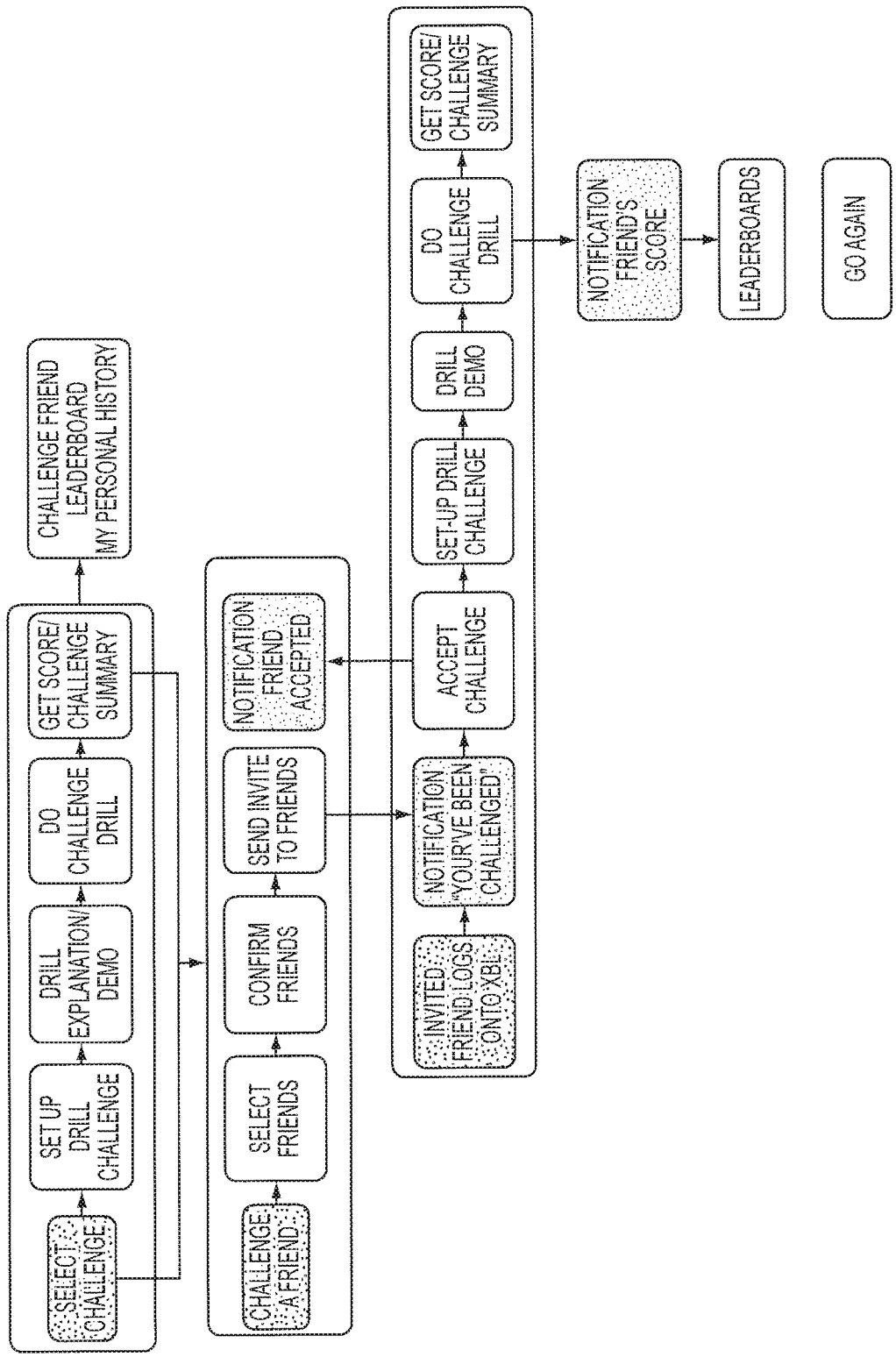
FIG. 60 illustrates an exemplary challenge drill.

Challenges may also be against multiple players at a single location (e.g., house), or via a network. FIG. 60 illustrates an exemplary challenge drill. The computer 102 may identify other users having similar fitness levels or users may challenge other users. Multiple players may simultaneously participate in a workout session at the same location, or may sequentially participate where a ghost of a player who completed a session is displayed onscreen competing against a later player. Also, the computer 102 may join an online challenge where a user may compete against another player who is also online. The online challenge may permit competitions with multiple other players. Competitions may be organized by age group, fitness level, invitation only, achieving a certain point levels, or in other manners. A ghost of the leader may be presented by the displays of all other challengers. The computer 102 may also cause a display to present a leader board showing how a user compares to other participants. Performance data, such as personal bests, may be communicated graphically and through audio devices.

CONCLUSION

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A computer implemented method comprising:
   capturing, with a wrist-worn sensor, motion parameter data of a user performing an athletic movement;
   identifying a form of the user based on an identified sensor region and based on tracking motion parameter data in the identified sensor region;
   generating, at a processor, one or more human movement screen scores based on the form of the user and based on the at least a first portion of the motion parameter data of the user performing the athletic movement;
   providing a feedback display that includes a graphical comparison of the form of the user versus a desired form and an identification of the one or more human movement screen scores;
   generating, by the processor, a personalized exercise program based on the one or more human movement screen scores, and comprising a plurality of workouts;
   in response to determining that a current workout session is not a first workout session for the user, determining a previous human movement screen score from a previous workout, a duration since the previous workout, and a number of missed workouts during the duration;
   selecting, by the processor, from the plurality of workouts in the personalized exercise program and based the duration since the previous workout and the number of missed workouts during the duration, a current workout, wherein the current workout includes one or more exercises selected based on the previous human movement screen score;
   determining a length of time that the user has available for completing the current workout of the plurality of workouts in the personalized exercise program; and
   in response to determining that a length of time associated with the current workout is greater than a length of time the user has available, adjusting the current workout.

2. The computer implemented method of claim 1, wherein the capturing motion parameter data further comprises capturing, with an image capture device, images of the user performing the athletic movement.

3. The computer implemented method of claim 2, wherein the image capture device comprises a plurality of cameras.

4. The computer implemented method of claim 1, wherein the generating one or more human movement screen scores comprises generating, at a processor, a human movement screen score based on the wrist-worn sensor and a second sensor.

5. The computer implemented method of claim 1, wherein the wrist-worn sensor, comprises an accelerometer.

6. The computer implemented method of claim 1, wherein the capturing motion parameter data further comprises capturing motion parameters with a footwear-worn accelerometer.

7. The computer implemented method of claim 1, wherein the wrist-worn sensor comprises an orientation determining sensor.

8. The computer implemented method of claim 1, wherein generating the personalized exercise program is based on the one or more human movement screen scores and an input of the user.

9. The computer implemented method of claim 8, wherein the input of the user comprises a time commitment.

10. The computer implemented method of claim 8, wherein the input of the user comprises a number of exercise sessions in a predetermined time period.

11. The computer implemented method of claim 1, wherein the generating one or more human movement screen scores comprises evaluating a form of the user by identifying locations of body parts of the user at different times.

12. The computer implemented method of claim 1, wherein the wrist-worn sensor comprises a display.

13. The computer implemented method of claim 1, wherein the personalized exercise program includes a ghost workout received from a friend of the user.

14. The computer implemented method of claim 1, wherein adjusting the current workout comprises substitution of one or more exercises within the current workout.

15. The computer implemented method of claim 1, wherein adjusting the current workout comprises altering one of: an amount of warmup time, a number of sets of an exercise of the current workout, or a number of repetitions of an exercise of the current workout.

16. The computer implemented method of claim 1, wherein the feedback display further comprises a highlighting of a body part of the user associated with improper form and a correction to a form of the user.

17. An apparatus configured to be worn on an appendage of a user, comprising:
    at least one processor;
    a display device;
    a sensor device;
    a non-transitory computer-readable medium comprising computer-executable instructions that when executed by the at least one processor cause the at least one processor to:
       capture, from the sensor device, motion parameter data of the user performing an athletic movement;
       identify a form of the user based on an identified sensor region and based on tracking motion parameter data in the identified sensor region;
       generate, by the at least one processor, one or more human movement screen scores based on the form of the user and based on the at least a first portion of the motion parameter data of the user performing the athletic movement;
       provide a feedback display that includes a graphical comparison of the form of the user versus a desired form and an identification of the one or more human movement screen scores;
       generate, by the at least one processor, a personalized exercise program based on the one or more human movement screen scores, and comprising a plurality of workouts;
       in response to determining that a current workout session is not a first workout session for the user, determine a previous human movement screen score from a previous workout, a duration since the previous workout, and a number of missed workouts during the duration;

determine by the processor from the plurality of workouts in the personalized exercise program and based on both the duration since the previous workout and the number of missed workouts during the duration, a current workout, wherein the current workout includes one or more exercises selected based on the previous human movement screen score;

determine whether a length of time associated with the current workout is greater than a length of time the user has available for completing the current workout; and automatically adjust the current workout based on determining that the length of time associated with the current workout is greater than a length of time the user has available for completing the current workout, wherein adjusting the current workout comprises altering one or more of: an amount of warmup time, a number of sets of an exercise of the current workout, and a number of repetitions of an exercise of the current workout.

18. The apparatus of claim 17, wherein the capturing comprises obtaining accelerometer data from an accelerometer located on the apparatus.

19. The apparatus of claim 18, wherein the accelerometer data comprises data from a plurality of axes.

20. The apparatus of claim 18, wherein the computer-readable medium further comprises computer-executable instructions that when executed by the at least one processor cause the at least one processor to:

collect motion parameters of the user from a footwear-worn accelerometer; and wherein generating the one or more human movement screen scores is based upon at least data obtained from the footwear-worn accelerometer and the motion parameters captured from the sensor device.

21. The apparatus of claim 18, wherein the sensor device comprises a gyroscope.

22. The apparatus of claim 17, wherein the personalized exercise program includes a ghost workout received from a friend of the user.

23. A non-transitory computer-readable medium comprising computer-executable instructions that when executed by a processor, cause the processor to perform at least:

capturing, with a body-worn sensor, motion parameter data of a user performing an athletic movement;

identifying a form of the user based on an identified sensor region and based on tracking motion parameter data in the identified sensor region;

generating, with at least one processor, one or more human movement screen scores based on the form of the user and based on the at least a first portion of motion parameter data of the user performing the athletic movement;

providing a feedback display that includes a graphical comparison of the form of the user versus a desired form and an identification of the one or more human movement screen scores;

generating, at the at least one processor, a personalized exercise program based on the one or more human movement screen scores, and comprising a plurality of workouts;

in response to determining that a current workout session is not a first workout session for the user, determining a previous human movement screen score from a previous workout, a duration since the previous workout, and a number of missed workouts during the duration, wherein the current workout session includes one or more exercises selected based on the previous human movement screen score;

determining, by the at least one processor, a next workout from the plurality of workouts based on e as the previous human movement screen score from the previous workout, the duration since the previous workout, and the number of missed workouts during the duration; and in response to determining that a length of time associated with the next workout is greater than a length of time the user has available for completing the next workout, adjusting the next workout.

* * * * *